(12) United States Patent
Piao

(10) Patent No.: US 12,358,959 B2
(45) Date of Patent: Jul. 15, 2025

(54) COMPOSITIONS AND METHODS FOR OLIGODENDROCYTE DEVELOPMENT

(71) Applicant: CHILDREN'S MEDICAL CENTER CORPORATION, Boston, MA (US)

(72) Inventor: Xianhua Piao, Boston, MA (US)

(73) Assignee: Children's Medical Center Corporation, Boston, MA (US)

(*) Notice: Subject to any disclaimer, the term of this patent is extended or adjusted under 35 U.S.C. 154(b) by 381 days.

(21) Appl. No.: 16/089,176

(22) PCT Filed: Mar. 29, 2017

(86) PCT No.: PCT/US2017/024791
§ 371 (c)(1),
(2) Date: Sep. 27, 2018

(87) PCT Pub. No.: WO2017/172945
PCT Pub. Date: Oct. 5, 2017

(65) Prior Publication Data
US 2019/0119338 A1 Apr. 25, 2019

Related U.S. Application Data

(60) Provisional application No. 62/316,491, filed on Mar. 31, 2016.

(51) Int. Cl.
| | | |
|---|---|---|
| C07K 14/47 | (2006.01) | |
| A61K 35/30 | (2015.01) | |
| A61K 38/45 | (2006.01) | |
| A61K 47/54 | (2017.01) | |
| A61P 25/00 | (2006.01) | |
| C07K 14/72 | (2006.01) | |
| C12N 9/10 | (2006.01) | |
| A61K 38/00 | (2006.01) | |

(52) U.S. Cl.
CPC .............. *C07K 14/47* (2013.01); *A61K 35/30* (2013.01); *A61K 38/45* (2013.01); *A61K 47/543* (2017.08); *A61P 25/00* (2018.01); *C07K 14/723* (2013.01); *C12N 9/1044* (2013.01); *C12Y 203/02013* (2013.01); *A61K 38/00* (2013.01)

(58) Field of Classification Search
None
See application file for complete search history.

(56) References Cited

U.S. PATENT DOCUMENTS

| 7,368,098 B2 | 5/2008 | Mueller et al. | |
|---|---|---|---|
| 2015/0238550 A1* | 8/2015 | McCown | A61P 35/00 435/235.1 |

FOREIGN PATENT DOCUMENTS

WO 2002059265 A2 8/2002

OTHER PUBLICATIONS

Aharoni, R. 2015 Expert Rev. Neurother. 15(12): 1369-1372. (Year: 2015).*
Zhang, Y., et al. 2013 Neurosci Bull 29(2): 144-154. (Year: 2013).*
Stoveken, H., et al. 2015 PNAS 112(19): 6194-6199 (7 pages, including correction p. E3452). (Year: 2015).*
Münzel, E.J., et al. 2013 Drugs 73: 2017-2029. (Year: 2013).*
Ackerman et al., "The adhesion GPCR Gpr56 regulates oligodendrocyte development via interactions with Ga 12/13 and RhoA," Nature Communications, Jan. 21, 2015 (Jan. 21, 2005), vol. 6:6122, pp. 1-14 (entire document).
Giera et al., "The adhesion G protein-coupled receptor GPR56 is a cell-autonomous regulator of oligodendrocyte development," Nature Communications, Jan. 21, 2015 (Jan. 21, 2015), vol. 6:6121, pp. 1-12 (entire document).
Komaromi, et al., "Factor XIII: novel structural and functional aspects," Journal of Thrombosis and Haemostasis, Jan. 31, 2011 (Jan. 31, 2011), vol. 9, No. 1, pp. 9-20, entire document.
Liebscher et al., "New functions and signaling mechanisms for the class of adhesion G protein-coupled receptors," Annals of the New York Academy of Sciences, Nov. 25, 2014 (Nov. 25, 2014), vol. 1333, No. 1, pp. 43-64, entire document.
Yang et al., "G protein-coupled receptor 37 is a negative regulator of oligodendrocyte differentiation and myelination," Nature Communications, Mar. 10, 2016 (Mar. 10, 2016), vol. 7:10884, pp. 1-11 (entire document).
Zaro, J., "Lipid-based drug carriers for prodrugs to enhance drug delivery," The AAPS Journal, Oct. 1, 2014 (Oct. 1, 2014), vol. 17, No. 1, pp. 83-92, entire document.
International Search Report and Written Opinion for corresponding PCT Patent Application No. PCT/US2017/024791, dated Jun. 30, 2017 (12 pages).
Aeschlimann et al., "Identification of Gln726 in Nidogen as the Amine Acceptor in Transglutaminase-catalyzed Cross-linking of Laminin-Nidogen Complexes," The Journal of Biological Chemistry, Jun. 5, 1992, vol. 267, No. 16, pp. 11316-11321.
Belkin, Alexey M., "Extracellular TG2: emerging functions and regulation," The FEBS Journal, 2011, vol. 278, pp. 1704-4716.
Demberg et al., "Activation of Adhesion G protein-coupled Receptors: Agonist Specificity of Stachel Sequence-Derived Peptides," The Journal of Biological Chemistry, Mar. 17, 2017, vol. 292, No. 11, pp. 4383-4394.
Dutta et al., "Combinatorial actions of Tgfβ and Activin ligands promote oligodendrocyte development and CNS myelination," Development, 2014, vol. 141, pp. 2414-2428.
Erny et al., "Host microbiota constantly control maturation and function of microglia in the CNS," Nature Neuroscience, Jul. 2015, vol. 18, No. 7, pp. 965-977.
Hamann et al., "International Union of Basic and Clinical Pharmacology. XCIV. Adhesion G Protein-Coupled Receptors," Pharmacological Reviews, Apr. 2015, vol. 67, No. 2, pp. 338-367.
Jeong et al., "Loss of col. 3a1, the Gene for Ehlers-Danlos Syndrome Type IV, Results in Neocortical Dyslamination," PLoS ONE, Jan. 2012, vol. 7, No. 1, e29767, pp. 1-7.

(Continued)

Primary Examiner — Marsha Tsay
(74) Attorney, Agent, or Firm — Greenberg Traurig, LLP; Melissa Hunter-Ensor; Evelyn M. Kwon

(57) ABSTRACT

The present invention provides compositions and methods for increasing myelination in the nervous system or a subject, including for the treatment of a disease or disorder characterized by a deficiency or loss of myelination (e.g., a demyelinating disease).

14 Claims, 38 Drawing Sheets

Specification includes a Sequence Listing.

(56) References Cited

OTHER PUBLICATIONS

Kuffer et al., "The prion protein is an agonistic ligand of the G protein-coupled receptor Adgrg6," Nature, Aug. 25, 2016, vol. 536, No. 7617, pp. 464-468.
Langenhan et al., "Adhesion G protein-coupled receptors in nervous system development and disease," Nature Reviews Neuroscience, Sep. 2016, vol. 17, pp. 550-561.
Langenhan et al., "Sticky Signaling-Adhesion Class G Protein-Coupled Receptors Take the Stage," Science Signaling, May 21, 2013, vol. 6, No. 276, re3, pp. 1-21.
Liebscher et al., "A Tethered Agonist within the Ectodomain Activates the Adhesion G Protein-Coupled Receptors GPR126 and GPR133," Cell Reports, Dec. 24, 2014, vol. 9, pp. 2018-2026.
Liu et al., "Type III collagen is crucial for collagen I fibrillogenesis and for normal cardiovascular development," Proceedings of the National Academy of Sciences of the United States of America, Mar. 1997, vol. 94, pp. 1852-1856.
Luo et al., "G protein-coupled receptor 56 and collagen III, a receptor-ligand pair, regulates cortical development and amination," Proceedings of the National Academy of Sciences of the United States of America, Aug. 2, 2011, vol. 108, No. 31, pp. 12925-12930.
Matcovitch-Natan., "Microglia development follows a stepwise program to regulate brain homeostasis," Science, Aug. 19, 2016, vol. 353, No. 6301, pp. aad8670-1-aad8670-12.
Miron et al., "M2 microglia/macrophages drive oligodendrocyte differentiation during CNS remyelination," Nature Neuroscience, Sep. 2013, vol. 16, No. 9, pp. 1211-1218.
Monk et al., "A G Protein-Coupled Receptor Is Essential for Schwann Cells to Initiate Myelination," Science, Sep. 11, 2009, vol. 325, No. 5946, pp. 1402-1405.
Petersen et al., "The Adhesion GPCR GPR126 Has Distinct, Domain-Dependent Functions in Schwann Cell Development Mediated by Interaction with Laminin-211," Neuron, Feb. 18, 2015, vol. 85, pp. 755-769.
Piao et al., "Genotype-Phenotype Analysis of Human Frontoparietal Polymicrogyria Syndromes," Annals of Neurology, 2005, vol. 58, pp. 680-687.
Piao et al., "G Protein-Coupled Receptor-Dependent Development of Human Frontal Cortex," Science, Mar. 26, 2004, vol. 303, pp. 2033-2036.
Pinkas et al., "Transglutaminase 2 Undergoes a Large Conformational Change upon Activation," PLoS Biology, Dec. 2007, vol. 5, No. 12, e327, pp. 2788-2796.
Salzman et al., "Structural Basis for Regulation of GPR56/ADGRG1 by Its Alternatively Spliced Extracellular Domains," Neuron, Sep. 21, 2016, vol. 91, pp. 1292-1304.
Scholz et al., "The Adhesion GPCR Latrophilin/CIRL Shapes Mechanosensation," Cell Reports, May 12, 2015, vol. 11, pp. 866-874.
Sharon et al., "The Central Nervous System and the Gut Microbiome," Cell, Nov. 3, 2016, vol. 167, pp. 915-932.
Shin et al., "Very large G protein-coupled receptor 1 regulates myelin-associated glycoprotein via G$\alpha$s/G$\alpha$q-mediated protein kinases A/C," Proceedings of the National Academy of Sciences of the United States of America, Nov. 19, 2013, vol. 110, No. 47, pp. 19101-19106.
Tsai et al., "Oligodendrocyte precursors migrate along vasculature in the developing nervous system," Science, Jan. 22, 2016, vol. 351, No. 6271, pp. 379-384.
Van Strien et al., "Tissue Transglutaminase Activity Is Involved in the Differentiation of Oligodendrocyte Precursor Cells into Myelin-Forming Oligodendrocytes During CNS Remyelination," GLIA, 2011, vol. 59, pp. 1622-1634.
Wheeler et al., "Extracellular Cues Influencing Oligodendrocyte Differentiation and (Re)myelination," Experimental Neurology, Sep. 2016, vol. 283, Pt. B, pp. 512-530.
Xu et al., "GPR56, an atypical G protein-coupled receptor, binds tissue transglutaminase, TG2, and inhibits melanoma tumor growth and metastasis," Proceedings of the National Academy of Sciences of the United States of America, Jun. 13, 2006, vol. 103, No. 24, pp. 9023-9028.
Zhang et al., "An RNA-Sequencing Transcriptome and Splicing Database of Glia, Neurons, and Vascular Cells of the Cerebral Cortex," The Journal of Neuroscience, Sep. 3, 2014, vol. 34, No. 36, pp. 11929-11947.

* cited by examiner

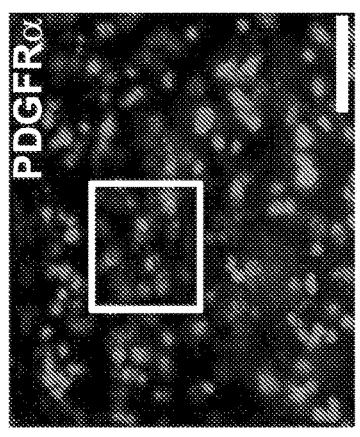
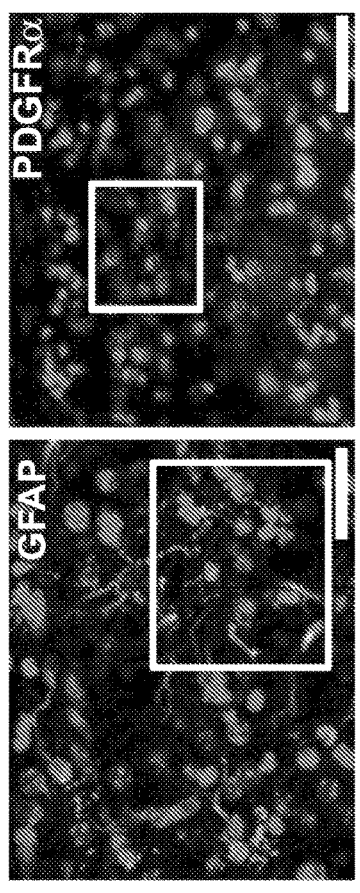
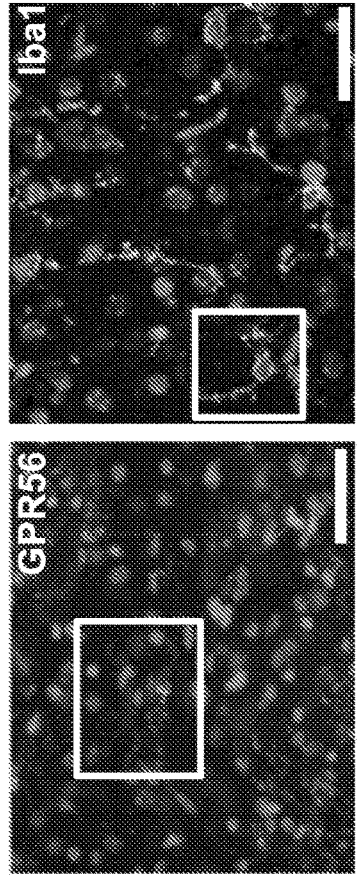

| FIGS. 3A-3C |
| FIGS. 3D-3F |
| FIGS. 3G-3L |
FIG. 3
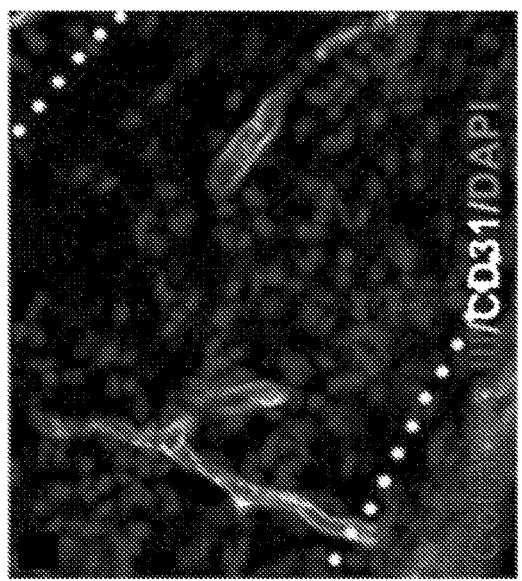
FIG. 3A
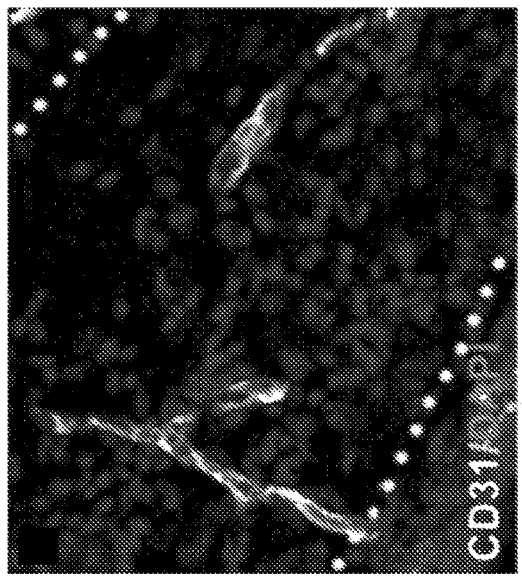
FIG. 3B
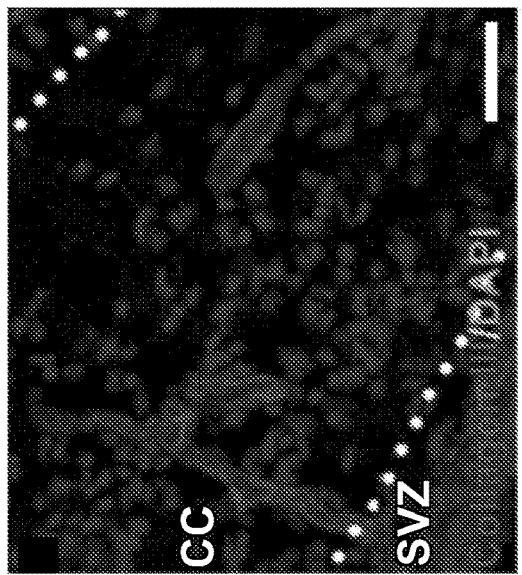
FIG. 3C

| FIGS. 4A-4B |
|---|
| FIGS. 4C-4E |
| FIGS. 4F-4O |

```
                                                                    SexAI
gas6+/+              : CCCACCAGTTCCTGCGCAGAACCCGCAGAACCCGCAGACCAGGTGTCCGTGTCCTCGCGCCA
gas6stl228/stl228    : CCCACCAGTTCCTGCGCAGAACCCGCAGAACCCGCAGAGC-----AGGTGTCCGTGTCCTCGCGCCA Gas6 (WT)            : SVSSRQAHQFLRRTRRANQVFEETKQGHLERECVEEKCTKEEAREVFENDPETEYFYP
Gas6 (stl228)        : SVSSRQAHQFLRRTRRA GVRVLAPGPPVPAQNPQSQPGVRGDQTGPPGEGVCGGEVH*
                                                                    HpyCH4IV
mpp6a+/+             : AGGATGTTAAGCTGGAGGCGGTTCAAAGTAATAACGTGGAGCTAGTGAGTGAGATCCT
mpp6astl233/stl233   : AGGATGTTAAGCTGGAGGCGGTTCAAAGTAATAAGG--GGAGCTAGTGAGTGAGATCCT Mpp6a (WT)           : DVKLEAVQSNNVELVSEILSDMSSLIIRDESAAELSNILKEPHFQSLLEAHDKVASKS
Mpp6a(stl233)        : DVKLEAVQSNKGS*
```

```
                                                                               BstNI
mpp6b+/+        : TCTCTGTGTTTGTTCAGCTATGCAGCAGGTGTTGGATAACCTGGGCGAGTTGCCCTCC
mpp6bstl234/stl234 : TCTCTGTGTTTGTTCAGCTATGCAGCAGGTGTTGGA--------GGGCGAGTTGCCCTCC Mpp6b (WT)      : MITAMQQVLDNLGELPSTTGAKDIDLIFLKGIMESPIVRSLAKAHERLEDVKLEAVQE
Mpp6a (stl234)  : MITAMQQVL---EGELPSTTGAKDIDLIFLKGIMESPIVRSLAKAHERLEDVKLEAVQE
```

FIG. 4D

```
                                                   DdeI
pleca+/+        : GAAACATAAGAAGAAGAAGAAAAAACTAGGAATAAGACTGAGGAAGAGGACGAAAAG
plecastl261/stl261 : GAAACATAAGAAGAAGAAGAA-----------------TGAGGAAGAGGACGAAAAG Pleca (WT)      : KHKKKEKLGNKTEEEDKKEEGKDENKEEGKEEKTITVRKRNKKHLKVTIAPGTVTISA
Pleca (stl261)  : KHKKKK*
```

FIG. 4E

```
                                                         Hpy188III
plecb+/+        : GATGGACACATAACCTGATCTCCCTCCTTCCTGGAGTTCCTCTCTGGAGAGACGCTGGTGAGTG
plecbstl236/stl236 : GATGGACACATAACCTGATCTCCCTCCTTCCTGGAG------------AGACGCTGGTGAGTG Plecb (WT)      : DGHNLISLLEVLSGETLPRERGRMRFHKLQNVQIALDFLRHRQVKLVNIRNDDIADGN
Plecb (stl236)  : DGHNLISLLERRW*
```

5 dpf
*mbp*
*gas6* (control)   N=11/12

*gas6*^*stl228/stl228*   N=5/8

*mpp6a* (control)   N=17/18

*mpp6a*^*stl233/stl233*   N=5/7

*mpp6b* (control)   N=24/24

*mpp6b*^*stl234/stl234*   N=4/4

*pleca* (control)   N=18/18

*pleca*^*stl261/stl261*   N=4/4

*plecb* (control)   N=38/38

*plecb*^*stl236/stl236*   N=10/10

FIGS. 5A–5C
FIGS. 5D–5F
FIGS. 5G–5I
FIGS. 5J–5L
FIGS. 5M–5O
FIGS. 5P–5R
FIGS. 5S–5U
FIGS. 5V–5X
FIG. 5Y
FIG. 5
FIG. 5A
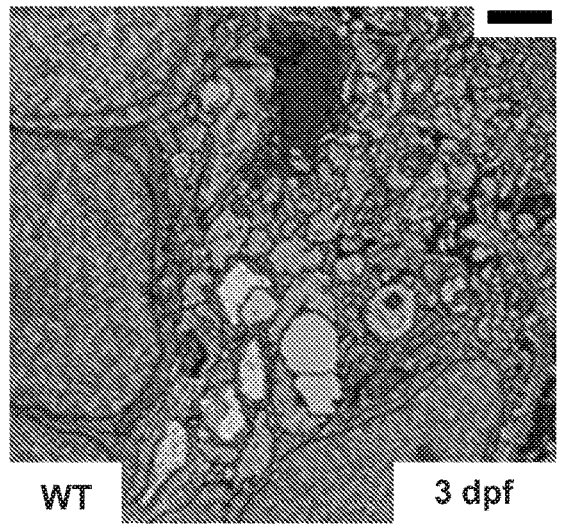
WT    3 dpf
FIG. 5B
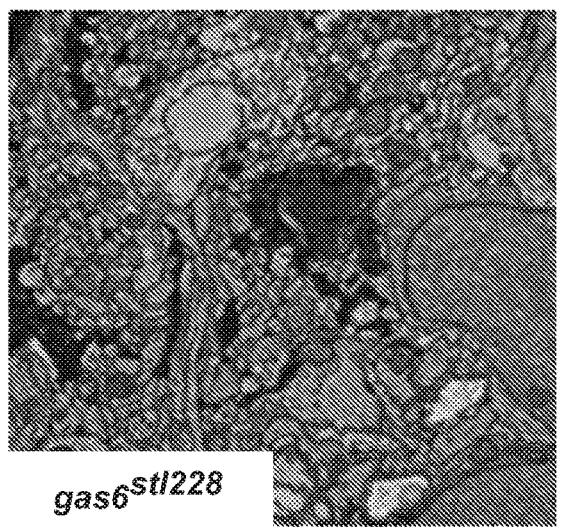
gas6$^{stl228}$
FIG. 5C
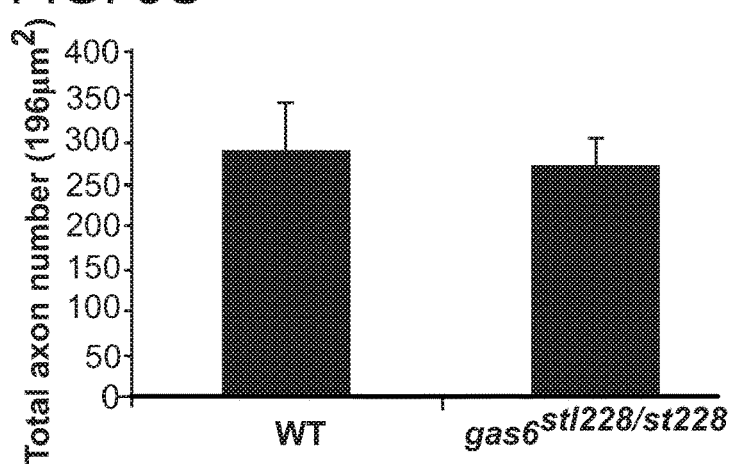

*mpp6a*$^{stl233}$

WT pleca$^{stl261}$

FIG. 6
| FIGS. 6A-6B |
|---|
| FIGS. 6C-6H |
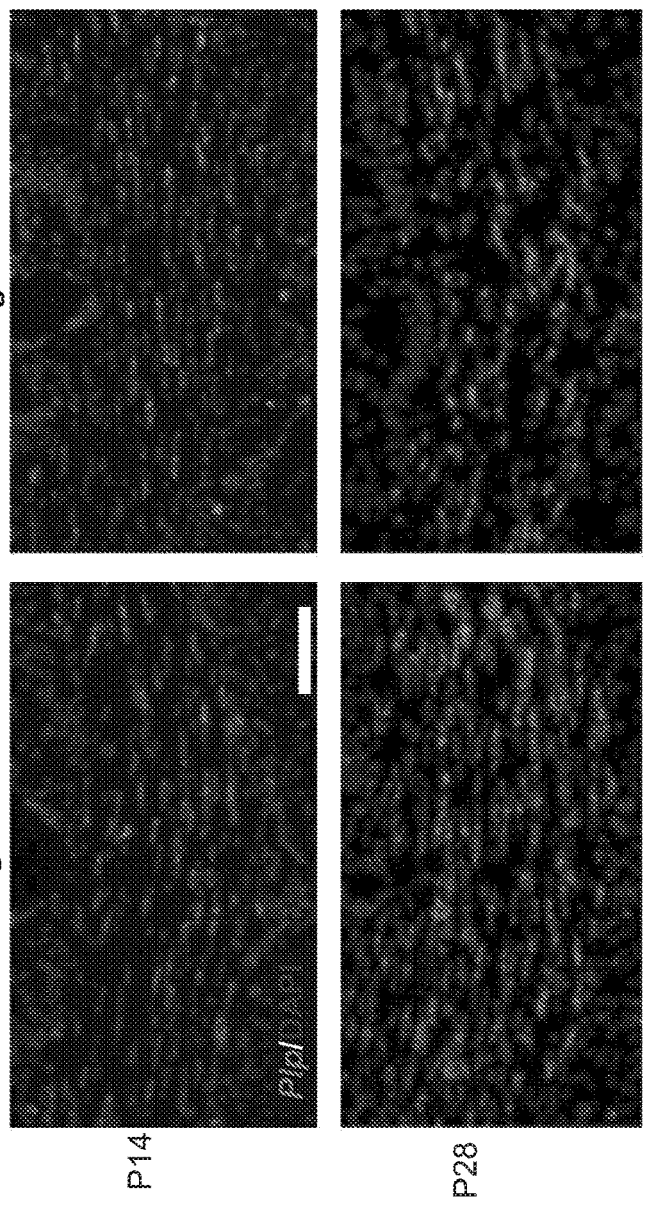
FIG. 6A
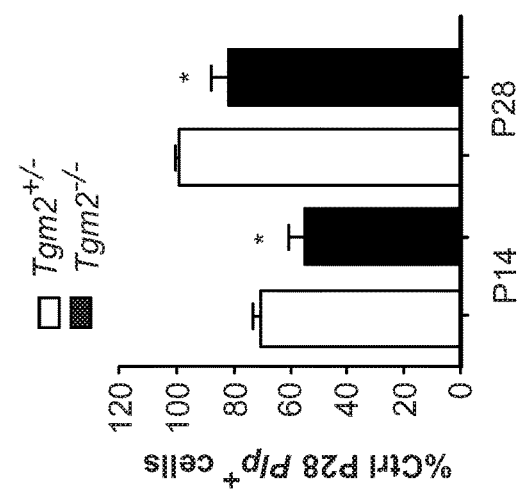
FIG. 6B

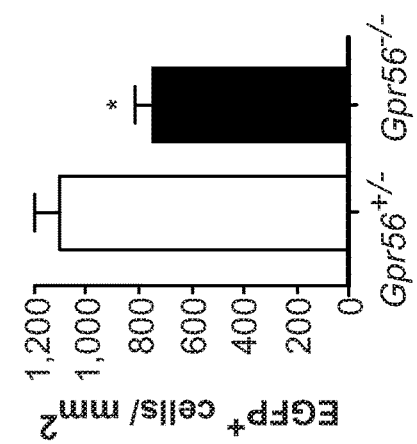
FIG. 7D
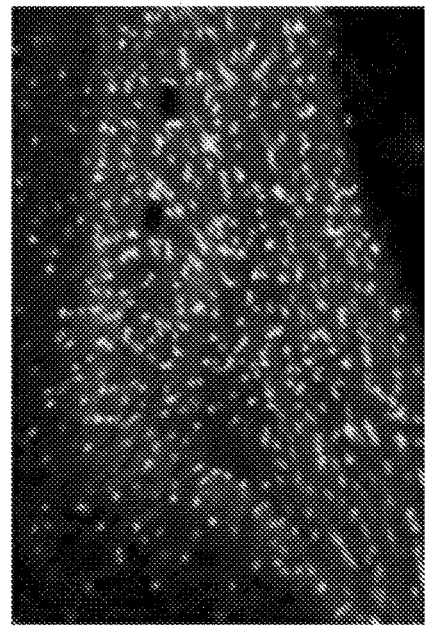
FIG. 7C
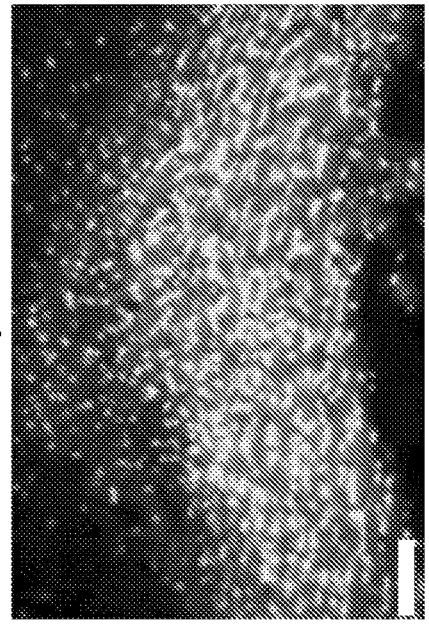

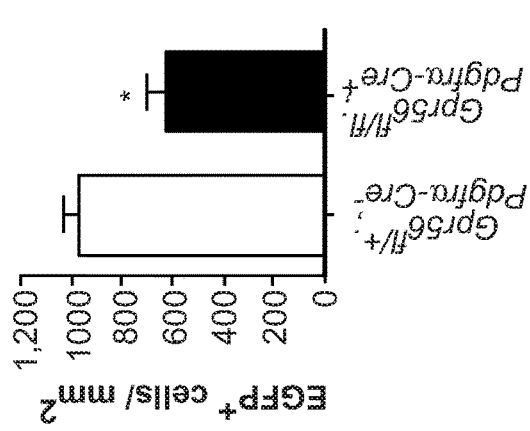
FIG. 7F
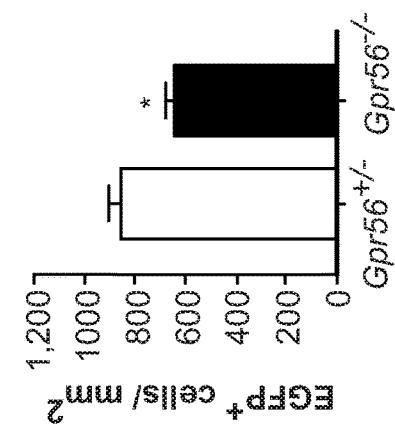
FIG. 7H
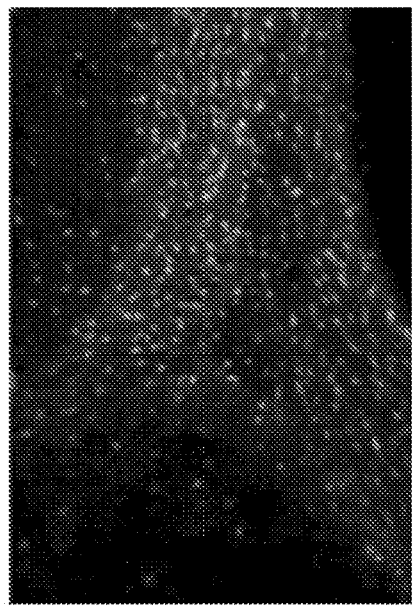
FIG. 7E
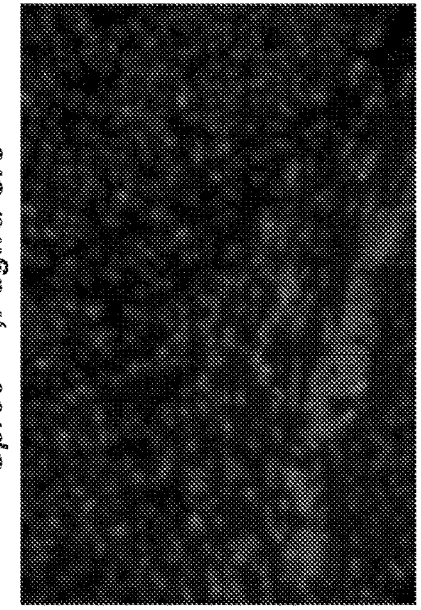
FIG. 7G
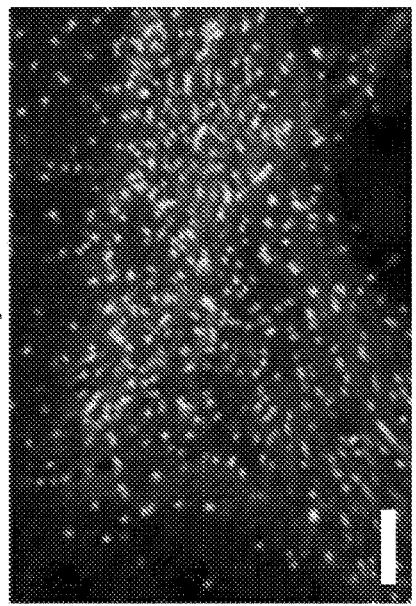
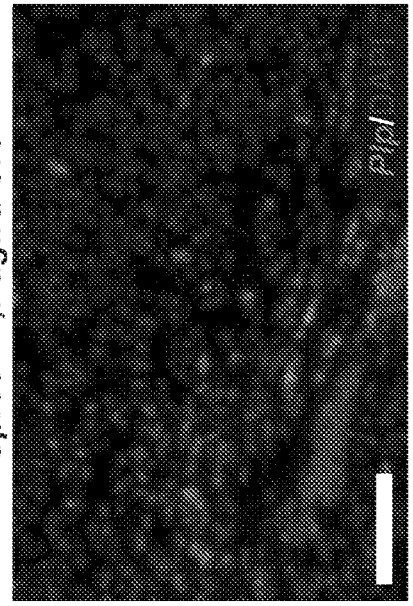

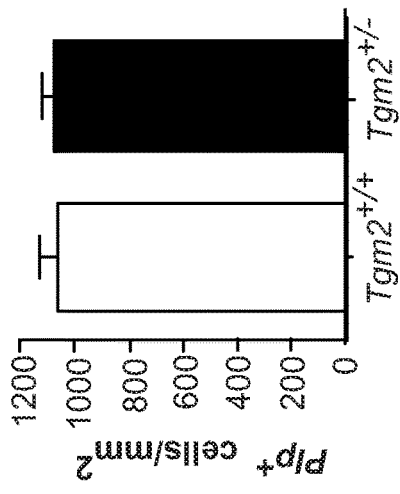
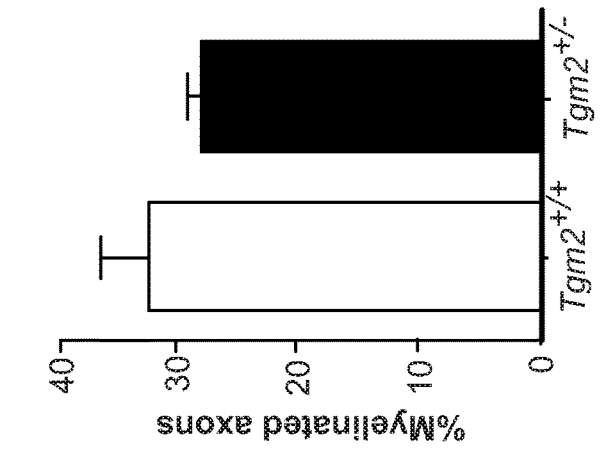
FIG. 9A  FIG. 9B
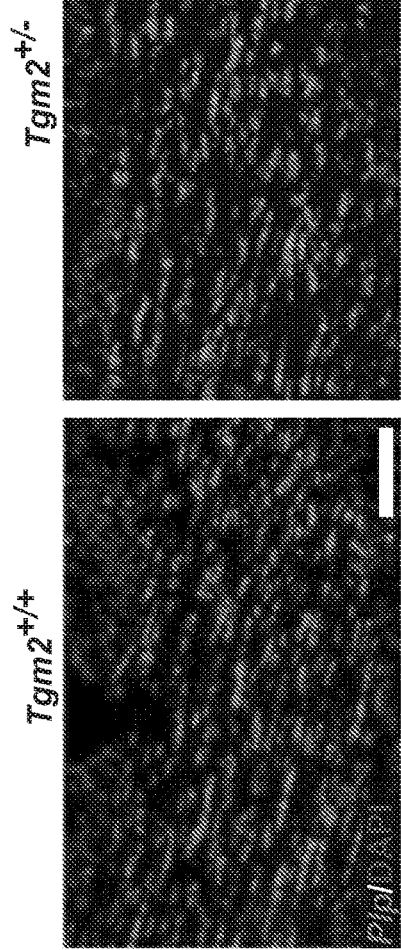
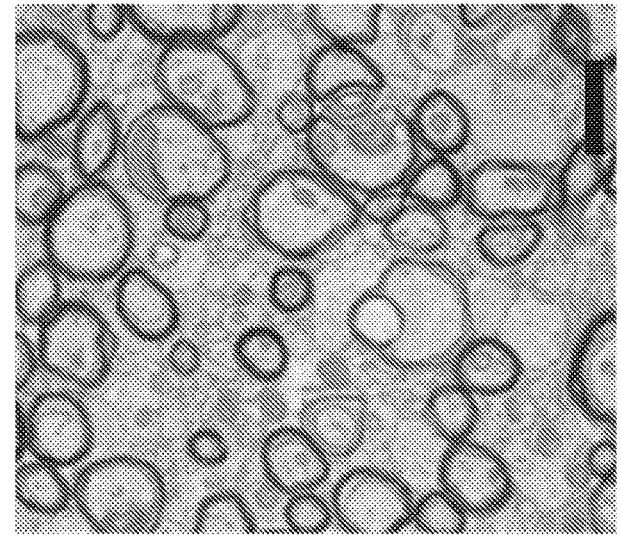
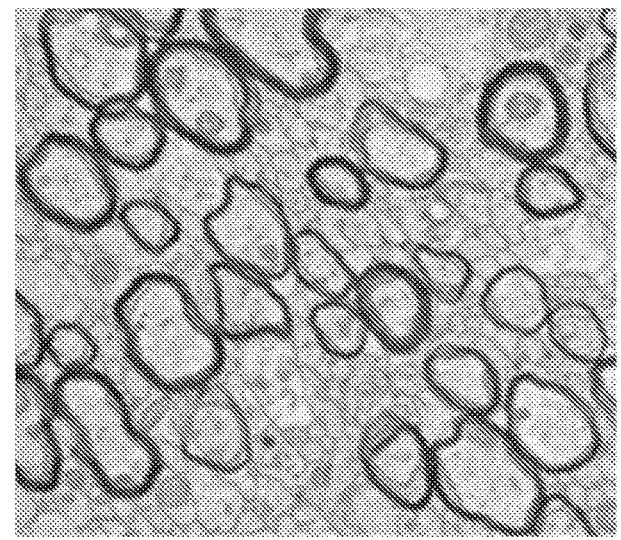
FIG. 9C  FIG. 9D

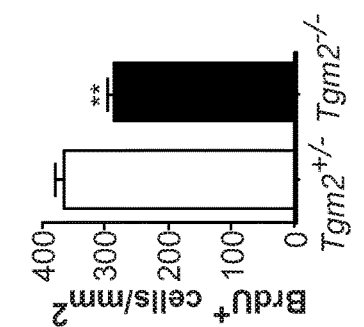
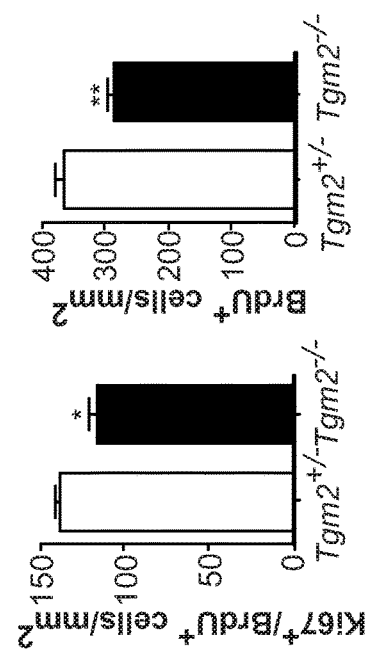
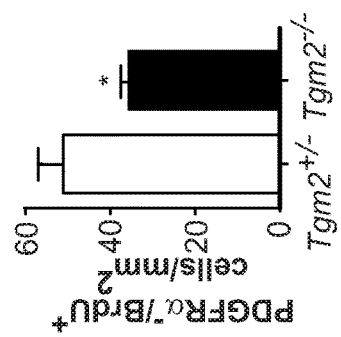
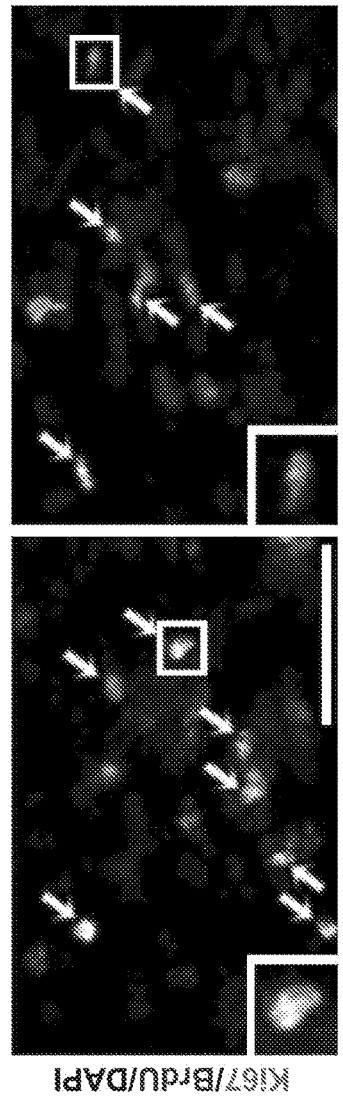
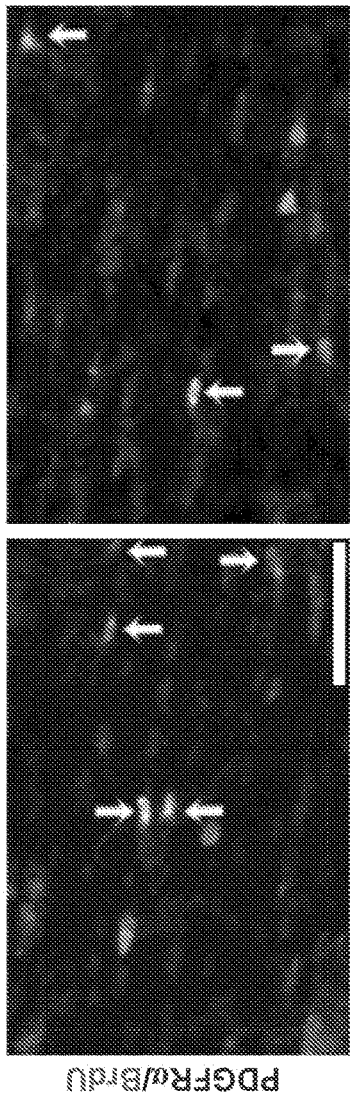

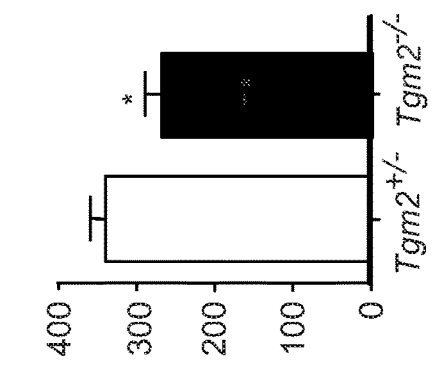
FIG. 11B
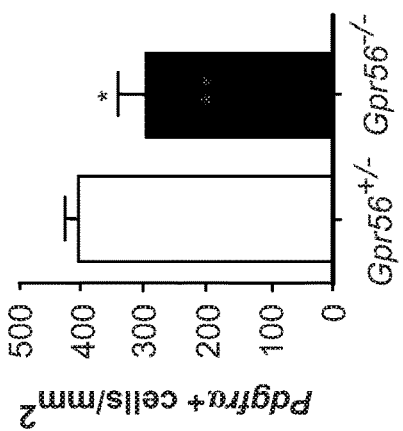
FIG. 11D
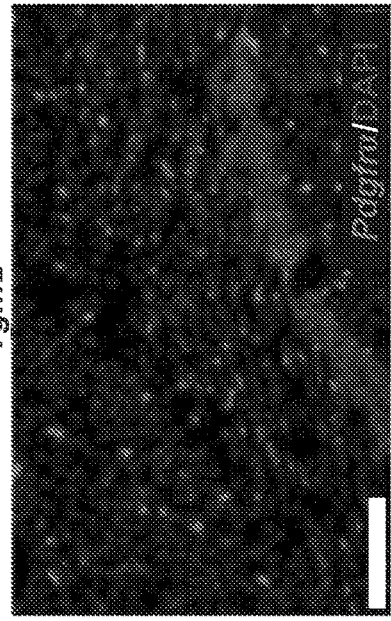
FIG. 11A
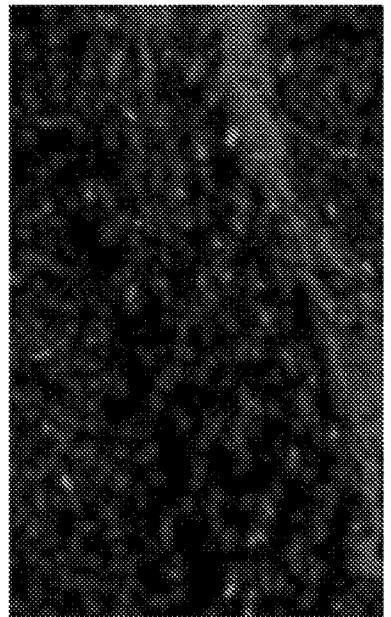
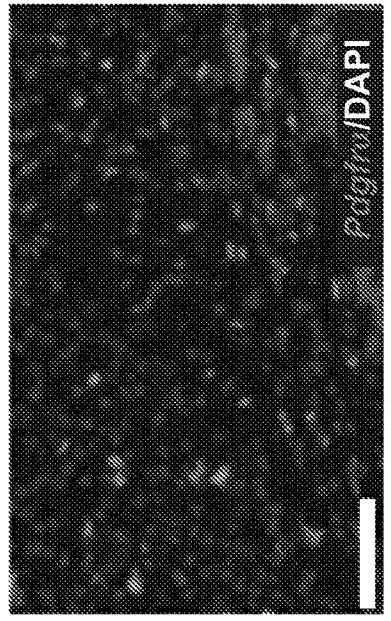
FIG. 11C

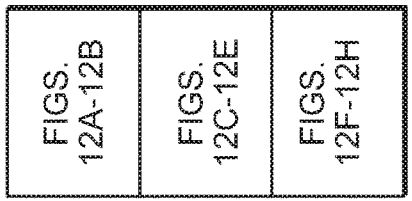
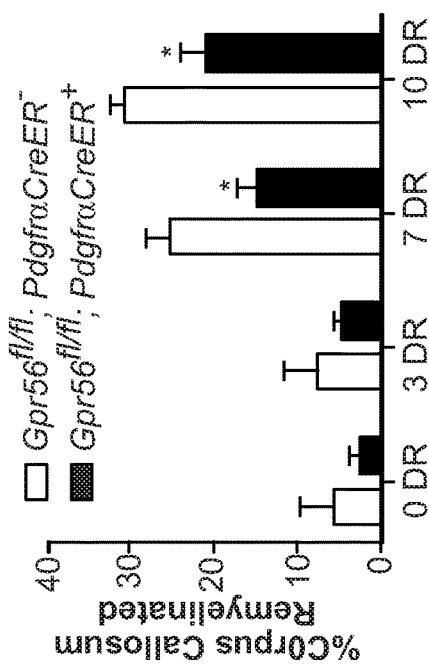
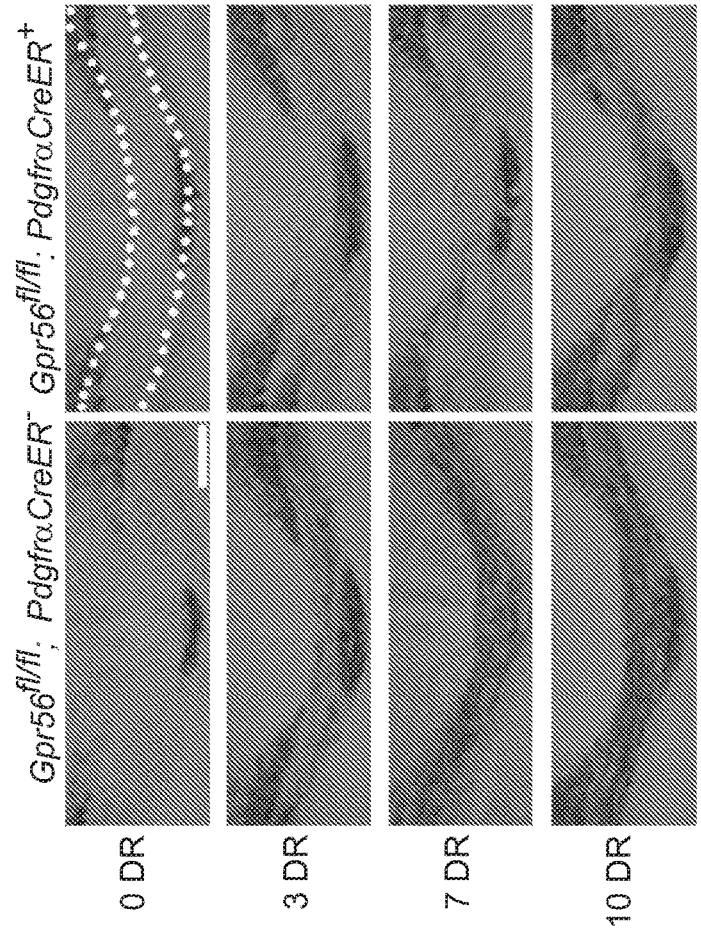
FIG. 12A
FIG. 12B

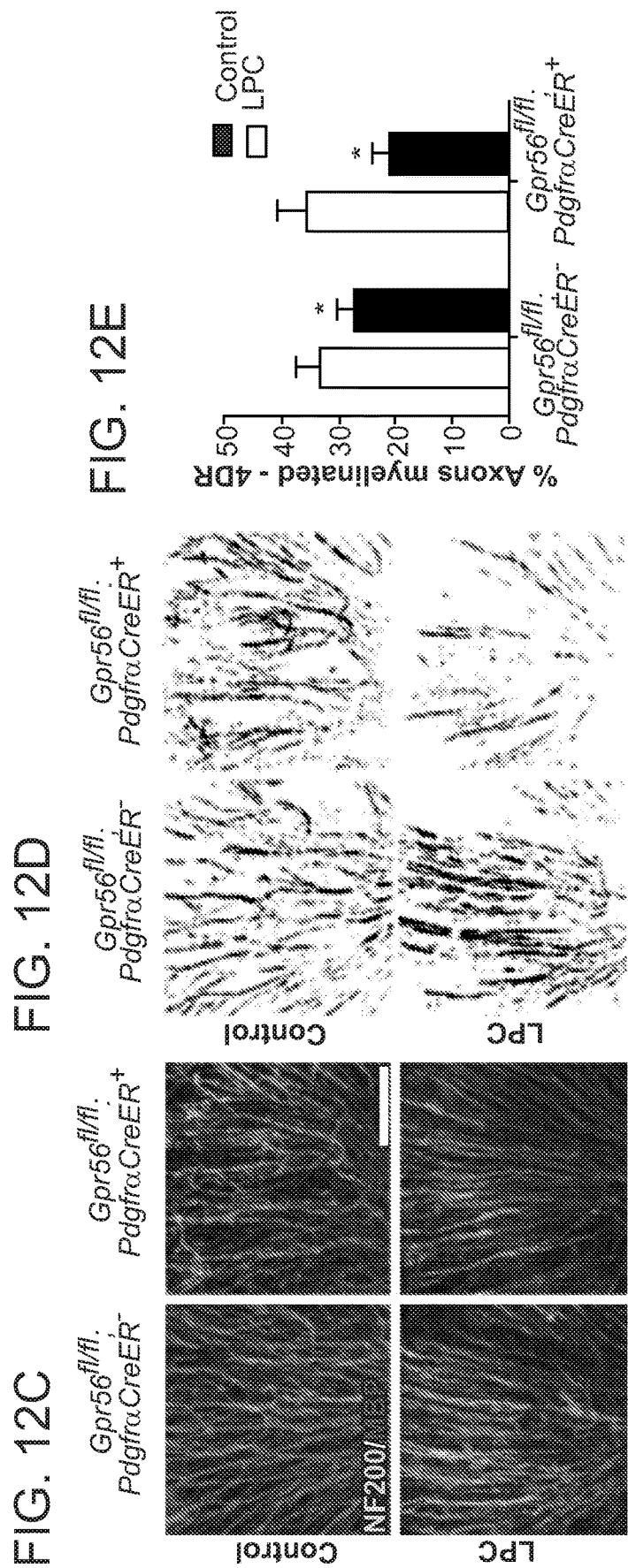

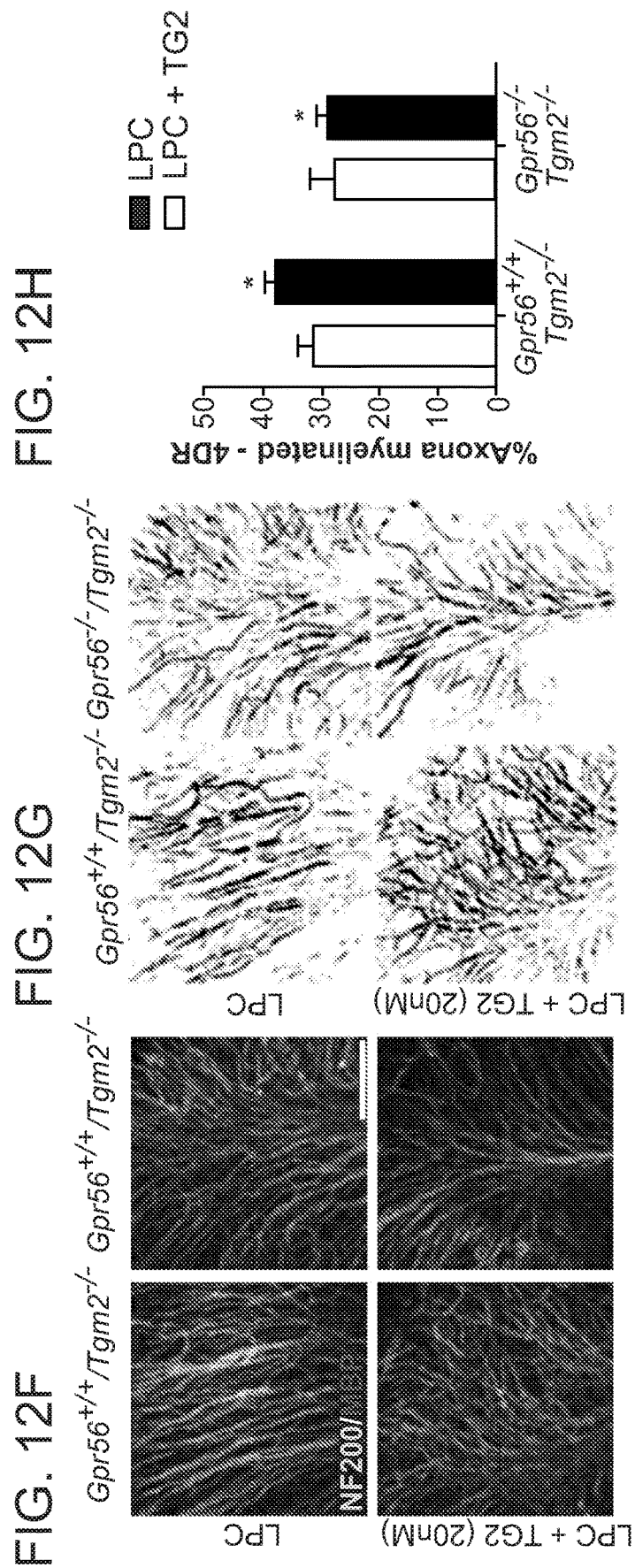

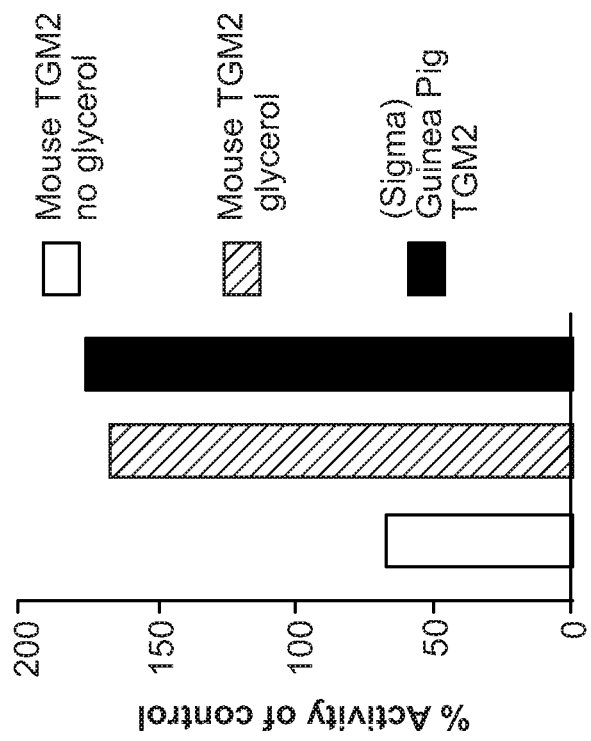
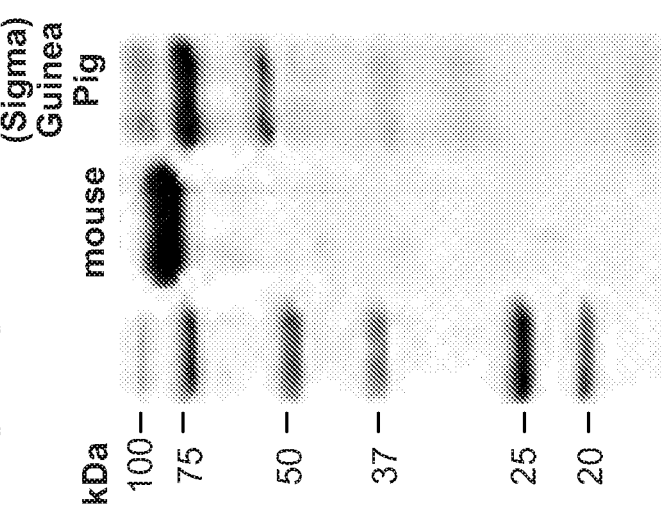
FIG. 15B
FIG. 15A

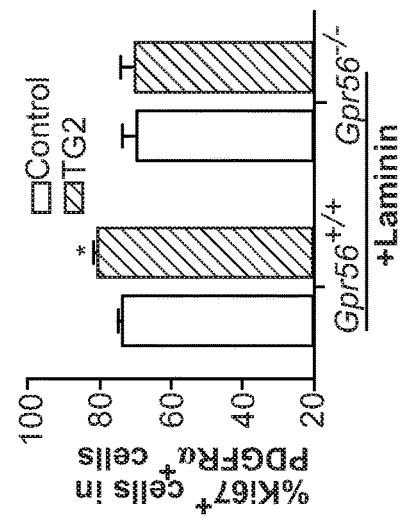
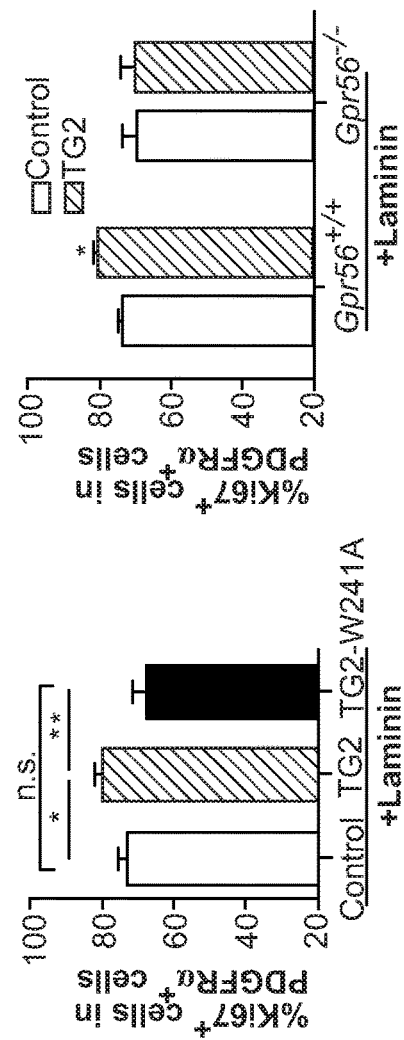
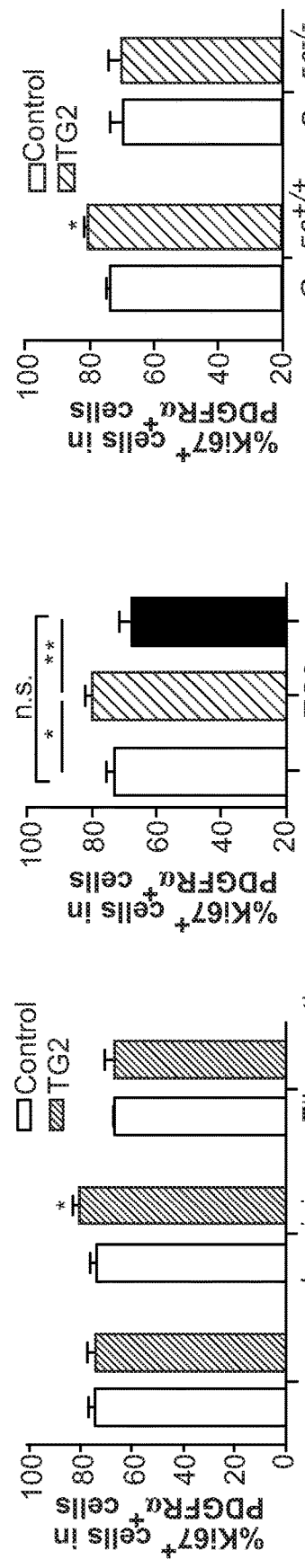
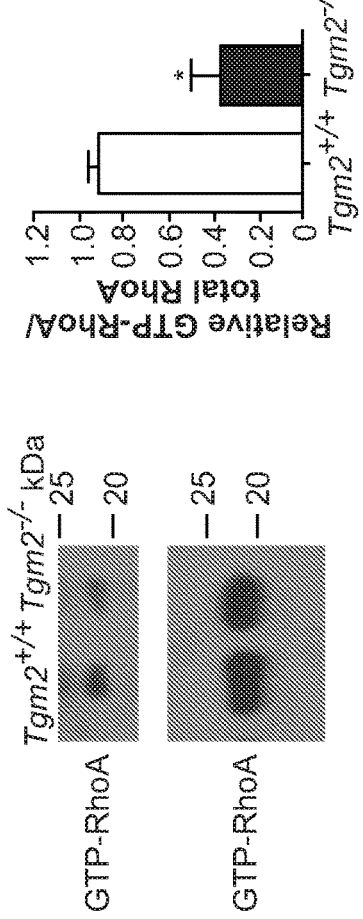
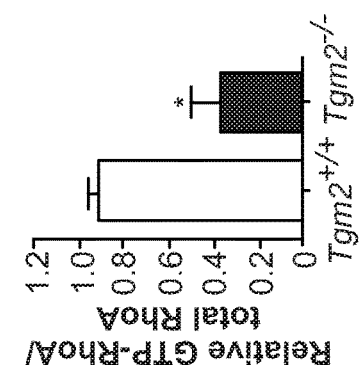
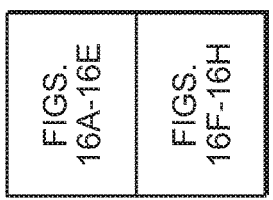
FIG. 16

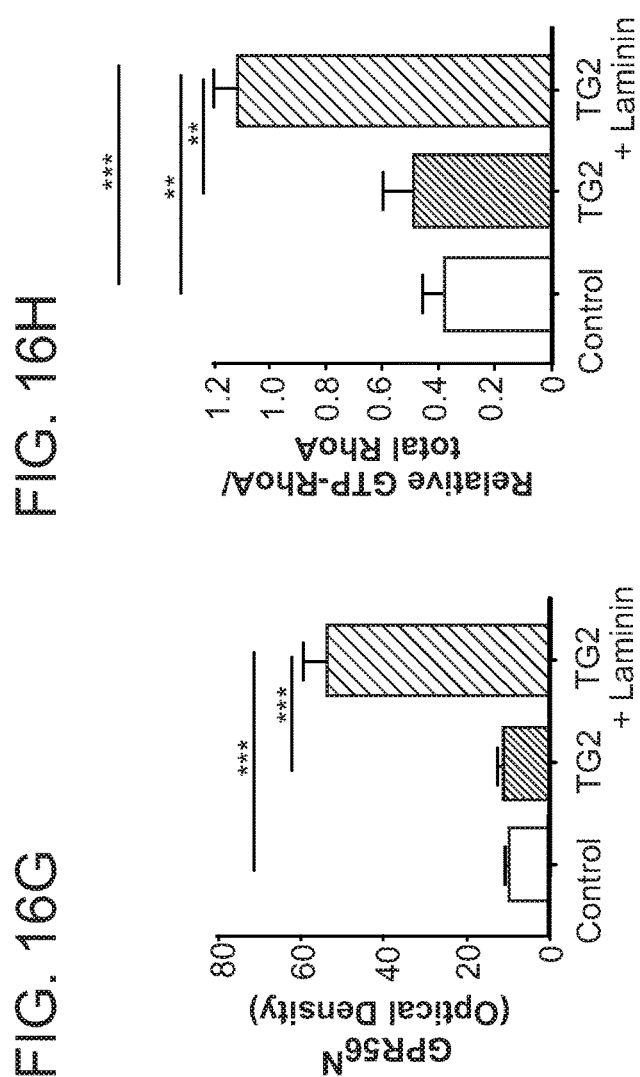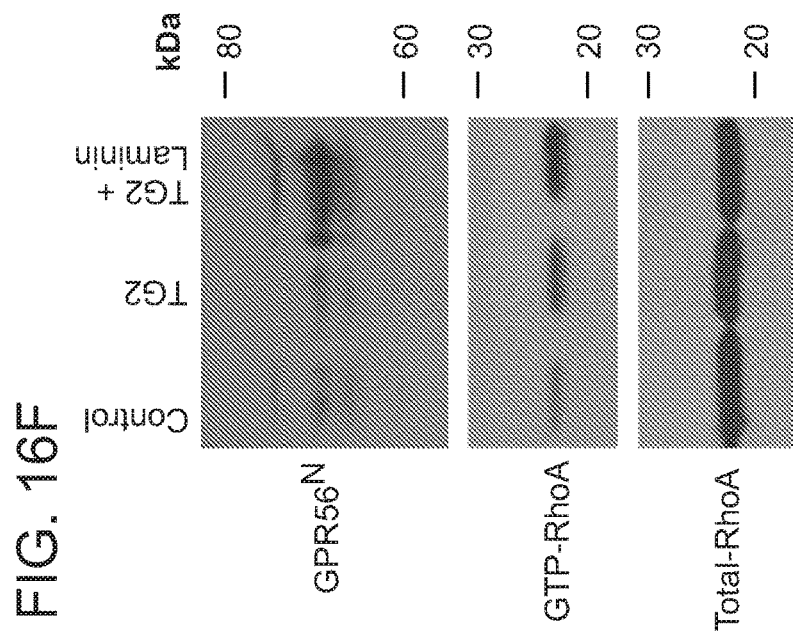

SEQUENCE LISTING

```
<160> NUMBER OF SEQ ID NOS: 41

<210> SEQ ID NO 1
<211> LENGTH: 9
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 1

Thr Tyr Phe Ala Val Leu Met Val Ser
1               5

<210> SEQ ID NO 2
<211> LENGTH: 22
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Thr Tyr Phe Ala Val Leu Met Val Ser Ser Val Glu Val Asp Ala Val
1               5                   10                  15

His Lys His Tyr Leu Ser
            20

<210> SEQ ID NO 3
<211> LENGTH: 687
<212> TYPE: PRT
<213> ORGANISM: Homo sapiens

<400> SEQUENCE: 3

Met Ala Glu Glu Leu Val Leu Glu Arg Cys Asp Leu Glu Leu Glu Thr
1               5                   10                  15

Asn Gly Arg Asp His His Thr Ala Asp Leu Cys Arg Glu Lys Leu Val
                20                  25                  30

Val Arg Arg Gly Gln Pro Phe Trp Leu Thr Leu His Phe Glu Gly Arg
            35                  40                  45

Asn Tyr Glu Ala Ser Val Asp Ser Leu Thr Phe Ser Val Val Thr Gly
        50                  55                  60

Pro Ala Pro Ser Gln Glu Ala Gly Thr Lys Ala Arg Phe Pro Leu Arg
65                  70                  75                  80

Asp Ala Val Glu Glu Gly Asp Trp Thr Ala Thr Val Val Asp Gln Gln
                85                  90                  95

Asp Cys Thr Leu Ser Leu Gln Leu Thr Thr Pro Ala Asn Ala Pro Ile
            100                 105                 110

Gly Leu Tyr Arg Leu Ser Leu Glu Ala Ser Thr Gly Tyr Gln Gly Ser
        115                 120                 125

Ser Phe Val Leu Gly His Phe Ile Leu Leu Phe Asn Ala Trp Cys Pro
    130                 135                 140

Ala Asp Ala Val Tyr Leu Asp Ser Glu Glu Glu Arg Gln Glu Tyr Val
145                 150                 155                 160

Leu Thr Gln Gln Gly Phe Ile Tyr Gln Gly Ser Ala Lys Phe Ile Lys
                165                 170                 175

Asn Ile Pro Trp Asn Phe Gly Gln Phe Glu Asp Gly Ile Leu Asp Ile
            180                 185                 190

Cys Leu Ile Leu Leu Asp Val Asn Pro Lys Phe Leu Lys Asn Ala Gly
        195                 200                 205

Arg Asp Cys Ser Arg Arg Ser Ser Pro Val Tyr Val Gly Arg Val Val
    210                 215                 220

Ser Gly Met Val Asn Cys Asn Asp Asp Gln Gly Val Leu Leu Gly Arg
225                 230                 235                 240

Trp Asp Asn Asn Tyr Gly Asp Gly Val Ser Pro Met Ser Trp Ile Gly

-continued

```
            245                 250                 255
    Ser Val Asp Ile Leu Arg Arg Trp Lys Asn His Gly Cys Gln Arg Val
                260                 265                 270

Lys Tyr Gly Gln Cys Trp Val Phe Ala Ala Val Ala Cys Thr Val Leu
                275                 280                 285

Arg Cys Leu Gly Ile Pro Thr Arg Val Val Thr Asn Tyr Asn Ser Ala
                290                 295                 300

His Asp Gln Asn Ser Asn Leu Leu Ile Glu Tyr Phe Arg Asn Glu Phe
    305                 310                 315                 320

Gly Glu Ile Gln Gly Asp Lys Ser Glu Met Ile Trp Asn Phe His Cys
                    325                 330                 335

Trp Val Glu Ser Trp Met Thr Arg Pro Asp Leu Gln Pro Gly Tyr Glu
                340                 345                 350

Gly Trp Gln Ala Leu Asp Pro Thr Pro Gln Glu Lys Ser Glu Gly Thr
                355                 360                 365

Tyr Cys Cys Gly Pro Val Pro Val Arg Ala Ile Lys Glu Gly Asp Leu
                370                 375                 380

Ser Thr Lys Tyr Asp Ala Pro Phe Val Phe Ala Glu Val Asn Ala Asp
    385                 390                 395                 400

Val Val Asp Trp Ile Gln Gln Asp Asp Gly Ser Val His Lys Ser Ile
                    405                 410                 415

Asn Arg Ser Leu Ile Val Gly Leu Lys Ile Ser Thr Lys Ser Val Gly
                420                 425                 430

Arg Asp Glu Arg Glu Asp Ile Thr His Thr Tyr Lys Tyr Pro Glu Gly
                435                 440                 445

Ser Ser Glu Glu Arg Glu Ala Phe Thr Arg Ala Asn His Leu Asn Lys
    450                 455                 460

Leu Ala Glu Lys Glu Thr Gly Met Ala Met Arg Ile Arg Val Gly
    465                 470                 475                 480

Gln Ser Met Asn Met Gly Ser Asp Phe Asp Val Phe Ala His Ile Thr
                485                 490                 495

Asn Asn Thr Ala Glu Glu Tyr Val Cys Arg Leu Leu Leu Cys Ala Arg
                500                 505                 510

Thr Val Ser Tyr Asn Gly Ile Leu Gly Pro Glu Cys Gly Thr Lys Tyr
                515                 520                 525

Leu Leu Asn Leu Asn Leu Glu Pro Phe Ser Glu Lys Ser Val Pro Leu
                530                 535                 540

Cys Ile Leu Tyr Glu Lys Tyr Arg Asp Cys Leu Thr Glu Ser Asn Leu
    545                 550                 555                 560

Ile Lys Val Arg Ala Leu Leu Val Glu Pro Val Ile Asn Ser Tyr Leu
                565                 570                 575

Leu Ala Glu Arg Asp Leu Tyr Leu Glu Asn Pro Glu Ile Lys Ile Arg
                580                 585                 590

Ile Leu Gly Glu Pro Lys Gln Lys Arg Lys Leu Val Ala Glu Val Ser
                595                 600                 605

Leu Gln Asn Pro Leu Pro Val Ala Leu Glu Gly Cys Thr Phe Thr Val
                610                 615                 620

Glu Gly Ala Gly Leu Thr Glu Glu Gln Lys Thr Val Glu Ile Pro Asp
    625                 630                 635                 640

Pro Val Glu Ala Gly Glu Glu Val Lys Val Arg Met Asp Leu Leu Pro
                645                 650                 655

Leu His Met Gly Leu His Lys Leu Val Val Asn Phe Glu Ser Asp Lys
                660                 665                 670
```

Leu Lys Ala Val Lys Gly Phe Arg Asn Val Ile Ile Gly Pro Ala
    675                 680                 685

<210> SEQ ID NO 4
<211> LENGTH: 3937
<212> TYPE: DNA
<213> ORGANISM: Homo sapiens

<400> SEQUENCE: 4

| | | | | | |
|---|---|---|---|---|---|
| ataagttagc | gccgctctcc | gcctcggcag | tgccagccgc | cagtggtcgc | acttggaggg | 60 |
| tctcgccgcc | agtggaagga | gccaccgccc | ccgcccgacc | atggccgagg | agctggtctt | 120 |
| agagaggtgt | gatctggagc | tggagaccaa | tggccgagac | caccacacgg | ccgacctgtg | 180 |
| ccgggagaag | ctggtggtgc | gacggggcca | gcccttctgg | ctgaccctgc | actttgaggg | 240 |
| ccgcaactac | gaggccagtg | tagacagtct | caccttcagt | gtcgtgaccg | gcccagcccc | 300 |
| tagccaggag | gccgggacca | aggcccgttt | tccactaaga | gatgctgtgg | aggagggtga | 360 |
| ctggacagcc | accgtggtgg | accagcaaga | ctgcaccctc | tcgctgcagc | tcaccacccc | 420 |
| ggccaacgcc | cccatcggcc | tgtatcgcct | cagcctggag | gcctccactg | gctaccaggg | 480 |
| atccagctttt | gtgctgggcc | acttcatttt | gctcttcaac | gcctggtgcc | agcggatgc | 540 |
| tgtgtacctg | gactcggaag | aggagcggca | ggagtatgtc | ctcacccagc | agggctttat | 600 |
| ctaccagggc | tcggccaagt | tcatcaagaa | catacccttg | g aattttgggc | agtttgaaga | 660 |
| tgggatccta | gacatctgcc | tgatccttct | agatgtcaac | cccaagttcc | tgaagaacgc | 720 |
| cggccgtgac | tgctcccgcc | gcagcagccc | cgtctacgtg | ggccgggtgg | tgagtggcat | 780 |
| ggtcaactgc | aacgatgacc | agggtgtgct | gctgggacgc | tgggacaaca | actacgggga | 840 |
| cggcgtcagc | cccatgtcct | ggatcggcag | cgtggacatc | ctgcggcgct | ggaagaacca | 900 |
| cggctgccag | cgcgtcaagt | atggccagtg | ctgggtcttc | gccgccgtgg | cctgcacagt | 960 |
| gctgaggtgc | ctgggcatcc | ctacccgcgt | cgtgaccaac | tacaactcgg | cccatgacca | 1020 |
| gaacagcaac | cttctcatcg | agtacttccg | caatgagttt | ggggagatcc | agggtgacaa | 1080 |
| gagcgagatg | atctggaact | tccactgctg | ggtggagtcg | tggatgacca | ggccggacct | 1140 |
| gcagccgggg | tacgagggct | ggcaggccct | ggacccaacg | ccccaggaga | gagcgaagg | 1200 |
| gacgtactgc | tgtggcccag | ttccagttcg | tgccatcaag | gagggcgacc | tgagcaccaa | 1260 |
| gtacgatgcg | ccctttgtct | ttgcggaggt | caatgccgac | gtggtagact | ggatccagca | 1320 |
| ggacgatggg | tctgtgcaca | aatccatcaa | ccgttccctg | atcgttgggc | tgaagatcag | 1380 |
| cactaagagc | gtgggccgag | acgagcggga | ggatatcacc | cacacctaca | aatacccaga | 1440 |
| ggggtcctca | gaggagaggg | aggccttcac | aagggcgaac | cacctgaaca | aactggccga | 1500 |
| gaaggaggag | acagggatgg | ccatgcggat | ccgtgtgggc | cagagcatga | acatgggcag | 1560 |
| tgactttgac | gtctttgccc | acatcaccaa | caacaccgct | gaggagtacg | tctgccgcct | 1620 |
| cctgctctgt | gccgcaccg | tcagctacaa | tgggatcttg | gggcccgagt | gtggcaccaa | 1680 |
| gtacctgctc | aacctcaacc | tggagccttt | ctctgagaag | agcgttcctc | tttgcatcct | 1740 |
| ctatgagaaa | taccgtgact | gccttacgga | gtccaacctc | atcaaggtgc | gggccctcct | 1800 |
| cgtggagcca | gttatcaaca | gctacctgct | ggctgagagg | gacctctacc | tggagaatcc | 1860 |
| agaaatcaag | atccggatcc | ttggggagcc | caagcagaaa | cgcaagctgg | tgctgaggt | 1920 |
| gtccctgcag | aacccgctcc | ctgtggccct | ggaaggctgc | accttcactg | tggaggggc | 1980 |
| cggcctgact | gaggagcaga | agacggtgga | gatcccagac | ccgtggagg | cagggagga | 2040 |

-continued

```
agttaaggtg agaatggacc tgctgccgct ccacatgggc ctccacaagc tggtggtgaa    2100
cttcgagagc gacaagctga aggctgtgaa gggcttccgg aatgtcatca ttggccccgc    2160
ctaagggacc cctgctccca gcctgctgag agcccccacc ttgatcccaa tccttatccc    2220
aagctagtga gcaaaatatg ccccttcttg gccccagac cccagggcag ggtgggcagc     2280 ctatggggc tctcggaaat ggaatgtgcc cctggcccat ctcagcctcc tgagcctgtg     2340
ggtccccact cacccccttt gctgtgagga atgctctgtg ccagaaacag tgggagccct    2400
gaccttggct gactggggct ggggtgagag aggaaagacc tacattccct ctcctgccca    2460
gatgcccttt ggaaagccat tgaccaccca ccatattgtt tgatctactt catagctcct    2520
tggagcaggc aaaaaaggga cagcatgccc cttggctgga tcagggaatc cagctcccta   2580
gactgcatcc cgtacctctt cccatgactg cacccagctc caggggccct tgggacagcc    2640
agagctgggt ggggacagtg ataggcccaa ggtccctcc acatcccagc agcccaagct     2700
taatagcccc cccctcaac ctcaccattg tgaagcacct actatgtgct gggtgcctcc     2760
cacacttgct ggggctcacg gggcctccaa cccatttaat caccatggga aactgttgtg    2820
ggcgctgctt ccaggataag gagactgagg cttagagaga ggaggcagcc ccctccacac    2880
cagtggcctc gtggttatta gcaaggctgg gtaatgtgaa ggcccaagag cagagtctgg    2940
gcctctgact ctgagtccac tgctccattt ataacccag cctgacctga dactgtcgga    3000
gaggctgtct ggggccttta tcaaaaaaag actcagccaa gacaaggagg tagagagggg    3060
actgggggac tggagtcag agccctggct gggttcaggt cccacgtctg gccaggcact     3120
gccttctcct ctctgggcct ttgtttcctt gttggtcaga ggagtgattg aaccagctca    3180
tctccaagga tcctctccac tccatgtttg caatgctttt atatggccca gccttgtaaa    3240
taaccacaag gtccactccc tgctccacga agccttaagc cataggccca ggatatttct    3300
gagagtgaaa ccatgactgt gaccaccttc tgtccccagc cctgtcctgg ttccttccta    3360
tgcccaggta ccacccttca gacccagtt ctaggggaga agagccctgg acacccctgc     3420 tctaccccatg agcctgcccg ctgcaatgcc tagacttccc aacagcctta gctgccagtg   3480
ctggtcacta accaacaagg ttggcacccc agctacccct tctttgcagg gctaaggccc    3540
ccaaacatag cccctgcccc ggaggaagct tggggaaccc atgagttgtc agctttgact    3600
ttatctcctg ctctttctac atgactgggc ctcccttggg ctggaagaat tgggattct    3660 ctattggagg tgagatcaca gcctccaggg ccccccaaat cccagggaag gacttggaga    3720
gaatcatgct gttgcattta gaactttctg ctttgcacag gaaagagtca cacaattaat    3780
caacatgtat attttctcta tacatagagc tctatttctc tacggtttta taaaagcctt    3840
gggttccaac caggcagtag atgtgcttct gaaccgcaag gagcaaacac tgaaataaaa    3900
tagtttattt ttcacactca aaaaaaaaaa aaaaaaa                             3937
```

<210> SEQ ID NO 5
<211> LENGTH: 687
<212> TYPE: PRT
<213> ORGANISM: Homo sapiens

<400> SEQUENCE: 5

Met Thr Pro Gln Ser Leu Leu Gln Thr Thr Leu Phe Leu Leu Ser Leu
1               5                   10                  15

Leu Phe Leu Val Gln Gly Ala His Gly Arg Gly His Arg Glu Asp Phe
            20                  25                  30

-continued

Arg Phe Cys Ser Gln Arg Asn Gln Thr His Arg Ser Ser Leu His Tyr
            35                  40                  45

Lys Pro Thr Pro Asp Leu Arg Ile Ser Ile Glu Asn Ser Glu Ala
 50                  55                  60

Leu Thr Val His Ala Pro Phe Pro Ala Ala His Pro Ala Ser Arg Ser
 65                  70                  75                  80

Phe Pro Asp Pro Arg Gly Leu Tyr His Phe Cys Leu Tyr Trp Asn Arg
                 85                  90                  95

His Ala Gly Arg Leu His Leu Leu Tyr Gly Lys Arg Asp Phe Leu Leu
             100                 105                 110

Ser Asp Lys Ala Ser Ser Leu Leu Cys Phe Gln His Gln Glu Glu Ser
             115                 120                 125

Leu Ala Gln Gly Pro Pro Leu Leu Ala Thr Ser Val Thr Ser Trp Trp
 130                 135                 140

Ser Pro Gln Asn Ile Ser Leu Pro Ser Ala Ala Ser Phe Thr Phe Ser
145                 150                 155                 160

Phe His Ser Pro Pro His Thr Ala Ala His Asn Ala Ser Val Asp Met
                 165                 170                 175

Cys Glu Leu Lys Arg Asp Leu Gln Leu Leu Ser Gln Phe Leu Lys His
             180                 185                 190

Pro Gln Lys Ala Ser Arg Arg Pro Ser Ala Ala Pro Ala Ser Gln Gln
             195                 200                 205

Leu Gln Ser Leu Glu Ser Lys Leu Thr Ser Val Arg Phe Met Gly Asp
 210                 215                 220

Met Val Ser Phe Glu Glu Asp Arg Ile Asn Ala Thr Val Trp Lys Leu
225                 230                 235                 240

Gln Pro Thr Ala Gly Leu Gln Asp Leu His Ile His Ser Arg Gln Glu
                 245                 250                 255

Glu Glu Gln Ser Glu Ile Met Glu Tyr Ser Val Leu Leu Pro Arg Thr
             260                 265                 270

Leu Phe Gln Arg Thr Lys Gly Arg Ser Gly Glu Ala Glu Lys Arg Leu
             275                 280                 285

Leu Leu Val Asp Phe Ser Ser Gln Ala Leu Phe Gln Asp Lys Asn Ser
 290                 295                 300

Ser Gln Val Leu Gly Glu Lys Val Leu Gly Ile Val Val Gln Asn Thr
305                 310                 315                 320

Lys Val Ala Asn Leu Thr Glu Pro Val Val Leu Thr Phe Gln His Gln
                 325                 330                 335

Leu Gln Pro Lys Asn Val Thr Leu Gln Cys Val Phe Trp Val Glu Asp
             340                 345                 350

Pro Thr Leu Ser Ser Pro Gly His Trp Ser Ser Ala Gly Cys Glu Thr
             355                 360                 365

Val Arg Arg Glu Thr Gln Thr Ser Cys Phe Cys Asn His Leu Thr Tyr
 370                 375                 380

Phe Ala Val Leu Met Val Ser Ser Val Glu Val Asp Ala Val His Lys
385                 390                 395                 400

His Tyr Leu Ser Leu Leu Ser Tyr Val Gly Cys Val Val Ser Ala Leu
                 405                 410                 415

Ala Cys Leu Val Thr Ile Ala Ala Tyr Leu Cys Ser Arg Arg Lys Pro
             420                 425                 430

Arg Asp Tyr Thr Ile Lys Val His Met Asn Leu Leu Leu Ala Val Phe
             435                 440                 445

Leu Leu Asp Thr Ser Phe Leu Leu Ser Glu Pro Val Ala Leu Thr Gly

```
                450           455           460
Ser Glu Ala Gly Cys Arg Ala Ser Ala Ile Phe Leu His Phe Ser Leu
465                 470                 475                 480

Leu Thr Cys Leu Ser Trp Met Gly Leu Glu Gly Tyr Asn Leu Tyr Arg
                485                 490                 495

Leu Val Val Glu Val Phe Gly Thr Tyr Val Pro Gly Tyr Leu Leu Lys
                500                 505                 510

Leu Ser Ala Met Gly Trp Gly Phe Pro Ile Phe Leu Val Thr Leu Val
                515                 520                 525

Ala Leu Val Asp Val Asp Asn Tyr Gly Pro Ile Ile Leu Ala Val His
                530                 535                 540

Arg Thr Pro Glu Gly Val Ile Tyr Pro Ser Met Cys Trp Ile Arg Asp
545                 550                 555                 560

Ser Leu Val Ser Tyr Ile Thr Asn Leu Gly Leu Phe Ser Leu Val Phe
                565                 570                 575

Leu Phe Asn Met Ala Met Leu Ala Thr Met Val Val Gln Ile Leu Arg
                580                 585                 590

Leu Arg Pro His Thr Gln Lys Trp Ser His Val Leu Thr Leu Leu Gly
                595                 600                 605

Leu Ser Leu Val Leu Gly Leu Pro Trp Ala Leu Ile Phe Phe Ser Phe
                610                 615                 620

Ala Ser Gly Thr Phe Gln Leu Val Val Leu Tyr Leu Phe Ser Ile Ile
625                 630                 635                 640

Thr Ser Phe Gln Gly Phe Leu Ile Phe Ile Trp Tyr Trp Ser Met Arg
                645                 650                 655

Leu Gln Ala Arg Gly Gly Pro Ser Pro Leu Lys Ser Asn Ser Asp Ser
                660                 665                 670

Ala Arg Leu Pro Ile Ser Ser Gly Ser Thr Ser Ser Arg Ile
                675                 680                 685

<210> SEQ ID NO 6
<211> LENGTH: 3813
<212> TYPE: DNA
<213> ORGANISM: Homo sapiens

<400> SEQUENCE: 6
agacaggcgg agcctcacct ggggctgccc gccagcccag acaagctcag actgggtgcc      60
tgtggccctg ggaggaggtg aaggggagg agcaggccac acaggcacag gccggtgagg     120
gacctgccca gacctggagg gtctcgctct gtcacacagg ctggagtgca gtggtgtgat     180
cttggctcat cgtaacctcc acctcccggg ttcaagtgat tctcatgcct cagcctcccg     240
agtagctggg attacaggtg gtgacttcca agagtgactc cgtcggagga aaatgactcc     300
ccagtcgctg ctgcagacga cactgttcct gctgagtctg ctcttcctgg tccaaggtgc     360
ccacggcagg ggccagggg aagactttcg cttctgcagc cagcggaacc agacacacag     420
gagcagcctc cactacaaac ccacaccaga cctgcgcatc tccatcgaga actccgaaga     480
ggccctcaca gtccatgccc ctttccctgc agcccaccct gcttcccgat ccttccctga     540 ccccagggg ctctaccact tctgcctcta ctggaaccga catgctggga gattacatct     600
tctctatggc aagcgtgact tcttgctgag tgacaaagcc tctagcctcc tctgcttcca     660
gcaccaggag gagagcctgg ctcagggcc ccgctgtta gccacttctg tcacctcctg     720
gtggagccct cagaacatca gcctgcccag tgccgccagc ttcaccttct ccttccacag     780
tcctccccac acggccgctc acaatgcctc ggtggacatg tgcgagctca aagggacct     840
```

```
ccagctgctc agccagttcc tgaagcatcc cagaaggcc tcaaggaggc cctcggctgc    900
ccccgccagc cagcagttgc agagcctgga gtcgaaactg acctctgtga gattcatggg    960
ggacatggtg tccttcgagg aggaccggat caacgccacg gtgtggaagc tccagcccac   1020
agccggcctc caggacctgc acatccactc ccggcaggag gaggagcaga gcgagatcat   1080
ggagtactcg gtgctgctgc ctcgaacact cttccagagg acgaaaggcc ggagcgggga   1140
ggctgagaag agactcctcc tggtggactt cagcagccaa gccctgttcc aggacaagaa   1200
ttccagccaa gtcctgggtg agaaggtctt ggggattgtg gtacagaaca ccaaagtagc   1260
caacctcacg gagcccgtgg tgctcacttt ccagcaccag ctacagccga gaatgtgac    1320
tctgcaatgt gtgttctggg ttgaagaccc cacattgagc agcccggggc attggagcag   1380
tgctgggtgt gagaccgtca ggagagaaac ccaaacatcc tgcttctgca accacttgac   1440
ctactttgca gtgctgatgg tctcctcggt ggaggtggac gccgtgcaca agcactacct   1500
gagcctcctc tcctacgtgg gctgtgtcgt ctctgccctg gctgccttg tcaccattgc    1560
cgcctacctc tgctccagga ggaaaacctcg ggactacacc atcaaggtgc acatgaacct   1620
gctgctggcc gtcttcctgc tggacacgag cttcctgctc agcgagccgg tggccctgac   1680
aggctctgag gctggctgcc gagccagtgc catcttcctg cacttctccc tgctcacctg   1740
cctttcctgg atgggcctcg aggggtacaa cctctaccga ctcgtggtgg aggtctttgg   1800
cacctatgtc cctggctacc tactcaagct gagcgccatg ggctggggct cccccatctt   1860
tctggtgacg ctggtggccc tggtggatgt ggacaactat ggccccatca tcttggctgt   1920
gcataggact ccagagggcg tcatctaccc ttccatgtgc tggatccggg actccctggt   1980
cagctacatc accaacctgg gcctcttcag cctggtgttt ctgttcaaca tggccatgct   2040
agccaccatg gtggtgcaga tcctgcggct gcgcccccac acccaaaagt ggtcacatgt   2100
gctgacactg ctgggcctca gcctggtcct tggcctgccc tgggccttga tcttcttctc   2160
cttgcttct ggcaccttcc agcttgtcgt cctctacctt ttcagcatca tcacctcctt   2220
ccaaggcttc ctcatcttca tctggtactg gtccatgcgg ctgcaggccc ggggtggccc   2280
ctcccctctg aagagcaact cagacagcgc caggctcccc atcagctcgg gcagcacctc   2340
gtccagccgc atctaggcct ccagcccacc tgcccatgtg atgaagcaga gattcggcct   2400
cgtcgcacac tgcctgtggc ccccgagccc ggccagccc caggcagtc agccgcagac   2460
tttggaaagc ccaacgacca tggagagatg ggccgttgcc atggtggacg gactcccggg   2520
ctgggctttt gaattggcct tggggactac tcggctctca ctcagctccc acggggactca   2580
gaagtgcgcc gccatgctgc ctagggtact gtccccacat ctgtcccaac ccagctggag   2640
gcctggtctc tccttacaac ccctgggccc agccctcatt gctggggcc aggccttgga   2700
tcttgagggt ctggcacatc cttaatcctg tgcccctgcc tgggacagaa atgtggctcc   2760
agttgctctg tctctcgtgg tcaccctgag ggcactctgc atcctctgtc attttaacct   2820
caggtggcac ccagggcgaa tggggcccag gcagaccctt cagggccaga gccctggcgg   2880
aggagaggcc ctttgccagg agcacagcag cagctcgcct acctctgagc ccaggccccc   2940
tccctccctc agccccccag tcctccctcc atcttccctg ggttctcct cctctcccag    3000
ggcctccttg ctccttcgtt cacagctggg ggtccccgat tccaatgctg tttttggg     3060
agtggtttcc aggagctgcc tggtgtctgc tgtaaatgtt tgtctactgc acaagcctcg   3120
gcctgcccct gagccaggct cggtaccgat gcgtgggctg ggctaggtcc ctctgtccat   3180
```

```
ctgggccttt gtatgagctg cattgcccct gctcaccctg accaagcaca cgcctcagag    3240
gggccctcag cctctcctga agccctcttg tggcaagaac tgtggaccat gccagtcccg    3300
tctggtttcc atcccaccac tccaaggact gagactgacc tcctctggtg acactggcct    3360
agggcctgac actctcctaa gaggttctct ccaagccccc aaatagctcc aggcgccctc    3420
ggccgcccat catggttaat tctgtccaac aaacacacac gggtagattg ctggcctgtt    3480
gtaggtggta gggacacaga tgaccgacct ggtcactcct cctgccaaca ttcagtctgg    3540
tatgtgaggc gtgcgtgaag caagaactcc tggagctaca gggacaggga gccatcattc    3600
ctgcctggga atcctggaag acttcctgca ggagtcagcg ttcaatcttg accttgaaga    3660
tgggaaggat gttcttttta cgtaccaatt ctttttgtctt ttgatattaa aaagaagtac    3720
atgttcattg tagagaattt ggaaactgta gaagagaatc aagaagaaaa ataaaaatca    3780
gctgttgtaa tcacctagca aactggcgta agc                                3813

<210> SEQ ID NO 7
<211> LENGTH: 64
<212> TYPE: DNA
<213> ORGANISM: Danio rerio

<400> SEQUENCE: 7
cccaccagtt cctgcgcaga acccgcacag ccaaccaggt gtccgtgtcc gtgtcctcgc    60
gcca                                                                 64

<210> SEQ ID NO 8
<211> LENGTH: 59
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
cccaccagtt cctgcgcaga acccgcacag caggtgtccg tgtccgtgtc ctcgcgcca     59

<210> SEQ ID NO 9
<211> LENGTH: 58
<212> TYPE: PRT
<213> ORGANISM: Danio rerio

<400> SEQUENCE: 9

Ser Val Ser Ser Arg Gln Ala His Gln Phe Leu Arg Arg Thr Arg Arg
1               5                   10                  15

Ala Asn Gln Val Phe Glu Glu Thr Lys Gln Gly His Leu Glu Arg Glu
            20                  25                  30

Cys Val Glu Glu Lys Cys Thr Lys Glu Glu Ala Arg Glu Val Phe Glu
        35                  40                  45

Asn Asp Pro Glu Thr Glu Tyr Phe Tyr Pro
    50                  55

<210> SEQ ID NO 10
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ser Val Ser Ser Arg Gln Ala His Gln Phe Leu Arg Arg Thr Arg Arg
```

```
            1               5                  10                  15
Ala Gly Val Arg Val Leu Ala Pro Gly Pro Pro Val Pro Ala Gln Asn
                20                  25                  30

Pro Gln Ser Gln Pro Gly Val Arg Gly Asp Gln Thr Gly Pro Pro Gly
        35                  40                  45

Glu Gly Val Cys Gly Gly Glu Val His
    50                  55

<210> SEQ ID NO 11
<211> LENGTH: 61
<212> TYPE: DNA
<213> ORGANISM: Danio rerio

<400> SEQUENCE: 11
aggatgttaa gctggaggcg gttcaaagta ataataacgt ggagctagtg agtgagatcc      60
t                                                                     61

<210> SEQ ID NO 12
<211> LENGTH: 60
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
aggatgttaa gctggaggcg gttcaaagta ataataacgg gagctagtga gtgagatcct      60

<210> SEQ ID NO 13
<211> LENGTH: 58
<212> TYPE: PRT
<213> ORGANISM: Danio rerio

<400> SEQUENCE: 13

Asp Val Lys Leu Glu Ala Val Gln Ser Asn Asn Val Glu Leu Val Ser
1               5                   10                  15

Glu Ile Leu Ser Asp Met Ser Ser Leu Ile Ile Arg Asp Glu Ser Ala
                20                  25                  30

Ala Glu Leu Ser Asn Ile Leu Lys Glu Pro His Phe Gln Ser Leu Leu
        35                  40                  45

Glu Ala His Asp Lys Val Ala Ser Lys Ser
    50                  55

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Val Lys Leu Glu Ala Val Gln Ser Asn Lys Gly Ser
1               5                   10

<210> SEQ ID NO 15
<211> LENGTH: 58
<212> TYPE: DNA
<213> ORGANISM: Danio rerio

<400> SEQUENCE: 15
tctctgtgtt tgttcagcta tgcagcaggt gttggataac ctgggcgagt tgccctcc       58
```

```
<210> SEQ ID NO 16
<211> LENGTH: 52
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
tctctgtgtt tgttcagcta tgcagcaggt gttggagggc gagttgccct cc          52

<210> SEQ ID NO 17
<211> LENGTH: 58
<212> TYPE: PRT
<213> ORGANISM: Danio rerio

<400> SEQUENCE: 17

Met Ile Thr Ala Met Gln Gln Val Leu Asp Asn Leu Gly Glu Leu Pro
1               5                   10                  15

Ser Thr Thr Gly Ala Lys Asp Ile Asp Leu Ile Phe Leu Lys Gly Ile
            20                  25                  30

Met Glu Ser Pro Ile Val Arg Ser Leu Ala Lys Ala His Glu Arg Leu
        35                  40                  45

Glu Asp Val Lys Leu Glu Ala Val Gln Glu
    50                  55

<210> SEQ ID NO 18
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Ile Thr Ala Met Gln Gln Val Leu Glu Gly Glu Leu Pro Ser Thr
1               5                   10                  15

Thr Gly Ala Lys Asp Ile Asp Leu Ile Phe Leu Lys Gly Ile Met Glu
            20                  25                  30

Ser Pro Ile Val Arg Ser Leu Ala Lys Ala His Glu Arg Leu Glu Asp
        35                  40                  45

Val Lys Leu Glu Ala Val Gln Glu
    50                  55

<210> SEQ ID NO 19
<211> LENGTH: 58
<212> TYPE: DNA
<213> ORGANISM: Danio rerio

<400> SEQUENCE: 19
gaaacataag aagaagaagg aaaaactagg gaataagact gaggaagagg acgaaaag    58

<210> SEQ ID NO 20
<211> LENGTH: 38
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
gaaacataag aagaagaagt gaggaagagg acgaaaag                          38
```

<210> SEQ ID NO 21
<211> LENGTH: 58
<212> TYPE: PRT
<213> ORGANISM: Danio rerio

<400> SEQUENCE: 21

Lys His Lys Lys Lys Glu Lys Leu Gly Asn Lys Thr Glu Glu Glu
1               5                   10                  15

Asp Glu Lys Lys Glu Gly Lys Asp Glu Asn Lys Glu Gly Lys Glu
            20                  25                  30

Glu Lys Thr Ile Thr Val Arg Lys Arg Asn Lys Lys His Leu Lys Val
        35                  40                  45

Thr Ile Ala Pro Gly Thr Val Thr Ser Ala
    50                  55

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Lys His Lys Lys Lys Lys
1               5

<210> SEQ ID NO 23
<211> LENGTH: 58
<212> TYPE: DNA
<213> ORGANISM: Danio rerio

<400> SEQUENCE: 23
gatggacata acctgatctc cctcctggag gtcctctctg agagacgct ggtgagtg        58

<210> SEQ ID NO 24
<211> LENGTH: 45
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
gatggacata acctgatctc cctcctggag agacgctggt gagtg                     45

<210> SEQ ID NO 25
<211> LENGTH: 58
<212> TYPE: PRT
<213> ORGANISM: Danio rerio

<400> SEQUENCE: 25

Asp Gly His Asn Leu Ile Ser Leu Leu Glu Val Leu Ser Gly Glu Thr
1               5                   10                  15

Leu Pro Arg Glu Arg Gly Arg Met Arg Phe His Lys Leu Gln Asn Val
            20                  25                  30

Gln Ile Ala Leu Asp Phe Leu Arg His Arg Gln Val Lys Leu Val Asn
        35                  40                  45

Ile Arg Asn Asp Asp Ile Ala Asp Gly Asn
    50                  55

<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Gly His Asn Leu Ile Ser Leu Leu Glu Arg Arg Trp
1               5                   10

<210> SEQ ID NO 27
<211> LENGTH: 23
<212> TYPE: DNA
<213> ORGANISM: Danio rerio

<400> SEQUENCE: 27
cagaacccgc agagccaacc agg                                          23

<210> SEQ ID NO 28
<211> LENGTH: 23
<212> TYPE: DNA
<213> ORGANISM: Danio rerio

<400> SEQUENCE: 28
ggcggttcaa agtaataacg tgg                                          23

<210> SEQ ID NO 29
<211> LENGTH: 20
<212> TYPE: DNA
<213> ORGANISM: Danio rerio

<400> SEQUENCE: 29
gcagcaggtg ttggataacc                                              20

<210> SEQ ID NO 30
<211> LENGTH: 20
<212> TYPE: DNA
<213> ORGANISM: Danio rerio

<400> SEQUENCE: 30
aaaactaggg aataagactg                                              20

<210> SEQ ID NO 31
<211> LENGTH: 20
<212> TYPE: DNA
<213> ORGANISM: Danio rerio

<400> SEQUENCE: 31
tccctcctgg aggtcctctc                                              20

<210> SEQ ID NO 32
<211> LENGTH: 20
<212> TYPE: DNA
<213> ORGANISM: Danio rerio

<400> SEQUENCE: 32
cagaagagcg aaagtttgac                                              20

<210> SEQ ID NO 33
<211> LENGTH: 20
<212> TYPE: DNA
<213> ORGANISM: Danio rerio

```
<400> SEQUENCE: 33
cacagtgaac atcatcgagt                                              20

<210> SEQ ID NO 34
<211> LENGTH: 19
<212> TYPE: DNA
<213> ORGANISM: Danio rerio

<400> SEQUENCE: 34
acccagaggc acttgatta                                               19

<210> SEQ ID NO 35
<211> LENGTH: 20
<212> TYPE: DNA
<213> ORGANISM: Danio rerio

<400> SEQUENCE: 35
ggttccttca ggatgttaga                                              20

<210> SEQ ID NO 36
<211> LENGTH: 19
<212> TYPE: DNA
<213> ORGANISM: Danio rerio

<400> SEQUENCE: 36
ggaaatgacc tcagcagat                                               19

<210> SEQ ID NO 37
<211> LENGTH: 20
<212> TYPE: DNA
<213> ORGANISM: Danio rerio

<400> SEQUENCE: 37
catgcgttta cctcattagc                                              20

<210> SEQ ID NO 38
<211> LENGTH: 20
<212> TYPE: DNA
<213> ORGANISM: Danio rerio

<400> SEQUENCE: 38
gtggccttac atgacatctt                                              20

<210> SEQ ID NO 39
<211> LENGTH: 20
<212> TYPE: DNA
<213> ORGANISM: Danio rerio

<400> SEQUENCE: 39
ctgaatgctc acacaatcac                                              20

<210> SEQ ID NO 40
<211> LENGTH: 20
<212> TYPE: DNA
<213> ORGANISM: Danio rerio

<400> SEQUENCE: 40
gcaagtcaat ggttactggt                                              20

<210> SEQ ID NO 41
<211> LENGTH: 20
<212> TYPE: DNA
<213> ORGANISM: Danio rerio
```

```
<400> SEQUENCE: 41
gttttgacgt gggattagag                                            20
```

COMPOSITIONS AND METHODS FOR OLIGODENDROCYTE DEVELOPMENT

CROSS-REFERENCE TO RELATED APPLICATIONS

This application is the U.S. national phase application, pursuant to 35 U.S.C. § 371, of PCT International Application Ser. No.: PCT/US2017/024791, filed Mar. 29, 2017, designating the United States and published in English, which claims priority to and the benefit of U.S. Provisional Application No. 62/316,491, filed Mar. 31, 2016, the disclosures of which are incorporated herein by reference in its entirety.

STATEMENT OF RIGHTS TO INVENTIONS MADE UNDER FEDERALLY SPONSORED RESEARCH

This invention was made with government support under grant nos. R01 NS057536 and R56 NS085201 awarded by the National Institutes of Health (NIH). The government has certain rights in the invention.

SEQUENCE LISTING

The instant application contains a Sequence Listing which has been submitted electronically in ASCII format and is hereby incorporated by reference in its entirety. Said ASCII copy, created on Nov. 13, 2018, is named 167705-010201PCTSequenceListing.txt and is 32,254 bytes in size.

BACKGROUND OF THE INVENTION

Myelin sheaths cover many nerve fibers, and are composed of lipoprotein layers. Myelin is formed in early life by the oligodendrocytes in the central nervous system (CNS). Myelin promotes transmission of a neural impulse along an axon by increasing the speed at which impulses propagate along the myelinated fiber. Defects in early myelogenesis are associated with neurological defects, for example in the genetic disorder bilateral frontoparietal polymicrogyria (BFPP), which causes cortical malformation.

Demyelination in later life is also a feature of many neurologic disorders, including for example multiple sclerosis and periventricular leukodystrophy. Demyelination can result from damage to nerves or myelin due to local injury, immune response, inflammation, viral infection, hypoxia, ischemia, and/or toxic agents. Extensive myelin loss is followed by axonal and cell body degeneration, both of which may be irreversible.

At present, effective treatments and preventatives for neurological diseases and disorders characterized by defects in myelination are lacking. Accordingly, new compositions and methods of treatment are urgently required.

SUMMARY OF THE INVENTION

As described below, the present invention features compositions and methods for increasing myelination in the nervous system or a subject, including for the treatment of a disease or disorder characterized by a deficiency or loss of myelination (e.g., a demyelinating disease). Agents useful in the invention include agents or compounds that specifically bind and activate GPR56 polypeptide, including for example and without limitation, GPR56 ligands, TG2, collagen III, or active fragments thereof.

In one aspect, the invention provides a method of activating a GPR56 polypeptide on an oligodendrocyte or precursor thereof involving contacting the oligodendrocyte or precursor thereof with a transglutaminase 2 (TG2) polypeptide or fragment thereof or GPR56 ligand having amino acids 383-404 of GPR56.

In another aspect, the invention provides a method of promoting proliferation and/or differentiation of an oligodendrocyte or precursor thereof involving contacting the oligodendrocyte or precursor thereof with a transglutaminase 2 (TG2) polypeptide or fragment thereof or GPR56 ligand having amino acids 383-404 of GPR56.

In another aspect, the invention provides a method of increasing myelination in a subject involving administering to the subject a transglutaminase 2 (TG2) polypeptide or fragment thereof or GPR56 ligand having amino acids 383-404 of GPR56.

In another aspect, the invention provides a method of treating or preventing bilateral frontoparietal polymicrogyria (BFPP), including the dysmyelination associated with BFPP, in a subject involving administering to the subject a transglutaminase 2 (TG2) polypeptide or fragment thereof or GPR56 ligand having amino acids 383-404 of GPR56.

In another aspect, the invention provides a method of treating or preventing a demyelinating disease in a subject involving administering to the subject a transglutaminase 2 (TG2) polypeptide or fragment thereof or GPR56 ligand having amino acids 383-404 of GPR56.

In another aspect, the invention provides an isolated polypeptide including amino acids 381-404 of GPR56 covalently linked to a lipid or transmembrane domain.

In another aspect, the invention provides an isolated polypeptide comprising a TG2 polypeptide or fragment thereof fused to a blood-brain barrier (BBB) transport molecule. In a related aspect, the invention provides a kit containing the isolated polypeptide of any aspect delineated herein and instructions for use.

In another aspect, the invention provides a method of identifying an agent or compound that activates GPR56, the method involving contacting a cell expressing a GPR56 polypeptide with the agent, where the GPR56 polypeptide is operatively linked to a detectable reporter, where detection of a signal of the detectable report indicates that the agent or compound has GPR56 activating activity.

In various embodiments of any aspect delineated herein, the agent or compound specifically binds the GPR56 polypeptide, including for example, GPR56 ligands, TG2, collagen III, laminin (e.g., laminin-111), or active fragments thereof.

In various embodiments of any aspect delineated herein, the GPR56 ligand or polypeptide includes the amino acid sequence TYFAVLMVS (SEQ ID NO: 1). In some embodiments, the GPR56 ligand or polypeptide includes the amino acid sequence (SEQ ID NO: 2)
TYFAVLMVSSVEVDAVHKHYLS.

In various embodiments of any aspect delineated herein, the GPR56 ligand or polypeptide is covalently linked to a lipid or transmembrane domain. In certain embodiments, the N-terminus or C-terminus of the GPR56 ligand or polypeptide is covalently linked to the lipid or transmembrane domain.

In various embodiments of any aspect delineated herein, the TG2 polypeptide or fragment thereof comprises amino acids 465-687 of TG2. In certain embodiments, the TG2 polypeptide or fragment thereof forms one or more beta barrel domains.

In various embodiments of any aspect delineated herein, the TG2 polypeptide or GPR56 ligand is linked to a blood-brain barrier (BBB) transport molecule.

In various embodiments of any aspect delineated herein, the cell is an oligodendrocyte, oligodendrocyte precursor cell, or heterologous cell expressing the GPR56 polypeptide. In various embodiments of any aspect delineated herein, the oligodendrocyte or precursor thereof is in vivo or in vitro. In certain aspects, the oligodendrocyte or precursor thereof is in a subject. In various embodiments of any aspect delineated herein, the subject is a human or mammal.

In various embodiments of any aspect delineated herein, the subject has a disease or disorder characterized by a deficiency or loss of myelination (e.g., a demyelinating disease). In particular embodiments, the subject has bilateral frontoparietal polymicrogyria (BFPP). In additional embodiments, the subject has a GPR56 allele comprising a loss-of-function mutation. In certain embodiments, the transglutaminase 2 (TG2) polypeptide or fragment thereof or GPR56 ligand is administered to the subject during gestation. In various embodiments, the demyelinating disease is multiple sclerosis, periventricular leukodystrophy, periventricular leukomalacia, optic neuritis, neuromyelitis optica, acute disseminated encephalomyelitis, idiopathic inflammatory demyelinating disease, central pontine myelolysis, and progressive multifocal leukoencephalopathy.

Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988);

The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "Transglutaminase 2 (TG2) polypeptide" is meant a polypeptide or fragment thereof having at least about 85% amino acid identity to NCBI Accession No. NP_004604 and having GPR56 binding activity. An exemplary TG2 polypeptide sequence is provided below.

```
                                                           (SEQ ID NO: 3)
  1  maeelvlerc dleletngrd hhtadlcrek lvvrrgqpfw ltlhfegrny easvdsltfs 61  vvtgpapsqe agtkarfplr daveegdwta tvvdqqdctl slqlttpana piglyrlsle 121  astgyqgssf vlghfillfn awcpadavyl dseeerqeyv ltqqgfiyqg sakfiknipw 181  nfgqfedgil diclilldvn pkflknagrd csrrsspvyv grvvsgmvnc nddqgvllgr 241  wdnnygdgvs pmswigsvdi lrrwknhgcq rvkygqcwvf aavactvlrc lgiptrvvtn 301  ynsandqnsn llieyfrnef geiqgdksem iwnfhcwves wmtrpdlqpg yegwqaldpt 361  pqeksegtyc cgpvpvraik egdlstkyda pfvfaevnad vvdwiqqddg svhksinrsl 421  ivglkistks vgrderedit htykypegss eereaftran hlnklaekee tgmamrirvg 481  qsmnmgsdfd vfahitnnta eeyvcrlllc artvsyngil gpecgtkyll nlnlepfsek 541  svplcilyek yrdcltesnl ikvrallvep vinsyllaer dlylenpeik irilgepkqk 601  rklvaevslq nplpvalegc tftvegaglt eeqktveipd pveageevkv rmdllplhmg 661  lhklvvnfes dklkavkgfr nviigpa
```

By "Transglutaminase 2 (Tgm2) nucleic acid molecule" is meant a polynucleotide encoding a TGM2 polypeptide or fragment thereof. An exemplary Tgm2 nucleic acid molecule sequence is provided at NCBI Accession No. NM_004613 and is shown below.

```
                                                           (SEQ ID NO: 4)
  1  ataagttagc gccgctctcc gcctcggcag tgccagccgc cagtggtcgc acttggaggg 61  tctcgccgcc agtggaagga gccaccgccc ccgcccgacc atggccgagg agctggtctt 121  agagaggtgt gatctggagc tggagaccaa tggccgagac caccacacgg ccgacctgtg 181  ccgggagaag ctggtggtgc gacggggcca gcccttctgg ctgaccctgc actttgaggg 241  ccgcaactac gaggccagtg tagacagtct caccttcagt gtcgtgaccg gcccagcccc 301  tagccaggag gccgggacca aggcccgttt tccactaaga gatgctgtgg aggagggtga 361  ctggacagcc accgtggtgg accagcaaga ctgcaccctc tcgctgcagc tcaccacccc
```

-continued

```
 421 ggccaacgcc cccatcggcc tgtatcgcct cagcctggag gcctccactg gctaccaggg
 481 atccagcttt gtgctgggcc acttcatttt gctcttcaac gcctggtgcc cagcggatgc
 541 tgtgtacctg gactcggaag aggagcggca ggagtatgtc ctcacccagc agggctttat
 601 ctaccagggc tcggccaagt tcatcaagaa catccttgg aattttgggc agtttgaaga
 661 tgggatccta gacatctgcc tgatccttct agatgtcaac ccaagttcc tgaagaacgc
 721 cggccgtgac tgctcccgcc gcagcagccc cgtctacgtg gccgggtgg tgagtggcat
 781 ggtcaactgc aacgatgacc agggtgtgct gctgggacgc tgggacaaca actacgggga
 841 cggcgtcagc cccatgtcct ggatcggcag cgtggacatc ctgcggcgct ggaagaacca
 901 cggctgccag cgcgtcaagt atgccagtg ctgggtcttc gccgccgtgg cctgcacagt
 961 gctgaggtgc ctgggcatcc ctacccgcgt cgtgaccaac tacaactcgg cccatgacca
1021 gaacagcaac cttctcatcg agtacttccg caatgagttt ggggagatcc agggtgacaa
1081 gagcgagatg atctggaact tccactgctg ggtggagtcg tggatgacca ggccggacct
1141 gcagccgggg tacgagggct ggcaggccct ggacccaacg ccccaggaga gagcgaagg
1201 gacgtactgc tgtggcccag ttccagttcg tgccatcaag gagggcgacc tgagcaccaa
1261 gtacgatgcg ccctttgtct ttgcggaggt caatgccgac gtggtagact ggatccagca
1321 ggacgatggg tctgtgcaca aatccatcaa ccgttccctg atcgttgggc tgaagatcag
1381 cactaagagc gtgggccgag acgagcggga ggatatcacc cacacctaca atacccaga
1441 ggggtcctca gaggagaggg aggccttcac aagggcgaac cacctgaaca aactggccga
1501 gaaggaggag acagggatgg ccatgcggat ccgtgtgggc cagagcatga catgggcag
1561 tgactttgac gtctttgccc acatcaccaa caacaccgct gaggagtacg tctgccgcct
1621 cctgctctgt gcccgcaccg tcagctacaa tgggatcttg ggcccgagt gtggcaccaa
1681 gtacctgctc aacctcaacc tggagccttt ctctgagaag agcgttcctc tttgcatcct
1741 ctatgagaaa taccgtgact gccttacgga gtccaacctc atcaaggtgc gggccctcct
1801 cgtggagcca gttatcaaca gctacctgct ggctgagagg gacctctacc tggagaatcc
1861 agaaatcaag atccggatcc ttggggagcc caagcagaaa cgcaagctgg tggctgaggt
1921 gtccctgcag aacccgctcc ctgtggccct ggaaggctgc accttcactg tggaggggc
1981 cggcctgact gaggagcaga gacggtgga gatcccagac ccgtggagg caggggagga
2041 agttaaggtg agaatggacc tgctgccgct ccacatgggc ctccacaagc tggtggtgaa
2101 cttcgagagc gacaagctga aggctgtgaa gggcttccgg aatgtcatca ttggccccgc
2161 ctaagggacc cctgctccca gctgctgag agcccccacc ttgatcccaa tccttatccc
2221 aagctagtga gcaaaatatg cccttcttg ggcccagac cccagggcag ggtgggcagc
2281 ctatgggggc tctcggaaat ggaatgtgcc cctggcccat ctcagcctcc tgagcctgtg
2341 ggtccccact cacccccttt gctgtgagga atgctctgtg ccagaaacag tgggagccct
2401 gaccttggct gactggggct ggggtgagag aggaaagacc tacattccct ctcctgccca
2461 gatgcccttt ggaaagccat tgaccaccca ccatattgtt tgatctactt catagctcct
2521 tggagcaggc aaaaaaggga cagcatgccc cttggctgga tcagggaatc cagctcccta
2581 gactgcatcc cgtacctctt cccatgactg cacccagctc caggggccct tgggacagcc
2641 agagctgggt ggggacagtg ataggcccaa ggtcccctcc acatcccagc agcccaagct
2701 taatagccct cccctcaac ctcaccattg tgaagcacct actatgtgct gggtgcctcc
2761 cacacttgct ggggctcacg gggcctccaa cccatttaat caccatggga aactgttgtg
```

-continued

```
2821    ggcgctgctt ccaggataag gagactgagg cttagagaga ggaggcagcc ccctccacac
2881    cagtggcctc gtggttatta gcaaggctgg gtaatgtgaa gcccaagag cagagtctgg
2941    gcctctgact ctgagtccac tgctccattt ataacccag cctgacctga gactgtcgga
3001    gaggctgtct ggggccttta tcaaaaaaag actcagccaa gacaaggagg tagagagggg
3061    actggggga tgggagtcag agccctggct gggttcaggt cccacgtctg gccaggcact
3121    gccttctcct ctctgggcct ttgtttcctt gttggtcaga ggagtgattg aaccagctca
3181    tctccaagga tcctctccac tccatgtttg caatgctttt atatggccca gccttgtaaa
3241    taaccacaag gtccactccc tgctccacga agccttaagc cataggccca ggatatttct
3301    gagagtgaaa ccatgactgt gaccaccttc tgtccccagc cctgtcctgg ttccttccta
3361    tgcccaggta ccacccttca gacccagtt ctaggggaga agagccctgg acaccctgc
3421    tctacccatg agcctgcccg ctgcaatgcc tagacttccc aacagccta gctgccagtg
3481    ctggtcacta accaacaagg ttggcacccc agctacccct tctttgcagg gctaaggccc
3541    ccaaacatag ccctgccc ggaggaagct tggggaaccc atgagttgtc agctttgact
3601    ttatctcctg ctctttctac atgactgggc ctcccttggg ctggaagaat tggggattct
3661    ctattggagg tgagatcaca gcctccaggg cccccaaat cccagggaag gacttggaga
3721    gaatcatgct gttgcattta gaactttctg ctttgcacag gaaagagtca cacaattaat
3781    caacatgtat attttctcta tacatagagc tctatttctc tacggtttta taaaagcctt
3841    gggttccaac caggcagtag atgtgcttct gaaccgcaag gagcaaacac tgaaataaaa
3901    tagtttattt ttcacactca aaaaaaaaaa aaaaaaa
```

By "G protein-coupled receptor 56 (GPR56) polypeptide" is meant a polypeptide or fragment thereof having at least about 85% amino acid identity to NCBI Accession No. NP_004604 and having RhoA and/or mammalian target of rapamycin (mTOR) pathway signaling activity. An exemplary GPR56 polypeptide sequence is provided below.

```
  1    mtpqsllqtt lfllsllflv qgahgrghre dfrfcsqrnq thrsslhykp tpdlrisien
 61    seealtvhap fpaahpasrs fpdprglyhf clywnrhagr lhllygkrdf llsdkassll
121    cfqhqeesla qgppllatsv tswwspqnis lpsaasftfs fhspphtaah nasvdmcelk
181    rdlqllsqfl khpqkasrrp saapasqqlq slesklstvr fmgdmvsfee drinatvwkl
241    qptaglqdlh ihsrqeeeqs eimeysvllp rtlfqrtkgr sgeaekrlll vdfssqalfq
301    dknssqvlge kvlgivvqnt kvanltepvv ltfqhqlqpk nvtlqcvfwv edptlsspgh
361    wssagcetvr retqtscfcn hltyfavlmv ssvevdavhk hylsllsyvg cvvsalaclv
421    tiaaylcsrr kprdytikvh mnlllavfll dtsfllsepv altgseagcr asaiflhfsl
481    ltclswmgle gynlyrlvve vfgtyvpgyl lklsamgwgf piflvtlval vdvdnygpii
541    lavhrtpegv iypsmcwird slvsyitnlg lfslvflfnm amlatmvvqi lrlrphtqkw
601    shvltllgls lvlglpwali ffsfasgtfq lvvlylfsii tsfqgflifi wywsmrlqar
661    ggpsplksns dsarlpissg stsssri
```

By "G protein-coupled receptor 56 (GPR56) nucleic acid molecule" is meant a polynucleotide encoding a GPR56 polypeptide or fragment thereof. An exemplary GPR56 nucleic acid molecule sequence is provided at NCBI Accession No. NM_001145770 and is shown below.

(SEQ ID NO: 5)

```
   1 agacaggcgg agcctcacct ggggctgccc gccagcccag acaagctcag actgggtgcc
  61 tgtggccctg ggaggaggtg aaggggagg agcaggccac acaggcacag gccggtgagg
 121 gacctgccca gacctggagg gtctcgctct gtcacacagg ctggagtgca gtggtgtgat
 181 cttggctcat cgtaacctcc acctcccggg ttcaagtgat tctcatgcct cagcctcccg
 241 agtagctggg attacaggtg gtgacttcca agagtgactc cgtcggagga aaatgactcc
 301 ccagtcgctg ctgcagacga cactgttcct gctgagtctg ctcttcctgg tccaaggtgc
 361 ccacggcagg ggccacaggg aagactttcg cttctgcagc cagcggaacc agacacacag
 421 gagcagcctc cactacaaac ccacaccaga cctgcgcatc tccatcgaga actccgaaga
 481 ggccctcaca gtccatgccc ctttccctgc agcccaccct gcttcccgat ccttccctga
 541 ccccaggggc ctctaccact tctgcctcta ctggaaccga catgctggga gattacatct
 601 tctctatggc aagcgtgact tcttgctgag tgacaaagcc tctagcctcc tctgcttcca
 661 gcaccaggag gagagcctgg ctcagggccc ccgctgtta gccacttctg tcacctcctg
 721 gtggagccct cagaacatca gcctgcccag tgccgccagc ttcaccttct ccttccacag
 781 tcctccccac acggccgctc acaatgcctc ggtggacatg tgcgagctca aagggacct
 841 ccagctgctc agccagttcc tgaagcatcc ccagaaggcc tcaaggaggc cctcggctgc
 901 cccgccagc cagcagttgc agagcctgga gtcgaaactg acctctgtga gattcatggg
 961 ggacatggtg tccttcgagg aggaccggat caacgccacg gtgtggaagc tccagcccac
1021 agccggcctc caggacctgc acatccactc ccggcaggag gaggagcaga gcgagatcat
1081 ggagtactcg gtgctgctgc ctcgaacact cttccagagg acgaaaggcc ggagcgggga
1141 ggctgagaag agactcctcc tggtggactt cagcagccaa gccctgttcc aggacaagaa
1201 ttccagccaa gtcctgggtg agaaggtctt ggggattgtg gtacagaaca ccaaagtagc
1261 caacctcacg gagcccgtgg tgctcacttt ccagcaccag ctacagccga agaatgtgac
1321 tctgcaatgt gtgttctggg ttgaagaccc cacattgagc agcccgggc attggagcag
1381 tgctgggtgt gagaccgtca ggagagaaac ccaaacatct gcttctgca accacttgac
1441 ctactttgca gtgctgatgg tctcctcggt ggaggtggac gccgtgcaca agcactacct
1501 gagcctcctc tcctacgtgg gctgtgtcgt ctctgccctg gcctgccttg tcaccattgc
1561 cgcctacctc tgctccagga ggaaacctcg ggactacacc atcaaggtgc acatgaacct
1621 gctgctggcc gtcttcctgc tggacacgag cttcctgctc agcgagccgg tggccctgac
1681 aggctctgag gctggctgcc gagccagtgc catcttcctg cacttctccc tgctcaccct
1741 cctttcctgg atgggcctcg aggggtacaa cctctaccga ctcgtggtgg aggtcttttgg
1801 cacctatgtc cctggctacc tactcaagct gagcgccatg ggctggggct tccccatctt
1861 tctggtgacg ctggtggccc tggtggatgt ggacaactat ggccccatca tcttggctgt
1921 gcataggact ccagagggcg tcatctaccc ttccatgtgc tggatccggg actccctggt
1981 cagctacatc accaacctgg gcctcttcag cctggtgttt ctgttcaaca tggccatgct
2041 agccaccatg gtggtgcaga tcctgcggct cgcccccac acccaaaagt ggtcacatgt
2101 gctgacactg ctgggcctca gcctggtcct tggcctgccc tgggccttga tcttcttctc
2161 cttttgcttct ggcaccttcc agcttgtcgt cctctacctt ttcagcatca tcacctcctt
2221 ccaaggcttc ctcatcttca tctggtactg gtccatgcgg ctgcaggccc ggggtggccc
2281 ctcccctctg aagagcaact cagacagcgc caggctcccc atcagctcgg gcagcacctc
2341 gtccagccgc atctaggcct ccagcccacc tgcccatgtg atgaagcaga gattcggcct
```

-continued
```
2401  cgtcgcacac tgcctgtggc ccccgagccc ggcccagccc caggccagtc agccgcagac 2461  tttggaaagc ccaacgacca tggagagatg ggccgttgcc atggtggacg gactcccggg 2521  ctgggctttt gaattggcct tggggactac tcggctctca ctcagctccc acgggactca 2581  gaagtgcgcc gccatgctgc ctagggtact gtccccacat ctgtcccaac ccagctggag 2641  gcctggtctc tccttacaac ccctgggccc agccctcatt gctggggcc aggccttgga 2701  tcttgagggt ctggcacatc cttaatcctg tgccctgcc tgggacagaa atgtggctcc 2761  agttgctctg tctctcgtgg tcaccctgag ggcactctgc atcctctgtc attttaacct 2821  caggtggcac ccagggcgaa tggggcccag ggcagacctt cagggccaga gccctggcgg 2881  aggagaggcc ctttgccagg agcacagcag cagctcgcct acctctgagc ccaggccccc 2941  tccctccctc agcccccag tcctccctcc atcttccctg gggttctcct cctctcccag 3001  ggcctccttg ctccttcgtt cacagctggg ggtccccgat tccaatgctg tttttggg 3061  agtggtttcc aggagctgcc tggtgtctgc tgtaaatgtt tgtctactgc acaagcctcg 3121  gcctgcccct gagccaggct cggtaccgat gcgtgggctg ggctaggtcc ctctgtccat 3181  ctgggccttt gtatgagctg cattgcctt gctcaccctg accaagcaca cgcctcagag 3241  gggccctcag cctctcctga agccctcttg tggcaagaac tgtggaccat gccagtcccg 3301  tctggtttcc atcccaccac tccaaggact gagactgacc tcctctggtg acactggcct 3361  agggcctgac actctcctaa gaggttctct ccaagccccc aaatagctcc aggcgccctc 3421  ggccgcccat catggttaat tctgtccaac aaacacacac gggtagattg ctggcctgtt 3481  gtaggtggta gggacacaga tgaccgacct ggtcactcct cctgccaaca ttcagtctgg 3541  tatgtgaggc gtgcgtgaag caagaactcc tggagctaca gggacaggga gccatcattc 3601  ctgcctggga atcctggaag acttcctgca ggagtcagcg ttcaatcttg accttgaaga 3661  tgggaaggat gttcttttta cgtaccaatt cttttgtctt ttgatattaa aaagaagtac 3721  atgttcattg tagagaattt ggaaactgta gaagagaatc aagaagaaaa ataaaaatca 3781  gctgttgtaa tcacctagca aactggcgta agc
```

By "agent" is meant any small molecule chemical compound, antibody, nucleic acid molecule, or polypeptide, or fragments thereof.

By "alteration" or "change" is meant an increase or decrease. An alteration may be by as little as 1%, 2%, 3%, 4%, 5%, 10%, 20%, 30%, or by 40%, 50%, 60%, or even by as much as 70%, 75%, 80%, 90%, or 100%.

By "biologic sample" is meant any tissue, cell, fluid, or other material derived from an organism.

By "capture reagent" is meant a reagent that specifically binds a nucleic acid molecule or polypeptide to select or isolate the nucleic acid molecule or polypeptide.

As used herein, the terms "determining", "assessing", "assaying", "measuring" and "detecting" refer to both quantitative and qualitative determinations, and as such, the term "determining" is used interchangeably herein with "assaying," "measuring," and the like. Where a quantitative determination is intended, the phrase "determining an amount" of an analyte and the like is used. Where a qualitative and/or quantitative determination is intended, the phrase "determining a level" of an analyte or "detecting" an analyte is used.

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a protein or nucleic acid that is substantially identical to a reference protein or nucleic acid. In some embodiments the portion retains at least 50%, 75%, or 80%, or more preferably 90%, 95%, or even 99% of the biological activity of the reference protein or nucleic acid described herein.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "microglia" is meant an immune cell of the central nervous system

By "myelin" is meant a fatty white substance surrounding the axon of nerve cells and forming an electrically insulating layer. Myelination is the process by which the myelin is produced.

By "oligodendrocyte" is meant a glial cell that forms the myelin sheath of axons in the central nervous system. Oligodendrocytes differentiate from oligodendrocyte precursor cells in the central nervous system.

By "increasing proliferation" is meant increasing cell division of a cell in vivo or in vitro.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The term "subject" or "patient" refers to an animal which is the object of treatment, observation, or experiment. By way of example only, a subject includes, but is not limited to, a mammal, including, but not limited to, a human or a non-human mammal, such as a non-human primate, murine, bovine, equine, canine, ovine, or feline.

By "reference" is meant a standard of comparison or control condition. In certain embodiments, the reference is a GPR56 polypeptide or nucleic acid molecule.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95%, 96%, 97%, 98%, or even 99% or more identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "specifically binds" is meant a compound (e.g., peptide) that recognizes and binds a molecule (e.g., polypeptide), but which does not substantially recognize and bind other molecules in a sample, for example, a biological sample.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Any compounds, compositions, or methods provided herein can be combined with one or more of any of the other compositions and methods provided herein.

As used herein, the singular forms "a", "an", and "the" include plural forms unless the context clearly dictates otherwise. Thus, for example, reference to "a biomarker" includes reference to more than one biomarker.

Unless specifically stated or obvious from context, as used herein, the term "or" is understood to be inclusive.

The term "including" is used herein to mean, and is used interchangeably with, the phrase "including but not limited to."

As used herein, the terms "comprises," "comprising," "containing," "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

BRIEF DESCRIPTION OF THE DRAWINGS

FIGS. 1A-1H show that microglia express the putative ligand of GPR56. FIG. 1A shows that GPR56+ cells (gray) were adjacent to GPR56$^N$-hFc$^+$ ligand expressing cells (light gray) in P5 wt corpus callosum as examined by double labeling of GPR56 and GPR56$^N$-hFc binding in situ. DAPI, dark gray. Scale bar, 25 µm. FIG. 1B shows a higher magnification of the boxed region in FIG. 1A. Scale bar, 10 µm. FIG. 1C shows double labeling of GPR56$^N$-hFc (white) and Iba1 (gray), in P5 wt corpus callosum. DAPI, dark gray. Scale bar, 25 µm. FIG. 1D shows a higher magnification of the boxed region in FIG. 1C. Scale bar, 10 µm. FIG. 1E shows double labeling of GPR56$^N$-hFc (white) and GFAP (gray) in P5 wt corpus callosum. DAPI, dark gray. Scale bar, 25 µm. FIG. 1F shows a higher magnification of the boxed region in FIG. 1E. Scale bar, 10 µm. FIG. 1G shows double labeling of GPR56$^N$-hFc (white) and PDGFRα (gray) in P5 wt corpus callosum. DAPI, dark gray. Scale bar, 25 µm. FIG. 1H shows a higher magnification of the boxed region in FIG. 1G. Scale bar, 10 µm. Staining was repeated N=3.

FIG. 2A provides a schema of a GPR56 receptor. GPS motif, N-glycosylation sites, and GPR56$^{Ndel}$-hFc are shown. FIG. 2B provides a flow chart of the in vitro biotinylation/proteomic approach. Biotinylated GPR56$^N$-mFc was used to purify GPR56 binding partner(s) from mixed glial cell (enriched in microglia and astrocytes) lysate. Protein complexes were subjected to SDS PAGE and tryptic peptide mass spectrometry protein identification after one-step purification with immobilized streptavidin. The whole lane was excised and subjected to tryptic peptide mass spectrometry (MS) protein identification analysis.

FIGS. 3A-3I show that Collagen III (Col III) was not a ligand of GPR56 in developing white matter. FIGS. 3A-3C show double IHC for Col III (light gray) and CD31 (white) on wt P5 brains. DAPI, dark gray. Scale bar, 50 µm. FIG. 3A provides a representative image of IHC for Col III (light gray) and CD31 (white) of wt P5 brain. FIG. 3B provides a representative image of IHC for CD31 (white) of wt P5 brains. FIG. 3C provides a merged image of FIGS. 3A and 3B, showing that Col III localized with CD31 in blood vessels in the corpus callosum (CC) of P5 brains. FIG. 3D provides a cartoon of human immunoglobulin Fc tagged N-terminal domain of GPR56 (GPR56$^N$-hFc) and its mutant that has part of a Col III binding site deleted (yellow box) and no longer binds to Col III (GPR56$^{Ndel}$-hFc). FIG. 3E provides a representative image of putative ligand binding in situ with GPR56$^N$-hFc probe in the CC of P5 wt brains. FIG. 3F provides a representative image of putative ligand binding in situ with GPR56$^{Ndel}$-hFc probe in the CC of P5 wt brains. GPR56$^N$-hFc and GPR56$^{Ndel}$-hFc had a similar binding pattern in the CC. DAPI, dark gray. Scale bar, 50 µm. SVZ, subventricular zone. FIG. 3G provides a representative image of IHC for PDGFRα (light gray) on E18.5 in the CC of Col3α1$^{+/+}$ mice. DAPI, dark gray. Scale bar, 100 µm. FIG. 3H provides a representative image of IHC for PDGFRα (light gray) on E18.5 in the CC of Col3α1$^{-/-}$ mice.

DAPI, dark gray. Scale bar, 100 μm. FIG. 3I is a graph showing the density of PDGFRα+ OPCs in the CC. A comparable number of OPCs were observed in the CC of Col3a1$^{+/+}$ and Col3a1$^{-/-}$ mice. P=0.4725, unpaired t-test, N=3 per genotype.

FIGS. 4A-4O show that mutations in gas6, mpp6, and plec did not affect CNS Mbp expression. CRISPR-Cas9 technology was used to generate mutations in zebrafish gas6 (FIG. 4A), mpp6a (FIG. 4B), mpp6b (FIG. 4C), pleca (FIG. 4D), and plecb (FIG. 4E). FIG. 4A depicts a CRISPR/Cas9 system guide RNA (gRNA) designed to disrupt exon 2 (targeted sequence highlighted and SexAI restriction enzyme site used for genotyping denoted) of gas6 generated gas6$^{st1228}$, a 4 bp deletion predicted to result in a frameshift and premature STOP. Alignments of wt and mutant nucleotide sequences (top), and predicted wt (706 aa) and mutant (78 aa) protein sequences (bottom) shown. FIG. 4A discloses SEQ ID NOS 7-10, respectively, in order of appearance. FIG. 4B depicts a gRNA designed to disrupt the 3rd coding exon 5 (targeted sequence highlighted purple, and HpyCH4IV restriction enzyme site used for genotyping denoted) of mpp6a generated mpp6a$^{st1233}$, a 1 bp deletion predicted to result in a frameshift and premature STOP. Alignments of wt and mutant nucleotide sequences (top), and predicted wt (550 aa) and mutant (69 aa) protein sequences (bottom) shown. FIG. 4B discloses SEQ ID NOS 11-14, respectively, in order of appearance. FIG. 4C depicts a gRNA designed to disrupt exon 2 (targeted sequence highlighted and BstNI restriction enzyme site used for genotyping denoted) of mpp6b generated mpp6b$^{st1234}$, a 6 bp deletion predicted to result in a 2 amino acid deletion and a single amino acid change within the receptor targeting domain. Alignments of wt and mutant nucleotide sequences (top), and predicted wt (539 aa) and mutant (537 aa) protein sequences (bottom) shown. FIG. 4C discloses SEQ ID NOS 15-18, respectively, in order of appearance. FIG. 4D depicts a gRNA designed to disrupt exon 3 (targeted sequence highlighted orange, and DdeI restriction enzyme site used for genotyping denoted) of pleca generated pleca$^{st1261}$, a 20 bp deletion predicted to result in a frameshift and premature STOP. Alignments of wt and mutant nucleotide sequences (top), and predicted wt (4752 aa) and mutant (103 aa) protein sequences (bottom) shown. FIG. 4D discloses SEQ ID NOS 19-22, respectively, in order of appearance. FIG. 4E depicts a gRNA designed to disrupt the 3rd coding exon (targeted sequence highlighted yellow, and Hpy188III restriction enzyme site used for genotyping denoted) of plecb generated plecb$^{st1236}$, a 13 bp deletion predicted to result in a frameshift and premature STOP. Alignments of wt and mutant nucleotide sequences (top), and predicted wt (4530 aa) and mutant (111 aa) protein sequences (bottom) shown. FIG. 4E discloses SEQ ID NOS 23-26, respectively, in order of appearance. FIG. 4O depicts in situ hybridization of mbp in plecb$^{st1236/st'236}$ mutant larva (N=10/10). Dorsal views are shown for all images, anterior to the left. No gross changes in mbp expression were observed in putative ligand mutants relative to sibling controls.

FIGS. 5A-5Y show that mutations in in gas6, mpp6, and plec did not cause CNS myelin defects. FIG. 5A provides a representative transmission electron microscopy (TEM) image of ventral spinal cord from gas6 wt control larva (N=4) at 3 dpf. FIG. 5A provides a representative TEM image of ventral spinal cord from gas6$^{st122/st1228}$ mutant larva (N=4) at 3 dpf. FIG. 5C is a graph showing quantification of total axon number within a 196 μm$^2$ region. Quantification of total axon number revealed no significant differences between wt and gas6$^{st1228/st1228}$ mutant larvae. FIG. 5Y is a graph showing quantification of total number of myelinated axons within a 196 μm² region. Quantification of total number of myelinated axons revealed no significant differences between wt and plecb$^{st1236/st1236}$ mutant larvae. In all images, myelinated axons and sorted axons are pseudocolored. Scale, 1 μm. In FIGS. 5C-5Y, P>0.05 and data are shown as mean±s.d.

FIGS. 6A-6I show that loss of Tgm2 led to fewer mature OLs and hypomyelination in the corpus callosum (CC). FIG. 6A provides representative in situ hybridization (ISH) images of Plp (light gray) in the CC of P14 (top panel) and P28 (bottom panel) Tgm2$^{+/-}$ and Tgm2$^{-/-}$ mice. DAPI, dark gray. Scale bar, 100 μm. FIG. 6B is a graph showing quantification of Plp$^+$ oligodendrocytes. Deleting Tgm2 led to fewer mature OLs in the CC of P14 and P28. *P=0.0484; N=5 per genotype (P14); *P=0.0378; N=4 per genotype (P28), unpaired t-test. FIG. 6C provides representative transmission electron microscopy (TEM) images from P28 CC of Tgm2$^{+/+}$ and Tgm2$^{-/-}$ mice. Scale bar, 1 μm. FIG. 6D is a graph showing percentage of myelinated axons in the CC of control (Tgm2$^{+/+}$ and Tgm2$^{+/-}$) and Tgm2$^{-/-}$ mice. Deleting Tgm2 resulted in significantly fewer myelinated axons. *P=0.0299; N=3 per genotype; unpaired t-test. FIG. 6E is a scatter plot displaying g-ratio values in the CC of control and Tgm2$^{-/-}$ mice. FIG. 6F is a graph showing that average g-ratio of myelin sheath thickness was comparable in control and Tgm2$^{-/-}$ mice. P=0.728, unpaired t-test, N=3 per genotype. FIG. 6G is a plot showing the distribution of myelinated axons with respect to the axon diameter was comparable in the CC of control and Tgm2$^{-/-}$ mice. P=0.8291, two-way ANOVA, P=0.2524, Gaussian non-linear curve fit, N=3 per genotype. FIG. 6H is a plot showing axon diameter in the CC was comparable in control and Tgm2$^{-/-}$ mice. Mean±s.d.; P=0.8771; unpaired t-test; N=3 per genotype. FIG. 6I is a graph showing that the number of total axons (myelinated and unmyelinated) was comparable in the CC of control and Tgm2$^{-/-}$ mice at P28. P=0.7947, unpaired t-test, N=3 per genotype. Error bars are means±s.e.m in FIGS. 6B, 6D, and 6F-6H.

FIG. 7A provides representative images of in situ hybridization (ISH) of Plp (light gray) on P28 in the corpus callosum (CC) of Tgm2$^{+/-}$ and Tgm2$^{-/-}$ mice. DAPI, dark gray. Scale bar, 100 μm. FIG. 7B is a graph showing quantification of Plp$^+$ OLs. Quantification of Plp$^+$ OLs showed significant reduction in the number of OLs in the CC and Tgm2$^{-/-}$ mice. *P=0.0378; unpaired t-test; N=4 per genotype. FIG. 7C provides representative images of EGFP+ OLs in the CC of Plp: eGFP/Gpr56$^{+/-}$ and Plp: eGFP/Gpr56$^{-/-}$ mice on P28. DAPI, dark gray. Scale bar, 100 μm. FIG. 7D is a graph showing quantification of EGFP+ OLs. Quantification of EGFP+ OLs in the CC showed significant reduction in the CC of Gpr56$^{-/-}$ mice. *P=0.0478; unpaired t-test; N=3 per genotype. FIG. 7E provides representative images of EGFP+ OLs in the CC of Plp: eGFP/Gpr56$^{+/-}$ and Plp: eGFP/Gpr56$^{-/-}$ mice on P21. DAPI, dark gray. Scale bar, 100 μm. FIG. 7F is a graph showing quantification of EGFP+ OLs in the CC shows significant reduction in the CC of Gpr56$^{-/-}$ mice. *P=0.0314; unpaired t-test; N=3 per genotype. FIG. 7G provides representative images of in situ hybridization (ISH) of Plp (light gray) on P21 in the CC of Gpr56$^{fl/+}$; PdgfraCreER$^-$ and Gpr56$^{fl/fl}$;PdgfraCreER$^+$ mice. DAPI, dark gray. Scale bar, 100 μm. FIG. 7H is a graph showing quantification of Plp$^+$ OLs. Quantification of Plp$^+$ OLs showed significant reduction in the number of OLs in the CC of Gpr56$^{fl/fl}$; PdgfraCreER$^+$ mice. *P=0.0177, unpaired t-test, N=4 per genotype. Error bars are means±s.e.m in FIGS. 7B, 7D, 7F, and 7H.

FIG. 8A depicts a TG2 Western blot on acutely isolated microglia, OPCs, astrocytes, and mature oligodendrocytes. Microglia were the main cell source of TG2 in the P7 neonatal brain. β-actin was used as loading control. FIG. 8B provides representative in situ hybridization in situ hybridization (ISH) images of Plp (light gray) in the corpus callosum (CC) of P28 Tgm2$^{fl/+}$; Cx3cr1Cre$^-$ and Tgm2$^{fl/fl}$;Cx3cr1Cre$^+$ mice. DAPI, dark gray. Scale bar, 100 μm. FIG. 8C is a graph depicting quantification of Plp$^+$ oligodendrocytes in the CC of P28 Tgm2$^{fl/+}$;Cx3cr1Cre$^-$ and Tgm2$^{fl/fl}$;Cx3cr1Cre$^+$ mice. Deleting microglial Tgm2 led to fewer mature oligodendrocytes (OLs). **P=0.00850; N=4 per genotype, unpaired t-test. Error bars in FIG. 8C are means±s.e.m.

FIGS. 9A-9D show that deleting one allele of Tgm2 had no effect on the number of Plp$^+$ cells and myelinated axons. FIG. 9A provides representative images of in situ hybridization (ISH) of Plp on P28 in the corpus callosum (CC) in Tgm2$^{+/+}$ and Tgm2$^{+/-}$ mice. Scale bar, 100 μm. DAPI, dark gray. FIG. 9B is a graph showing quantification of Plp$^+$ oligodendrocytes in the CC. Similar numbers of oligodendrocytes (OLs) were found in the CC of Tgm2$^{+/+}$ and Tgm2$^{+/-}$ mice. *P=0.6005, unpaired t-test, N=3 per genotype. FIG. 9C provides representative TEM images from P28 CC of Tgm2$^{+/+}$ and Tgm2$^{+/-}$ mice. Scale bar, 1 µm. FIG. 9D is a graph showing percentage of myelinated axons. Percentage of myelinated axons was quantified in the CC in Tgm2$^{+/+}$ and Tgm2$^{+/-}$ mice. P=0.5129, unpaired t-test, N=3 per genotype. Error bars are means±s.e.m in FIGS. 9B and 9D.

FIGS. 10A-10J show that TG2 regulated OPC proliferation through GPR56. FIG. 10A provides representative in situ hybridization (ISH) images of Pdgfra (light gray) in the corpus callosum (CC) of P14 Tgm2$^{+/-}$ and Tgm2$^{-/-}$ mice. DAPI, dark gray. Scale bar, 100 µm. FIG. 10B is a graph showing that quantification of Pdgfrα$^-$ cells indicated fewer OPCs in the CC of Tgm2$^{-/-}$ mice. *P=0.0320, unpaired t-test, N=6 per genotype. FIG. 10C is a cartoon showing the cell cycle exit assay. FIG. 10D provides representative images of double IHC of BrdU (light gray) and Ki67 (white) in the CC of P14 Tgm2$^{+/-}$ and Tgm2$^{-/-}$ mice that were pulsed with BrdU 24 hr earlier (arrows mark double positive Ki67$^+$/BrdU$^+$ cells). DAPI, dark gray. Scale bar, 50 µm. FIG. 10E is a graph showing that the density of Ki67$^+$/BrdU$^+$ cells in the CC was lower in Tgm2$^{-/-}$ mice. *P=0.0207, unpaired t-test, N=5 per genotype.

FIG. 10F is a graph showing that the density of BrdU$^+$ cells in the CC is reduced in Tgm2$^{-/-}$ mice. **P=0.0099, unpaired t-test, N=5 per genotype. FIG. 10G provides representative images of double IHC of PDGFRα (light gray) and BrdU (white) in the CC of P14 Tgm2$^{+/-}$ and Tgm2$^{-/-}$ mice (arrows mark double positive PDGFRα$^+$/BrdU$^+$ cells). DAPI, dark gray. Scale bar, 50 µm. FIG. 10H is a graph showing that the number of BrdU$^+$/PDGFRα$^+$ cells in the CC was reduced in Tgm2$^{-/-}$ mice. *P=0.0465, unpaired t-test, N=4 per genotype. Error bars are means±s.e.m. FIG. 10I provides Western blot analyses of CDK2 in acutely isolated OPCs from P7 Tgm2$^{+/-}$ and Tgm2$^{-/-}$ brains. The bracket indicates CDK2 protein isoform bands. β-actin was used as loading control. FIG. 10J is a graph showing that CDK2 protein levels were reduced in the Tgm2$^{-/-}$ mice. **P=0.0013, unpaired t-test, N=3 per genotype. Error bars are means±s.e.m in FIGS. 10B, 10E, 10F, 10H, and 10J.

FIGS. 11A-11D show a comparable degree of reduction in the number of OPCs between Tgm2 and Gpr56 knockout mice. FIG. 11A provides representative images of in situ hybridization (ISH) of Pdgfra (light gray) on P14 in the corpus callosum (CC) of Tgm2$^{+/-}$ and Tgm2$^{-/-}$ mice. DAPI, dark gray. Scale bar, 100 µm. FIG. 11B is a graph showing quantification of Pdgfra$^+$ OPCs. Quantification of Pdgfra$^+$ OPCs revealed reduced numbers of OPCs in Tgm2$^{-/-}$ mice. *P=0.032, unpaired t-test, N=5 per genotype. FIG. 11B provides representative images of in situ hybridization (ISH) of Pdgfra (light gray) on P14 in the CC of Gpr56$^{+/-}$ and Gpr56$^{-/-}$ mice. DAPI, dark gray. Scale bar, 100 µm. FIG. 11C is a graph showing quantification of Pdgfra$^+$ OPCs. Quantification of Pdgfra$^+$ OPCs revealed reduced numbers of OPCs in Tgm2$^{-/-}$ mice. *P=0.0327, unpaired t-test, N=5 per genotype. Error bars are means±s.e.m in FIGS. 11B and 11D.

FIGS. 12A-12H show that the ligand-receptor pair of TG2 and GPR56 was required for remyelination. FIG. 12A provides representative images of Black-Gold myelin staining of the corpus callosum of Gpr56$^{fl/fl}$; PdgfrαCreER$^-$ and Gpr56$^{fl/fl}$; PdgfrαCreER$^+$ mice after cuprizone feeding for 6 weeks followed by recovery for 3 days (3 DR), 7 days (7 DR) and 10 days (10 DR) (dotted line outlines quantified region). Scale bar, 250 µm. FIG. 12B is a graph showing that percentage of remyelinated corpus callosum displayed significant decrease in myelination at 7 DR and 10 DR between Gpr56$^{fl/fl}$; PdgfrαCreER$^-$ and Gpr56$^{fl/fl}$;PdgfrαCreER$^+$ mice. *P=0.0285 (7 DR), N=4 (cre$^-$); N=4 (cre$^+$); *P=0.0416 (10 DR), N=3 (cre$^-$); N=4 (cre$^+$), unpaired t-test. FIG. 12C provides representative images of cerebellar slice cultures from P10 Gpr56$^{fl/fl}$;PdgfrαCreER$^-$ and Gpr56$^{fl/fl}$; PdgfrαCreER$^+$ mouse cerebella that were demyelinated with LPC for 24 hr followed by 4 days of remyelination (4DR). Slices were labeled with NF200 (white) and MBP (light gray); myelinated fibers appear yellow in merged images. Scale bar, 100 µm.

FIG. 12D provides composite images created in Image J showing myelinated axons (black) for quantification. FIG. 12E is a graph showing percentage of myelinated axons after remyelination. Remyelination was reduced in cerebellar slices that lacked OPC-derived GPR56. *P=0.0135, paired t-test, N=5 per genotype. FIG. 12F provides representative images of cerebellar slice cultures from P10 Gpr56$^{+/+}$; Tgm2$^{-/-}$ and Gpr56$^{-/-}$; Tgm2$^{-/-}$ mouse cerebella that were demyelinated with LPC for 24 hr followed by 4 days of remyelination in the presence or absence of TG2 (20 nM). Slices were immunostained with NF200 (white) and MBP (light gray); myelinated fibers appear yellow in merged images. Scale bar, 100 µm.

FIG. 12G provides composite images created in Image J showing myelinated axons (black) for quantification. FIG. 12H is a graph showing percentage of myelinated axons. Recombinant TG2 promotes remyelination in Gpr56$^{+/+}$; Tgm2$^{-/-}$, but not Gpr56$^{-/-}$; Tgm2$^{-/-}$ cerebellar slices. *P=0.0197, paired t-test, N=5-6 per genotype. Error bars are mean±s.e.m in FIGS. 12B, 12E, and 12H.

FIG. 14A depicts a TGM2 western blot on acutely isolated microglia, OPCs, astrocytes and oligodendrocytes. β-actin was used as loading control. FIG. 14B depicts representative images of BrdU (white) and PDGFRα (light gray) double immunostaining on OPC cultured for 24 hrs in proliferation media in the presence and absence of 2 nM recombinant TGM2. Scale bar, 100 µm. FIG. 14C depicts quantification of the percentage of BrdU$^+$ of total PDGFRα$^+$ OPCs. *P=0.0492, paired t-test, N=3 per genotype. Error bars are means±s.e.m.

FIGS. 15A and 15B depict experiments with recombinant human TGM2. FIG. 15A purified mouse recombinant TGM2 alongside Sigma Guinea Pig TGM2 by Coomassie-SDS-PAGE. FIG. 15B is a graph depicting results of an in vitro transamidation assay used to compare activities of the TGM2 preparation. Guinea Pig TGM2 was assayed based on reported activity units (Sigma).

FIGS. 16A-16H show that TG2 and laminin-111 activated a GPR56-dependent RhoA pathway and promoted OPC proliferation. FIG. 16A shows the effect of recombinant TG2 on OPC proliferation in basal condition, laminin-111 or fibronectin. TG2 stimulated OPC proliferation only in the presence of laminin-111. *P=0.039, paired t-test, N=3-6 per group. FIG. 16B shows the effect of wild type TG2 and its enzymatic dead mutant TG2-W241A proteins on OPC proliferation. Only wild type TG2 stimulated OPC proliferation. **P=0.0091; One-way ANOVA followed by Tukey post-hoc test, F(2,14)=6.7, *P=0.05 (control vs. TG2); n.s. P=0.70 (control vs. TG2-W241A); **P=0.0088 (TG2 vs. TG2-W241A). FIG. 16C shows that Gpr56$^{-/-}$ OPCs failed to respond to recombinant TG2-enhanced proliferation.

*P=0.039, paired t-test, N=6 per genotype. FIG. 16D depicts a Western blot of active RhoA (top panel) and total RhoA (bottom panel) in the corpus callosum (CC) of Tgm2$^{+/+}$ and Tgm2$^{-/-}$ mice. FIG. 16E is a graph showing that the relative level of active RhoA to total RhoA was diminished in the CC of Tgm2$^{-/-}$ mice compared to Tgm2$^{-/-}$ control mice. *P=0.0207, unpaired t-test, N=3 per genotype. FIG. 16F depicts a Western blot of GPR56$^N$ in the supernatant of HEK 293T cell culture after exposed to either TG2 or TG2+ laminin-111 (top panel), GTP-RhoA (middle panel) and total RhoA (lower panel) in HEK 293T cell pellet exposed to either TG2 or TG2+laminin-111. FIG. 16G is a graph showing that released GPR56 NTF was increased in the presence of both TG2 and laminin-111. *P=0.0002; One-way ANOVA followed by Tukey post-hoc test, F (2,6) =49.66, n.s. P=0.95 (control vs. TG2); *P=0.0003 (control vs. TG2+laminin-111); *P=0.0004 (TG2 vs. TG2+laminin-111); N=3 per treatment group. FIG. 16H is a graph showing that the relative level of GTP-RhoA to total RhoA was increased in the presence of both TG2 and laminin-111, corresponding to the increased GPR56 NTF in the supernatant. P=0.0028; One-way ANOVA followed by Tukey post-hoc test, F (2,6)=18.19, n.s. P=0.75 (control vs. TG2); P=0.0035 (control vs. TG2+laminin-111); P=0.0071 (TG2 vs. TG2+laminin-111) N=3 per treatment group. Error bars are mean±s.e.m in FIGS. 16E, 16G, and 16H.

DETAILED DESCRIPTION OF THE INVENTION

Figure 2A:
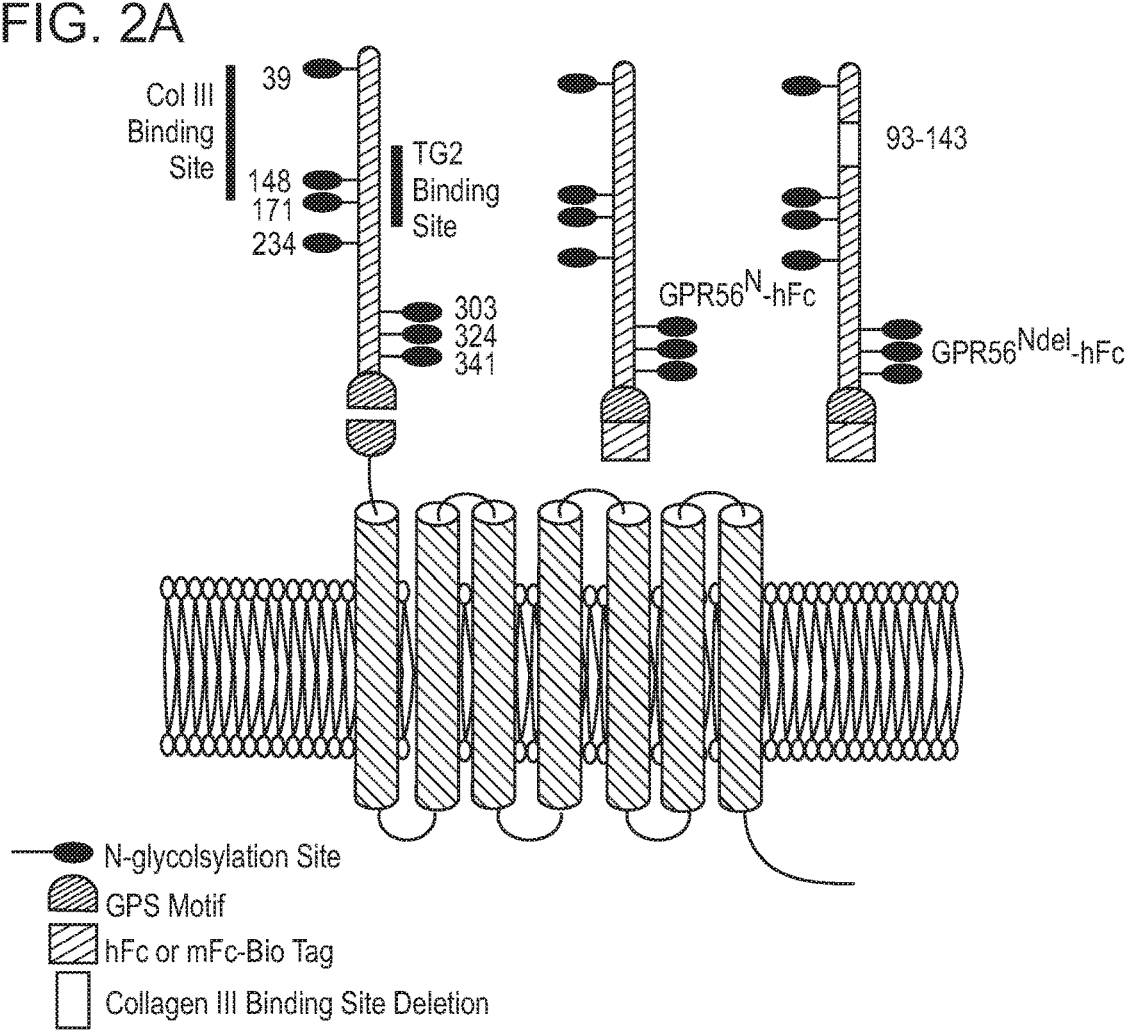
FIGS. 2A-2B provide a flow chart of the in vitro biotinylation/proteomics approach that was employed.

The invention features compositions and methods that are useful for promoting oligodendrocyte differentiation and/or proliferation and increasing myelination, as well as for the treatment and prevention of diseases or disorders characterized by a decrease or lack of oligodendrogenesis and/or myelination (e.g., bilateral frontoparietal polymicrogyria (BFPP), multiple sclerosis (MS), periventricular leukomalacia, and the like).

The present invention is based at least in part on several discoveries described herein. Using the soluble N-terminal fragment of GPR56 (GPR56$^N$), the expression of a putative ligand of GPR56 in microglia was discovered. Presenting the natural ligand was the source for an in vitro proteomics approach. Subsequent unbiased biotin-streptavidin pull down followed by mass spectrometry (MS) analysis showed that transglutaminase 2 (TG2, gene symbol Tgm2), a known binding partner of GPR56 in melanoma cells, was one of the top ligand candidates in glial cells. As described herein, TG2 interacted with GPR56 during white matter development. Deleting Tgm2 negatively impacted oligodendrocyte precursor cell (OPC) proliferation leading to a reduced number of mature oligodendrocytes (OLs) and fewer myelinated axons, mirroring the CNS myelination defect observed in Gpr56 knockout mice. TG2 is predominantly expressed in microglia. Furthermore, conditional deletion of Tgm2 in microglia recapitulate the myelination phenotype observed in global Tgm2 knockouts. Recombinant TG2 stimulated OPC proliferation in vitro in a GPR56-dependent manner. Thus, the studies described herein demonstrate that microglia-derived transglutaminase 2 (encoded by Tgm2) is the GPR56 ligand for OPCs.

In vitro, the ECM protein laminin interacts with catalytically-active TG2 to release GPR56 NTF and activates GPR56 CTF for downstream RhoA signaling, which in turn promotes OPC proliferation. In vivo, microglia-specific deletion of Tgm2 led to fewer mature oligodendrocytes (OLs) and CNS hypomyelination, phenocopying OPC-specific deficiency for GPR56. OPC-specific deletion of Gpr56 impairs CNS remyelination after cuprizone-induced demyelination, demonstrating a function with regard to repair as well as development. Recombinant TG2 rescued remyelination failure in Tgm2 knockout cerebellar slices. Taken together, these findings show that the tripartite signaling module comprised of microglial TG2-laminin-OPC GPR56 regulates OL development and myelin repair. The observed signaling of microglial TG2-laminin to GPR56 to promote OPC proliferation during developmental and reparative myelination has the potential for modulating TG2-GPR56 signaling to promote myelin repair.

Microglia and Myelination

Myelin, the multilayered glial membrane surrounding axons of jawed vertebrate animals, is important for axon conductivity and health. Myelinated axons are white in appearance, hence the "white matter" of the brain. Myelin helps to insulate the axons from electrically charged atoms and molecules. In the CNS, myelin is formed by special glial cells called oligodendrocytes (OLs) (Baumann and Pham-Dinh, *Physiological reviews* 81, 871-927, 2001; Emery, *Science* 330, 779-782, 2010). Myelination of axons is important both for efficient impulse conduction and health of nerve fibers. In the vertebrate central nervous system (CNS), myelin is made and maintained by oligodendrocytes (OLs) (Emery, Science 330, 779-782, 2010). The signals that induce oligodendrocyte precursor cells (OPCs) to proliferate and terminally differentiate into myelinating oligodendrocytes are not completely understood (Emery, Science 330, 779-782, 2010; Hughes and Appel, Curr Opin Neurobiol 39, 93-100, 2016; Mitew et al., Neuroscience 276, 29-47, 2014; Nave and Werner, Annu Rev Cell Dev Biol 30, 503-533, 2014). Other glial cell populations, including microglia, influence oligodendrocyte proliferation/maturation.

Microglia are tissue-resident microphages in the central nervous system (CNS) that originate from the hematopoietic stem cells in yolk sac (Prinz et al., Nature neuroscience 14, 1227-1235, 2011). Microglia were first described by Franz Nissl in 1880. Microglia are present in the perinatal neurogenic subventricular zone (SVZ) and nonspecific perturbation of the gut microbiome as well as microglial function by minocycline led to fewer numbers of neuroblasts and OPCs (Shigemoto-Mogami et al., J Neurosci 34, 2231-2243, 2014). Furthermore, the presence of microglia (and other macrophages), in part to clear myelin debris, is important for remyelination (Kotter et al., J Neurosci 26, 328-332, 2006). Reactive microglia are present in the vicinity of lysophosphatidylcholine (LPC) induced demyelinating lesions (Miron et al., Nature neuroscience 16, 1211-1218, 2013). The authors further identified activin-A as a microglial-derived factor that could drive OPC responses in vitro (Miron et al., Nature neuroscience 16, 1211-1218, 2013). Subsequent work by others (Dutta et al., Development 141, 2414-2428, 2014) implicated activins (but not activin-A) in myelination of the postnatal spinal cord but did not address myelin repair nor cellular sources of the activin/TGFβ signal. In summary, molecular signaling pathways that mediate communication between microglia and oligodendrocyte lineage cells during development and repair have not been delineated.

Extracellular matrix (ECM) plays a key role in development by delivering mechanical cues, independent of chemical signals (Engler et al., Cell 126, 677-689, 2006; Petersen et al., Neuron 85, 755-769, 2015; Scholz et al., Cell Rep 11, 866-874, 2015). This precept holds true for OPC proliferation and differentiation as well (Jagielska et al., Stem cells and development 21, 2905-2914, 2012; Urbanski et al., Sci Rep 6, 33751, 2016). Adhesion G protein-coupled receptors (aGPCRs), the second largest class of GPCRs in the human genome (Hamann et al., Pharmacol Rev 67, 338-367, 2015; Langenhan et al., Sci Signal 6, re3, 2013), represent plausible transducers for cellular responses to ECM. Specific aGPCRs have emerged as mechanical receptors (Langenhan et al., Nature reviews Neuroscience 17, 550-561, 2016; Petersen et al., Neuron 85, 755-769, 2015; Scholz et al., Cell Rep 11, 866-874, 2015). Structurally, aGPCRs are characterized by the presence of an extremely large N-terminal region that contains multiple conserved domains to facilitate cell-extracellular matrix (ECM) interactions. The structural basis for aGPCR-ECM signaling relies on the GPCR-Autoproteolysis-INducing (GAIN) domain that mediates autoproteolytic processing during protein maturation to generate an N- and a C-terminal fragment, NTF and CTF, respectively (Arac et al., EMBO J 31, 1364-1378, 2012; Hamann et al., Pharmacol Rev 67, 338-367, 2015; Langenhan et al., Sci Signal 6, re3, 2013). The NTF and CTF remain non-covalently associated on the cell surface (Hamann et al., Pharmacol Rev 67, 338-367, 2015; Langenhan et al., Sci Signal 6, re3, 2013; Langenhan et al., Nature reviews Neuroscience 17, 550-561, 2016). Many aGPCR members signal via a tethered agonist mechanism, in which binding of external ligands (e.g., ECM proteins) releases the NTF from its CTF and exposes the tethered agonist, resulting in robust G-protein dependent signaling (Demberg et al., Biochem Biophys Res Commun 464, 743-747, 2015; Liebscher et al., Cell Rep 9, 2018-2026, 2014; Petersen et al., Neuron 85, 755-769, 2015; Stoveken et al., Proc Natl Acad Sci USA 112, 6194-6199, 2015). Excitingly, recent research has implicated several aGPCRs in the development of myelinating glial cells in both the PNS and CNS (Ackerman et al., Nat Commun 6, 6122, 2015; Giera et al., Nat Commun 6, 6121, 2015; Langenhan et al., Nature reviews Neuroscience 17, 550-561, 2016; Monk et al., Science 325, 1402-1405, 2009; Petersen et al., Neuron 85, 755-769, 2015; Shin et al., Proc Natl Acad Sci USA 110, 19101-19106, 2013). In particular, the aGPCR GPR56/ADGRG1 regulates OL development and CNS myelination (Ackerman et al., Nat Commun 6, 6122, 2015; Giera et al., Nat Commun 6, 6121, 2015).

G Protein-Coupled Receptor 56 (GPR56)

The molecular mechanisms underlying OL development and CNS myelination are only beginning to be elucidated, and GPR56, a member of the adhesion G protein-coupled receptor family, is a recently identified novel regulator of OL development (Ackerman et al., Nat Commun 6, 6122, 2015; Giera et al. Nat Commun 6, 6121, 2015). The adhesion G protein-coupled receptor (aGPCR) GPR56/ADGRG1 is a newly identified regulator of OL development that is evolutionarily conserved in zebrafish, mice, and humans (Ackerman et al., Nat Commun 6, 6122, 2015; Giera et al., Nat Commun 6, 6121, 2015). Loss of function mutations in GPR56 cause a devastating human brain malformation termed bilateral frontoparietal polymicrogyria (BFPP) that comprises a constellation of structural brain defects including CNS hypomyelination (Piao et al., Annals of neurology 58, 680-687, 2005; Piao et al., Science 303, 2033-2036, 2004). Conditional deletion of Gpr56 in OL lineage cells showed that the hypomyelination phenotype is caused specifically by deficiency for GPR56 signaling in oligodendrocyte precursors (OPCs) and immature oligodendrocytes (OLs) (Giera et al., Nat Commun 6, 6121, 2015). Loss of Gpr56 in mice and zebrafish decreased OPC proliferation leading to a reduced number of mature myelinating OLs and fewer myelinated axons in the CNS (Ackerman et al., Nat Commun 6, 6122, 2015; Giera et al., Nat Commun 6, 6121, 2015). However, the relevant GPR56 ligand during CNS myelination was not defined during these studies.

Microglial TG2 was identified as the ligand of OPC GPR56 via a combined approach utilizing molecular, cellular and developmental biology as well as unbiased proteomics. This deorphanization is a mandatory first step in therapeutic exploitation of this novel pathway. The past few years have seen aGPCRs implicated both in CNS and peripheral nervous system myelination and myelin maintenance (Kuffer et al., Nature 536, 464-468, 2016; Langenhan et al., Nature reviews Neuroscience 17, 550-561, 2016). Although OPC-bound GPR56 was shown to be required for developmental CNS myelination (Ackerman et al., Nat Commun 6, 6122, 2015; Giera et al., Nat Commun 6, 6121, 2015; Salzman et al., Neuron 91, 1292-1304, 2016), the relevant ligand remained undefined and the role of GPR56 in myelin repair was not addressed. Here, it was demonstrated both that microglia-derived TG2 provided ligand activity for OPC-specific GPR56 during CNS myelination and that this signaling pathway was implicated in remyelination.

Figure 17:
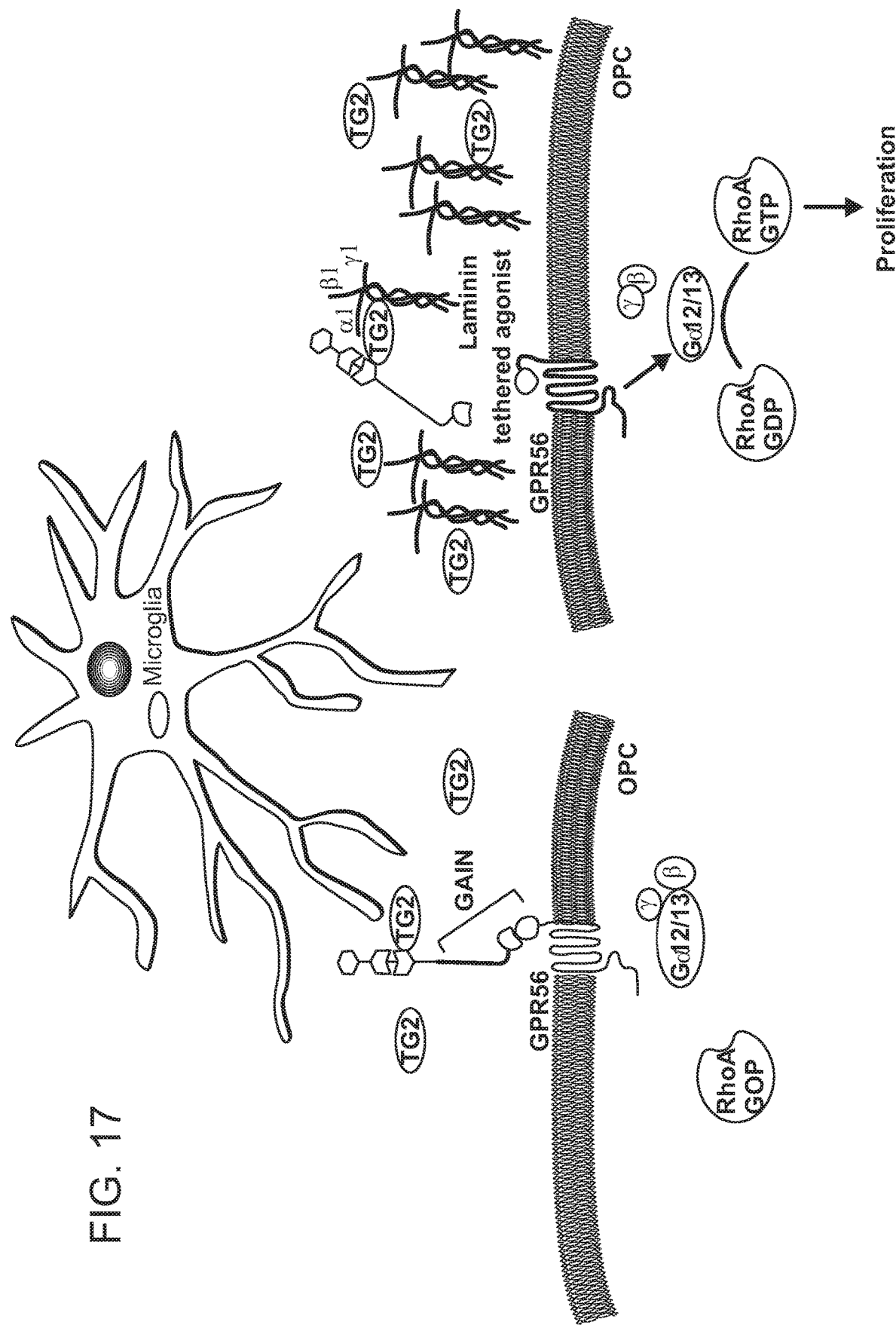
FIG. 17 shows that microglia promoted OPC proliferation via GPR56 signaling. TG2, secreted by microglia, binds GPR56 but fails to activate the receptor in the absence of ECM protein laminin-111. The binding of TG2 and laminin-111 to GPR56 leads to the dissociation of the GPR56 NTF from its CTF, allowing the tethered agonist to initiate G-protein signaling, culminating in activated RhoA, which promotes OPC proliferation. GAIN, GPCR-Autoproteolysis-INducing.

This study elucidates a novel role for microglia-ECM-OPC interactions in developmental myelination as well as remyelination. It is known that laminin regulates oligodendrogenesis and CNS myelination by interacting with integrins and dystroglycan (Colognato et al., Nat Cell Biol 4, 833-841, 2002; Colognato et al., Development 134, 1723-1736, 2007; Colognato et al., The Journal of cell biology 167, 365-375, 2004; Colognato and Tzvetanova, Developmental neurobiology 71, 924-955, 2011). In this study, a new tripartite signaling module is presented—microglial TG2, ECM laminin, and GPR56 on OPCs—that generates regulatory inputs during OL development and CNS myelination. It was previously reported that TG2 binds laminin-111 (Aeschlimann et al., J Biol Chem 267, 11316-11321, 1992). Here, it is shown that TG2, contingent on its crosslinking activity, together with laminin-111, binds to the GPR56 NTF and dissociates the NTF from the CTF, allowing the endogenous GPR56 tethered ligand to initiate G-protein signaling. Downstream RhoA activation and CDK2 are then implicated in OPC progression through the cell cycle, to generate mature oligodendrocytes (OLs) for myelination or remyelination (FIG. 17). Without being bound by theory, this microglial ligand-ECM-OPC receptor signaling triad is particularly relevant for OL development, where a complex array of factors and ECM components affect the varied stages of the process (Wheeler and Fuss, Experimental neurology 283, 512-530, 2016).

Notably, subtle dyshomeostasis could plausibly disrupt brain development (Sharon et al., Cell 167, 915-932, 2016). Loss of function mutations in GPR56 manifest a pronounced CNS hypomyelinaiton in humans (Piao et al., Annals of neurology 58, 680-687, 2005; Piao et al., Science 303, 2033-2036, 2004; Giera et al., Nat Commun 6, 6121, 2015), although both Gpr56 and Tgm2 deletion lead to a mild decrease in OL production. Without being bound by theory, this indicates that OL development is a very tightly regulated process and a minor-in-degree deviations from typical development can be phenotypically catastrophic. Perinatal white matter injury (PWMI) is another particularly salient example of derailed neurodevelopment, carries profound consequences and is characterized by heightened OPC proliferation with impaired OL maturation. Microglia upregulate Tgm2 from nil shortly after birth to high levels by 8 weeks of age (Matcovitch-Natan et al., Science 353, aad8670, 2016) with a further increase of >50-fold upon inflammatory challenge (Erny et al., Nat Neurosci 18, 965-977, 2015), potentially driving supraphysiological OPC proliferation. These studies showed that either Gpr56- or Tgm2-deficient mice exhibited normal g-ratios despite reduced oligodendrocytes (OLs) and myelinated axons. Without being bound by theory, this suggests that myelination by residual mature OLs was unimpaired, indicating a highly selective effect on OPC proliferation. Understanding the molecular regulation of perinatal dysregulation of myelin formation has the potential to accelerate rational intervention to ameliorate neurodevelopmental aberration as seen in PWMI.

Collagen III was previously identified as the ligand for neural progenitor cell-GPR56 in the developing neocortex (Luo et al., Proc Natl Acad Sci USA 108, 12925-12930, 2011). As shown herein, collagen III was not the GPR56 ligand in OPCs, and microglia-derived TG2 was the ligand of OPC-GPR56. The results of this study highlight a unique property of adhesion GPCRs: activation by distinct ligands in different cellular and developmental contexts.

The signaling module of GPR56 contains multiple potential targets for therapeutic intervention, including the GPR56-CTF, which similar to other GPCRs, serves as a legitimate drug target. Given the importance of myelin formation, maintenance and repair in neurological diseases across the human life span, these findings have the potential to provide clinical benefit for both developmental and acquired diseases of myelination.

Transglutaminase 2 (TG2)

As a member of the transglutaminase family, Transglutaminase 2 (TG2) is a versatile and multi-faceted protein that displays several diverse biological functions. In addition to the typical transamidating/crosslinking function, studies over the last decade reveal non-enzymatic functions of extracellular TG2, including promoting cell adhesion, migration, and survival[21-23]. As described herein, TG2 was identified as a regulator of OL development by serving as a ligand of GPR56. A direct mitogenic effect of TG2 on OPCs could be elicited. Without being bound to theory, thise indicates an extracellular non-enzymatic function of TG2. Further study is proposed to elucidate whether additional molecule(s) is required in this developmental regulation.

Recent literature suggests that microglia have physiological roles during the development of the central nervous system (CNS) myelination. However, the underlying molecular mechanism remains elusive. GPR56, a member of the adhesion G protein-coupled receptor family, is a recently identified novel regulator of oligodendrocyte development. The studies described herein demonstrate that microglia-derived transglutaminase 2 (encoded by Tgm2) is the GPR56 ligand for OPCs. A search for the ligand of GPR56 in the developing white matter was conducted. Using the soluble N-terminal fragment of GPR56, it was found that one or more putative ligands of GPR56 is predominantly expressed in microglia. Further biotin-streptoavidin pull-down from mixed glia cells followed by mass spectrometry analysis revealed transglutaminase 2 (TG2), a known binding partner of GPR56, as one of the top ligand candidates.

TG2 is predominantly expressed in microglia in the postnatal brain. In vitro, ECM protein laminin interacts with catalytically-active TG2 to release GPR56 NTF and activates GPR56 CTF for downstream RhoA signaling, which in turn promotes OPC proliferation. In vivo, microglia-specific deletion of Tgm2 leads to fewer mature oligodendrocytes (OLs) and CNS hypomyelination, phenocopying OPC-specific deficiency for GPR56. Tgm2 knockout mice manifest with decreased oligodendrocyte precursor cell (OPC) proliferation, leading to fewer mature oligodendrocytes and a reduced number of myelinated axons in the corpus callosum via RhoA pathway, phenocopying the Gpr56 knockout mice. Recombinant TG2 stimulated OPC proliferation in a GPR56-dependent manner in vitro. Recombinant TG2 rescued remyelination failure in Tgm2 knockout cerebellar slices. OPC-specific deletion of Gpr56 impairs CNS remyelination after cuprizone-induced demyelination, demonstrating a function with regard to repair as well as development. Thus, transglutaminase 2 (TG2, gene symbol Tgm2) was identified as a ligand for GPR56 during white matter development.

Although TG2 was reported to be present in oligodendrocyte precursors (OPCs) (Van Strien et al. Glia 59, 1622-1634, 2011) and astrocytes (Van Strien et al. *PLOS One* 6, e25037, 2011), Zhang et al. demonstrated that Tgm2 is predominantly expressed in microglia through gene expression profiling using purified glial cells and neurons (Zhang et al. *J Neurosci* 34, 11929-11947, 2014). Consistent with this observation, TG2 protein was only detected in microglia by western blot analysis. It is possible that previous reports detected the TG2 that binds to the cell surface of OPCs and astrocytes. Together, the present study demonstrates microglia-derived TG2 promotes OPC proliferation via the RhoA pathway, providing a novel molecular link on how microglia regulate OL development and CNS myelination. Taken together, the data indicate that microglial TG2 signals to GPR56 to promote OPC proliferation during developmental and reparative myelination, indicating the potential for modulating TG2-GPR56 signaling to promote myelin repair.

Methods of Treatment

The present invention provides methods of treating disease and/or disorders or symptoms thereof which comprise administering a therapeutically effective amount of a pharmaceutical composition comprising a compound of the formulae herein to a subject (e.g., a mammal such as a human). Thus, one embodiment is a method of treating a subject suffering from or susceptible to a disease or disorder or symptom thereof. The method includes the step of administering to the mammal a therapeutic amount of an amount of a compound herein sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

The increased expression or activity of GPR56 in an oligodendrocyte or precursor thereof, and/or the increased expression or activity of TG2, which is an activating ligand of GPR56, promotes myelination, decreases demyelination, and/or otherwise prevents or treats myelination deficiency or loss. The application prevents or treats neurological diseases, for example, characterized by decreased expression or activity of GPR56 (e.g., bilateral frontoparietal polymicrogyria (BFPP)). Accordingly, the invention provides for the treatment of a variety of diseases and disorders associated with decreased myelination. A demyelinating disease is a condition in which the myelin sheath which surrounds neurons in nervous tissue is lost or damaged, leading to axonal degeneration and impaired signal transduction in the affected nerves. Examples of demyelinating diseases include, without limitation, multiple sclerosis, periventricular leukodystrophy, periventricular leukomalacia, optic neuritis, neuromyelitis optica, acute disseminated encephalomyelitis, idiopathic inflammatory demyelinating disease, central pontine myelolysis, and progressive multifocal leukoencephalopathy. Demyelinating diseases are amenable to treatment by increased expression or activity of GPR56 and/or increased expression or activity of TG2.

The invention generally features method of increasing or promoting myelin formation in a subject having or at risk of developing myelin loss or deficiency. Therapies provided by the invention include polypeptide therapies and polynucleotide therapies. In on embodiment, the method involves contacting a glial cell (e.g. an oligodendrocyte or oligodendrocyte precursor) of the subject with an agonist or ligand of a GPR56 polypeptide; and activating signaling via the GPR56 polypeptide, thereby increasing or promoting myelin formation. Activating ligands of GPR56 polypeptide include naturally-occurring ligands such as TG2 or tethered ligands generated by recombinant or synthetic techniques. In another embodiment, the method involves contacting a glial cell (e.g. an oligodendrocyte or oligodendrocyte precursor) of the subject with a nucleic acid molecule encoding a GPR56 polypeptide or a fragment thereof; and expressing the GPR56 polypeptide in the cell, thereby increasing or promoting myelin formation.

The present invention provides methods of treating diseases and/or disorders or symptoms thereof related to demyelination that comprise administering a therapeutically effective amount of a pharmaceutical composition comprising an agent that increases GPR56 receptor signalling, expression, or activity to a subject (e.g., a mammal such as a human). Thus, one embodiment is a method of treating a subject suffering from or susceptible to a demyelinating disease or disorder or symptom thereof. The method includes the step of administering to the mammal a therapeutic amount of an amount of an agent herein sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect (e.g., an increase in myelination). Identifying a subject in need of such treatment can be in the judgment of a subject or a health care professional and can be subjective (e.g. opinion) or objective (e.g. measurable by a test or diagnostic method). Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The compounds herein may be also used in the treatment of any other disorders in which myelination deficiency or loss may be implicated.

Tethered Ligands

Binding of TG2 to GPR56 results in GPR56 activation via exposure of a tethered agonist, also known as the stalk region, which is inhibited by an extracellular N-terminal domain (NTD) of GPR56. The NTD is expressed as part of GPR56, proteolytically processed, and non-covalently bound to the 7 transmembrane domains of GPR56. TG2 binds the NTD domain to expose the β-strand-13/stalk region, that when exposed, serves as a tethered agonist to activate G protein signaling. (see., e.g., Stoveken et al. Proc Natl Acad Sci USA. 2015 May 12; 112 (19): 6194-6199, which is herein incorporated by reference in its entirety).

In various embodiments, the tethered agonist or GPR56 activating ligand is linked to a membrane associated moiety. Methods of making such tethered ligands are known in the art (see., e.g., U.S. Pat. Nos. 8,563,519; 6,864,229; 8,440,627; 8,389,480; and 8,354,378 and U.S. Patent Publ. Nos. 20020076755; 20060166274; 20080214451; 20030148449; 20070179090; 20090270322; and US20100137207, which are herein incorporated by reference in their entireties).

Blood-Brain Barrier (BBB) Transport

This disclosure provides compositions for delivery of an agent (e.g., a GPR56 tethered peptide, TG2 polypeptide or fragment thereof) across the blood-brain barrier (BBB) using a transporter molecule that can cross brain endothelial cells while associated with the agent. The blood-brain barrier (BBB) protects and regulates the homeostasis of the brain and prevents the free passage of molecules into most parts of the brain. Transport of essential molecules such as nutrients, growth factors and hormones is achieved via a series of specific transporters and receptors that regulate passage across the brain endothelial cells. In one embodiment an agent of the invention is fused or conjugated to a BBB peptide. BBB peptide sequences are known in the art and are described at least for example at the Brainpeps® database (brainpeps.ugent.be/; Van Dorpe et al., Brain Structure and Function, 2012, 217 (3), 687-718, which are herein incorporated by reference).

In certain aspects, a BBB transporter molecule as provided herein can bind to brain microvascular endothelial cells (BMVECs), e.g., human, and can cross through BMVEC in vitro or in vivo from the peripheral vasculature into the CNS vasculature. Whether a given fragment is a BBB-penetrable fragment can be tested by a variety of in vitro or in vivo assays known to persons of ordinary skill in the art. For example, the transporter molecule can be tested in the in vitro transcytosis assay, or in an in vivo assay such as a diuresis assay.

In certain aspects, transporter molecule activity can be demonstrated by visualization of the transporter molecule in the CNS. For example, a tritium-labeled transporter molecule can be delivered to a subject, and then visualized in the CNS via quantitative whole body radiography. In certain aspects, the transporter molecule localizes in specific regions of the CNS, e.g., the corpus callosum, developing white matter, and the like.

Recombinant Polypeptide Expression

In order to express the polypeptides of the invention, DNA molecules obtained by any of the methods described herein or those that are known in the art, can be inserted into appropriate expression vectors by techniques well known in the art. For example, a double stranded DNA can be cloned into a suitable vector by restriction enzyme linking involving the use of synthetic DNA linkers or by blunt-ended ligation. DNA ligases are usually used to ligate the DNA molecules and undesirable joining can be avoided by treatment with alkaline phosphatase.

Therefore, the invention includes vectors (e.g., recombinant plasmids) that include nucleic acid molecules (e.g., genes or recombinant nucleic acid molecules encoding genes) as described herein. The term "recombinant vector" includes a vector (e.g., plasmid, phage, phasmid, virus, cosmid, fosmid, or other purified nucleic acid vector) that has been altered, modified or engineered such that it contains greater, fewer or different nucleic acid sequences than those included in the native or natural nucleic acid molecule from which the recombinant vector was derived. For example, a recombinant vector may include a nucleotide sequence encoding a GPR56 or TG2 polypeptide, or fragment thereof, operatively linked to regulatory sequences, e.g., promoter sequences, terminator sequences, and the like, as defined herein. Recombinant vectors which allow for expression of the genes or nucleic acids included in them are referred to as "expression vectors."

In some of the molecules of the invention described herein, one or more DNA molecules having a nucleotide sequence encoding one or more polypeptides of the invention are operatively linked to one or more regulatory sequences, which are capable of integrating the desired DNA molecule into a prokaryotic host cell. Cells which have been stably transformed by the introduced DNA can be selected, for example, by introducing one or more markers which allow for selection of host cells which contain the expression vector. A selectable marker gene can either be linked directly to a nucleic acid sequence to be expressed, or be introduced into the same cell by co-transfection. Additional elements may also be needed for optimal synthesis of proteins described herein. It would be apparent to one of ordinary skill in the art which additional elements to use.

Factors of importance in selecting a particular plasmid or viral vector include, but are not limited to, the ease with which recipient cells that contain the vector are recognized and selected from those recipient cells which do not contain the vector; the number of copies of the vector which are desired in a particular host; and whether it is desirable to be able to "shuttle" the vector between host cells of different species.

Once the vector(s) is constructed to include a DNA sequence for expression, it may be introduced into an appropriate host cell by one or more of a variety of suitable methods that are known in the art, including but not limited to, for example, transformation, transfection, conjugation, protoplast fusion, electroporation, calcium phosphate-precipitation, direct microinjection, etc.

After the introduction of one or more vector(s), host cells are usually grown in a selective medium, which selects for the growth of vector-containing cells. Expression of recombinant proteins can be detected by immunoassays including Western blot analysis, immunoblot, and immunofluorescence. Purification of recombinant proteins can be carried out by any of the methods known in the art or described herein, for example, any conventional procedures involving extraction, precipitation, chromatography and electrophoresis. A further purification procedure that may be used for purifying proteins is affinity chromatography using monoclonal antibodies which bind a target protein. Generally, crude preparations containing a recombinant protein are passed through a column on which a suitable monoclonal antibody is immobilized. The protein usually binds to the column via the specific antibody while the impurities pass through. After washing the column, the protein is eluted from the gel by changing pH or ionic strength, for example.

Screening

Accordingly, the invention provides methods for identifying agents (e.g., polypeptides, polynucleotides, such as inhibitory nucleic acid molecules, antibodies, including recombinant antibodies, and small compounds) useful for increasing myelination or myelinogenesis and/or treating or preventing a disease or disorder characterized by a deficiency or loss of myelination (e.g., a demyelinating disease). Screens for the identification of such agents employ oligodendrocytes (OLs) and oligodendrocyte precursors (OPCs) according to the methods of the invention. In various embodiments, the cell may be in vitro or in vivo. The use of such cells, which express GPR56 is particularly advantageous for the identification of agents that increase GPR56 expression or biological activity. Methods of observing changes in GPR56 biological activity are exploited in high throughput assays for the purpose of identifying compounds that modulate GPR56 biological activity, e.g., transcriptional regulation or protein-nucleic acid interactions.

Any number of methods are available for carrying out screening assays to identify new candidate compounds that increase the expression or activity of GPR56 and/or TG2. In one example, candidate compounds are added at varying concentrations to the culture medium of cultured cells expressing GPR56 and/or TG2. In various embodiments, the cell is an oligodendrocyte, oligodendrocyte precursor, or heterologous cell expressing GPR56. In other embodiments, the cell is a microglial cell or heterologous cell expressing TG2. Gene expression is then measured, for example, by microarray analysis, Northern blot analysis (Ausubel et al., supra), or RT-PCR, using an appropriate hybridization probe. The level of gene expression in the presence of the candidate compound is compared to the level measured in a control culture medium lacking the candidate molecule. A compound which increases the expression of a GPR56 and/or Tgm2 gene, or a functional equivalent thereof, is considered useful in the invention; such a molecule may be used, for example, as a therapeutic to treat a human patient having a demyelination disease or disorder.

In another example, the effect of candidate compounds may be measured at the level of polypeptide production using the same general approach and standard immunological techniques, such as Western blotting or immunoprecipitation with an antibody specific for a polypeptide encoded by a GPR56 and/or Tgm2 gene. For example, immunoassays may be used to detect or monitor the expression of at least one of the polypeptides of the invention in an organism. Polyclonal or monoclonal antibodies that are capable of binding to such a polypeptide may be used in any standard immunoassay format (e.g., ELISA, Western blot, or RIA assay) to measure the level of the polypeptide. In some embodiments, a compound that promotes an increase in the expression or biological activity of the polypeptide is considered particularly useful. Again, such a molecule may be used, for example, as a therapeutic to delay, ameliorate, or treat a neoplasia in a human patient.

In yet another working example, candidate compounds may be screened for those that specifically bind to a polypeptide encoded by a GPR56 and/or Tgm2 gene. The efficacy of such a candidate compound is dependent upon its ability to interact with such a polypeptide or a functional equivalent thereof. Such an interaction can be readily assayed using any number of standard binding techniques and functional assays (e.g., those described in Ausubel et al., supra). In one embodiment, a candidate compound may be tested in vitro for its ability to specifically bind a polypeptide of the invention. In another embodiment, a candidate compound is tested for its ability to increase the biological activity of a polypeptide described herein, such as a GPR56 and/or TG2 polypeptide. The biological activity of a GPR56 and/or TG2 polypeptide may be assayed using any standard method, for example, a myelination assay.

In another working example, a nucleic acid described herein (e.g., a GPR56 and/or Tgm2 nucleic acid) is expressed as a transcriptional or translational fusion with a detectable reporter, and expressed in an isolated cell (e.g., mammalian) under the control of a heterologous promoter, such as an inducible promoter. The cell expressing the fusion protein is then contacted with a candidate compound, and the expression of the detectable reporter in that cell is compared to the expression of the detectable reporter in an untreated control cell. Products for detecting GPCR activity are commercially available including, for example, the Tango™ GPCR Assay System (Thermo Fisher Scientific, Carlsbad, Calif.). A candidate compound that alters the expression of the detectable reporter is a compound that is useful for the treatment of a demyelinating disease or disorder. Preferably, the compound increases the expression of the reporter.

In another example, a candidate compound that binds to a polypeptide encoded by a GPR56 and/or Tgm2 gene may be identified using a chromatography-based technique. For example, a recombinant polypeptide of the invention may be purified by standard techniques from cells engineered to express the polypeptide (e.g., those described above) and may be immobilized on a column. A solution of candidate compounds is then passed through the column, and a compound specific for the GPR56 and/or TG2 polypeptide is identified on the basis of its ability to bind to the polypeptide and be immobilized on the column. To isolate the compound, the column is washed to remove non-specifically bound molecules, and the compound of interest is then released from the column and collected. Similar methods may be used to isolate a compound bound to a polypeptide microarray. Compounds isolated by this method (or any other appropriate method) may, if desired, be further purified (e.g., by high performance liquid chromatography). In addition, these candidate compounds may be tested for their ability to increase the activity of a GPR56 and/or TG2 polypeptide (e.g., as described herein). Compounds isolated by this approach may also be used, for example, as therapeutics to treat a demyelinating disease or disorder in a human patient. Compounds that are identified as binding to a polypeptide of the invention with an affinity constant less than or equal to 10 mM are considered particularly useful in the invention. Alternatively, any in vivo protein interaction detection system, for example, any two-hybrid assay may be utilized.

Animal models may also be to screen candidate compounds. For example, methods of generating genetically modified animals having mutations (e.g., in GPR56) in organisms are known in the art and available to the ordinarily skilled person. In various embodiments, a CRISPR-Cas9 system is used to create a genetically modified organism (see e.g., U.S. Pat. Nos. 8,771,945 and 8,945,839, and US Patent Publication Nos. 20140170753, 20140227787, 20150184139, 20150203872, which are herein incorporated by reference in their entirety). Such organisms may include any eukaryotic organism, including, without limitation, zebrafish and mice. Candidate compounds may be tested for their ability to increase or promote myelination. Tissues of test organisms can be assayed in a number of ways that are routine and well known, including, without limitation, immunohistochemical staining, in situ hybridization, and electron microscopy.

Each of the DNA sequences listed herein may also be used in the discovery and development of a therapeutic compound for the treatment of a demyelinating disease or disorder. The encoded protein, upon expression, can be used as a target for the screening of drugs. Additionally, the DNA sequences encoding the amino terminal regions of the encoded protein or Shine-Delgarno or other translation facilitating sequences of the respective mRNA can be used to construct sequences that promote the expression of the coding sequence of interest. Such sequences may be isolated by standard techniques (Ausubel et al., supra).

Potential antagonists include organic molecules, peptides, peptide mimetics, polypeptides, nucleic acids, and antibodies that bind to a nucleic acid sequence or polypeptide of the invention (e.g., a GPR56 and/or TG2 polypeptide or nucleic acid molecule). Small molecules of the invention preferably have a molecular weight below 2,000 daltons, more preferably between 300 and 1,000 daltons, and most preferably between 400 and 700 daltons. It is preferred that these small molecules are organic molecules.

Test Extracts and Agents

In general, agents that modulate (e.g., activate) GPR56 or TG2/Tgm2 expression, biological activity, or GPR56-dependent signaling are identified from large libraries of both natural products, synthetic (or semi-synthetic) extracts or chemical libraries, according to methods known in the art. Preferably, these compounds increase GPR56 expression or biological activity and/or increase or promote myelination.

Those skilled in the art will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modifications of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from, for example, Brandon Associates (Merrimack, N.H.), Aldrich Chemical (Milwaukee, Wis.), and Talon Cheminformatics (Acton, Ont.)

Alternatively, libraries of natural compounds in the form of bacterial, fungal, plant, and animal extracts are commercially available from a number of sources, including, but not limited to, Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art (e.g., by combinatorial chemistry methods or standard extraction and fractionation methods). Furthermore, if desired, any library or compound may be readily modified using standard chemical, physical, or biochemical methods.

Methods for Evaluating Therapeutic Efficacy

In one approach, the efficacy of the treatment is evaluated by measuring, for example, the biological function of the treated organ (e.g., neuronal function). Such methods are standard in the art and are described, for example, in the Textbook of Medical Physiology, Tenth edition, (Guyton et al., W.B. Saunders Co., 2000). In particular, a method of the present invention, increases the biological function of a tissue or organ by at least 5%, 10%, 20%, 40%, 50%, 60%, 70%, 80%, 90%, 100%, 150%, 200%, or even by as much as 300%, 400%, or 500%. Preferably, the tissue is neuronal tissue and, preferably, the organ is brain. In another approach, the therapeutic efficacy of the methods of the invention is assayed by measuring an increase in myelin or increased myelination in the treated tissue or organism as compared to a corresponding control tissue or organism.

In another approach, the therapeutic efficacy of the methods of the invention is assayed by measuring an increase in cell number in the treated tissue or organ as compared to a corresponding control tissue or organ (e.g., a tissue or organ that did not receive treatment). Preferably, cell number in a tissue or organ is increased by at least 5%, 10%, 20%, 40%, 60%, 80%, 100%, 150%, or 200% relative to a corresponding tissue or organ. Methods for assaying cell proliferation are known to the skilled artisan and are described, for example, in Bonifacino et al., (Current Protocols in Cell Biology Loose-leaf, John Wiley and Sons, Inc., San Francisco, Calif.). For example, assays for cell proliferation may involve the measurement of DNA synthesis during cell replication. In one embodiment, DNA synthesis is detected using labeled DNA precursors, such as [$^{3H}$]-Thymidine or 5-bromo-2*-deoxyuridine [BrdU], which are added to cells (or animals) and then the incorporation of these precursors into genomic DNA during the S phase of the cell cycle (replication) is detected (Ruefli-Brasse et al., Science 302 (5650): 1581-4, 2003; Gu et al., Science 302 (5644): 445-9, 2003).

Kits

The invention provides kits for the treatment or prevention of a disease or disorder characterized by an absence, decrease, or loss of myelination (e.g., a demyelinating disease). In one embodiment, the kit includes a composition containing an effective amount of an agent that modulates (e.g., activate) GPR56 or TG2/Tgm2 expression, biological activity, or GPR56-dependent signaling. In another embodiment, the kit includes a therapeutic or prophylactic composition for increasing or promoting myelination in a subject in need thereof.

In some embodiments, the kit comprises a sterile container which contains a therapeutic or prophylactic cellular composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired an agent of the invention is provided together with instructions for administering the agent to a subject having or at risk of developing a disease or disorder characterized by a deficiency or loss of myelination. The instructions will generally include information about the use of the composition for the treatment or prevention of the disease or disorder. In other embodiments, the instructions include at least one of the following: description of the therapeutic agent; dosage schedule and administration for treatment or prevention of ischemia or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1. Putative Ligand(s) of GPR56 are Expressed in Microglia

To establish the distribution of a putative oligodendrocyte precursor cell (OPC)-specific GPR56 ligand in the developing brain, mouse corpus callosum (CC) tissue sections were screened with a probe comprising the GPR56 NTF fused to human immunoglobulin Fc fragment (GPR56$^N$-hFc). Studies were done at postnatal (P) day 5, when oligodendrocyte precursors (OPCs) are proliferating actively. GPR56 immunohistochemistry (IHC) and GPR56$^N$-hFc binding in situ demonstrated that GPR56$^+$ cells and putative ligand-expressing cells were two independent cell populations in the corpus callosum (CC), which were adjacent to each other to potentially enable receptor-ligand interactions during OL development (FIGS. 1A and 1B). To characterize the lineage of GPR56 ligand-expressing cells, a series of double IHC experiments were performed with GPR56$^N$-hFc paired with Iba1 (to label microglia), GFAP (to label astrocytes) and PDGFRα (to label OPCs). Robust and consistent putative ligand detection was observed in microglia (FIGS. 1C and 1D), while no obvious putative ligand binding was detected in oligodendrocyte precursors (OPCs) and only sparse signals in astrocytes (FIGS. 1E-1H).

Figure 2B:
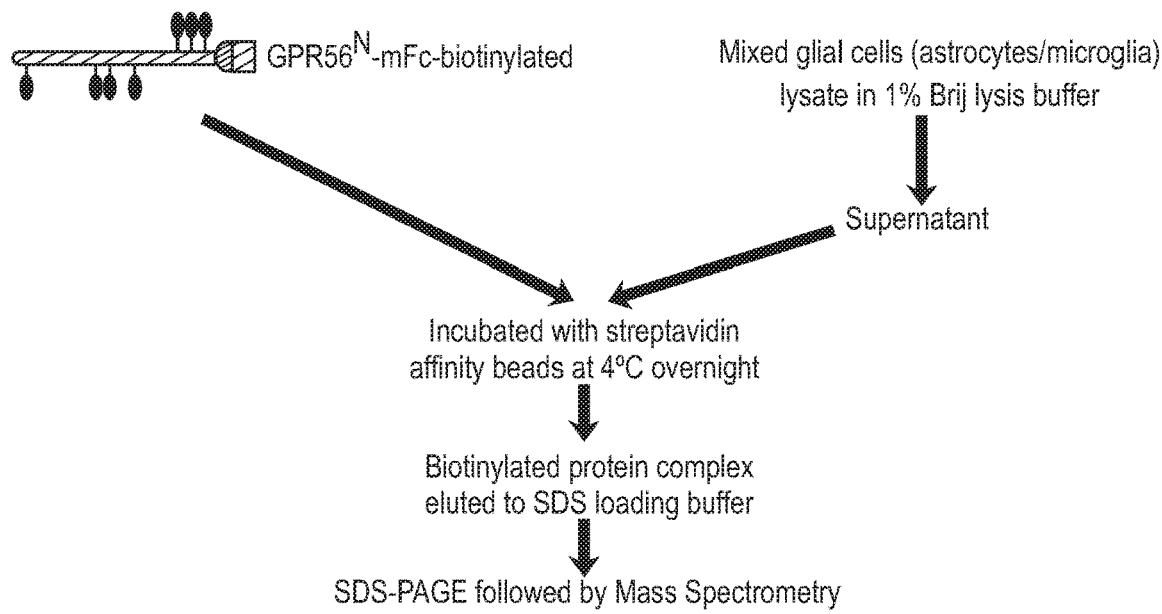

To identify the ligand of GPR56 in OPCs, an in vitro biotinylation/proteomics approach was employed using single-step capture on streptavidin beads to purify the binding partner(s) of GPR56 (FIGS. 2A-2B). Proteins with more than five identified tryptic peptides in the Mass Spectrometry (MS) output from three independent experiments are listed at Table 1.

TABLE 1

Summary of mass spectrometry results from three independent purifications. Total number of peptides sequences in each individual experiment specific for binding to GPR56$^N$.

| Protein name (Gene ID) | Peptide Number (Exp1 + Exp2 + Exp3) |
|---|---|
| Plectin (Plec) | 21 + 22 + 23 |
| Transglutaminase 2 (Tgm2) | 19 + 20 + 17 |
| GPR56 (Gpr56) | 12 + 11 + 9 |

Figure 3F:
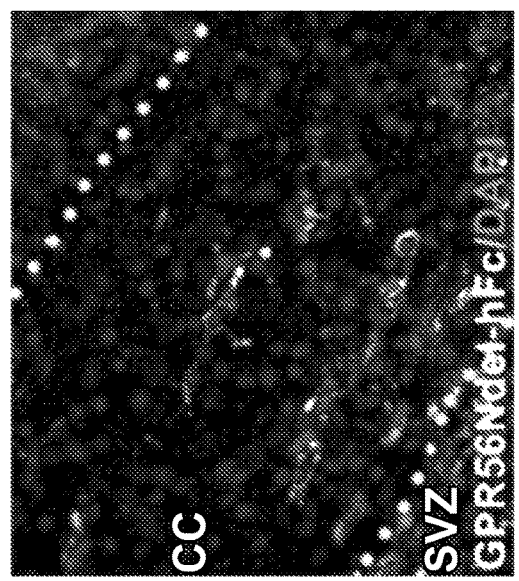
Figure 3E:
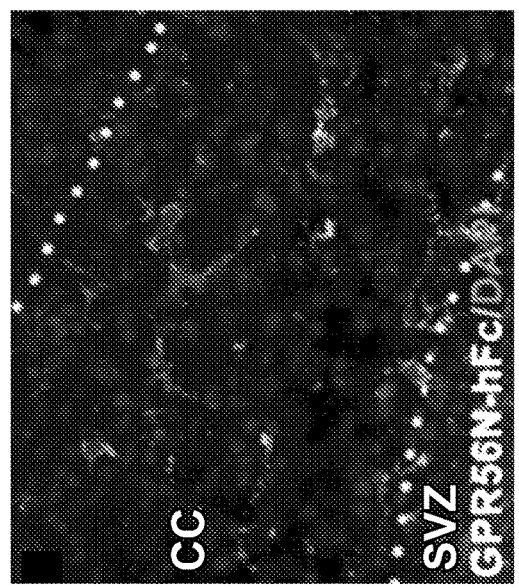
Figure 3D:
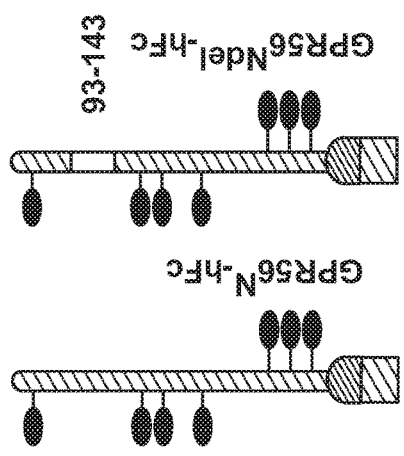
Figure 3I:
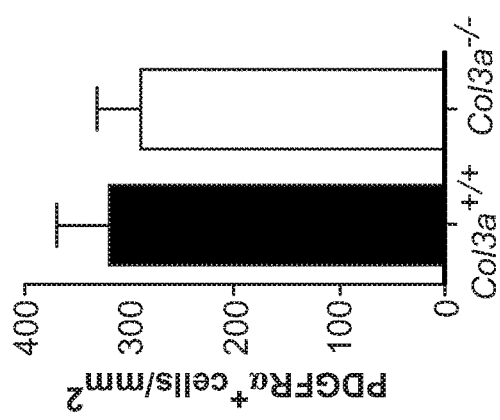
Figure 3L:
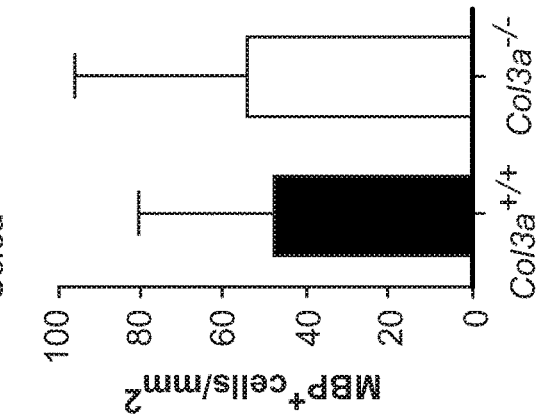
FIG. 3L is a graph showing a comparable number of MBP+ OLs was seen in the spinal cord of Col3a1$^{+/+}$ and Col3a1$^{-/-}$ mice. P=0.8335, unpaired t-test, N=3 per genotype. Error bars are mean±s.e.m in FIGS. 3I and 3L.
Figure 3G:
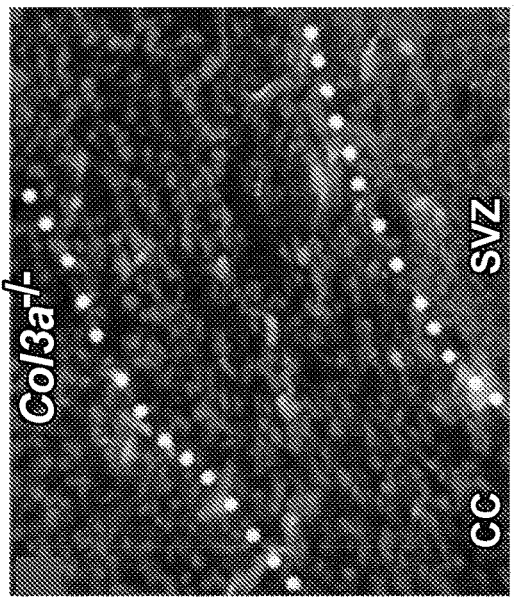
Figure 3H:
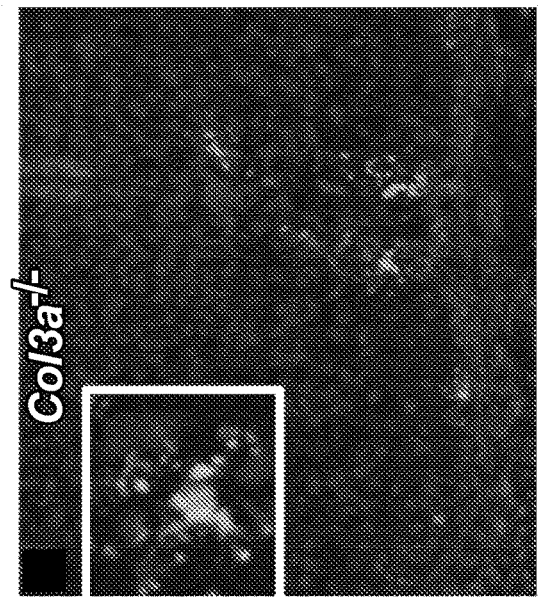
Figure 3J:
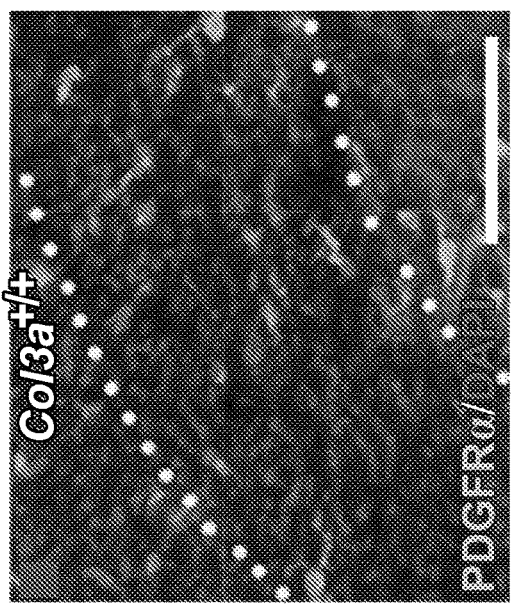
FIG. 3J provides a representative image of IHC for MBP (light gray) on the spinal cord of E18.5 Col3a1$^{+/+}$ mice. DAPI, dark gray. Scale bar, 100 μm.
Figure 3K:
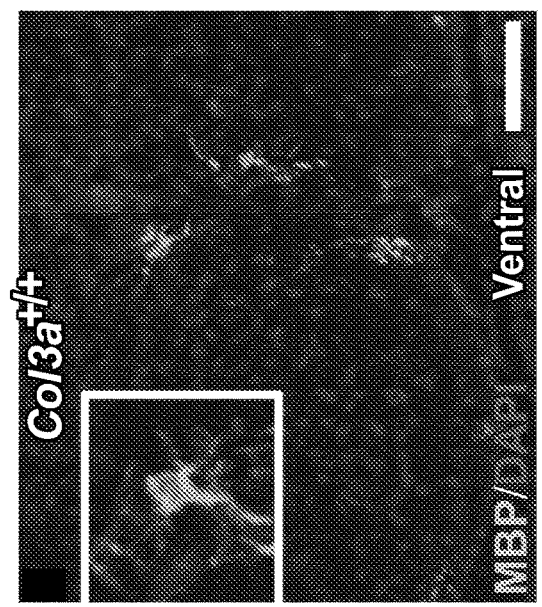
FIG. 3K provides a representative image of IHC for MBP (light gray) on the spinal cord of E18.5 Col3a1$^{-/-}$ mice. DAPI, dark gray. Scale bar, 100 μm.
Figure 4F:
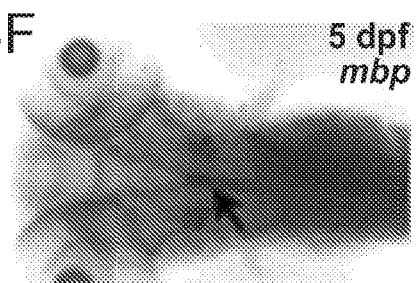
FIG. 4F depicts whole mount in situ hybridization showing myelin basic protein (mbp) expression (CNS denoted by black arrows) at 5 days post-fertilization (dpf) in gas6 control larva (wt and gas6$^{st1228/+}$, N=11/12).
Figure 4G:
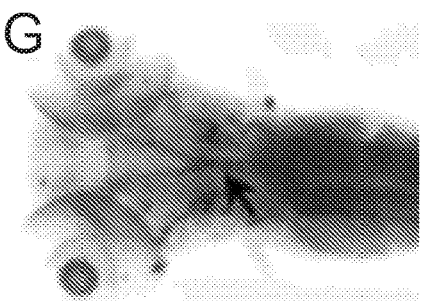
FIG. 4G depicts in situ hybridization showing mbp expression (CNS denoted by black arrows) at 5 days post-fertilization (dpf) in gas6$^{st1228/st1228}$ mutant larva (N=5/8).
Figure 4H:
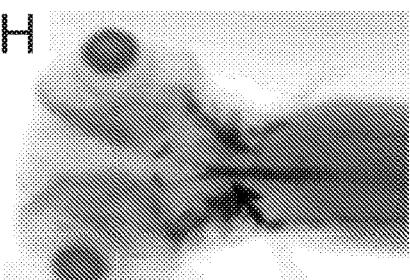
FIG. 4H depicts in situ hybridization showing mbp expression (CNS denoted by black arrows) at 5 days post-fertilization (dpf) in mpp6a control larva (wt and mpp6a$^{st1233/+}$, N=17/18).
Figure 4I:
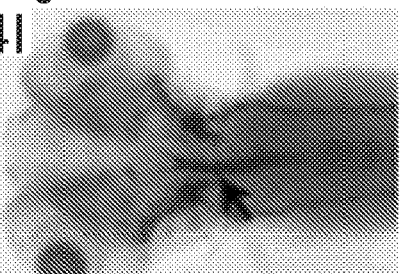
FIG. 4I depicts in situ hybridization showing mbp expression (CNS denoted by black arrows) at 5 days post-fertilization (dpf) in mpp6a$^{st1233/st1233}$ mutant larva (N=5/7).
Figure 4J:
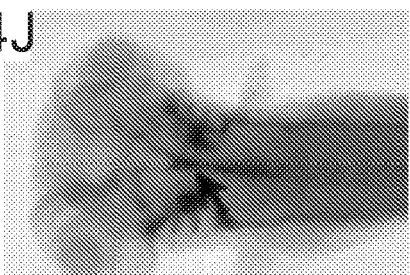
FIG. 4J depicts in situ hybridization showing mbp expression (CNS denoted by black arrows) at 5 days post-fertilization (dpf) in mpp6b control larva (wt and mpp6b$^{st1234/+}$, N=24/24).
Figure 4K:
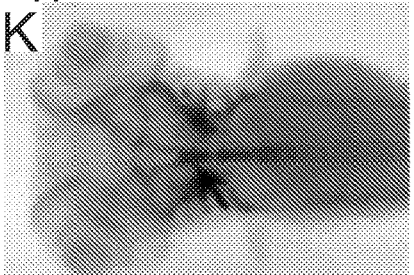
FIG. 4K depicts in situ hybridization showing mbp expression (CNS denoted by black arrows) at 5 days post-fertilization (dpf) in mpp6b$^{st1234/st1234}$ (N=4/4).
Figure 4L:
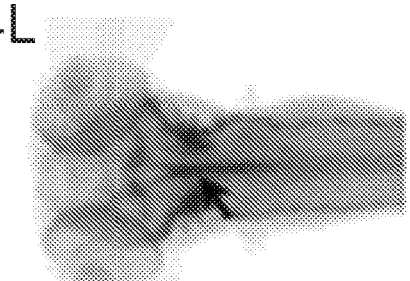
FIG. 4L depicts in situ hybridization showing mbp expression (CNS denoted by black arrows) at 5 days post-fertilization (dpf) in pleca control larva (wt and pleca$^{st1261/+}$, N=18/18).
Figure 4M:
FIG. 4M depicts in situ hybridization showing mbp expression (CNS denoted by black arrows) at 5 days post-fertilization (dpf) in pleca$^{st1261/st1261}$ mutant larva (N=4/4).
Figure 4N:
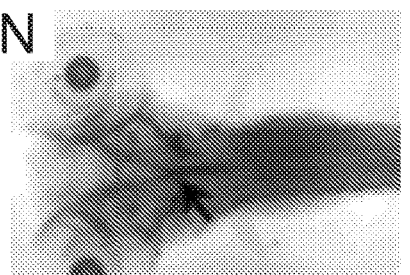
FIG. 4N depicts in situ hybridization of mbp in plecb control larva (wt and plecb$^{st1236/+}$, N=36/38).
Figure 4O:
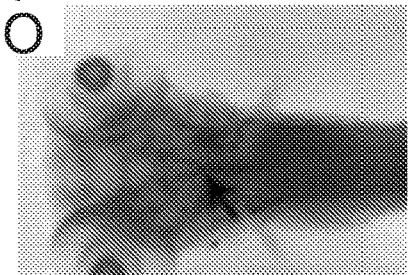

Although collagen III (Col III, gene symbol Col3a1) is the ligand for GPR56 in the developing cerebral cortex (Jeong et al., PLOS One 7, e29767, 2012; Luo et al., Proc Natl Acad Sci USA 108, 12925-12930, 2011), it was not on the putative ligand list. In the postnatal brain, Col III is mainly present at the pial basement membrane and around the CNS vasculature. As oligodendrocyte precursors (OPCs) use CNS vasculature to navigate their migration (Tsai et al., Science 351, 379-384,2016), it was pertinent to consider Col III as a GPR56 ligand during OL development. To further exclude its candidacy as the ligand of OPC GPR56, a series of experiments was carried out. First Col III distribution in mouse corpus callosum (CC) during active gliogenesis was defined (P5). Col III outlined structures consistent with microvasculature in the brain, confirmed by double IHC for Col III and CD31, an endothelial cell marker (FIGS. 3A-3C). Col III binds GPR56 NTF (GPR56$^N$) between amino acids (aa) 27-160, and deleting aa 93-142 (GPR56$^{Ndel}$) abrogated Col III binding (Luo et al., PLOS One 7, e29818, 2012). In situ ligand binding analysis, with GPR56$^N$-hFc and GPR56$^{Ndel}$-hFc probes (FIG. 3D), showed comparable levels of putative ligand binding on the CC of P5 mouse brain (FIG. 3E, 3F). Without being bound by theory, this indicated that Col III was not the ligand recognized by GPR56$^N$-hFc staining in developing CC. To further demonstrate that Col III is not the ligand of GPR56 in the developing white matter, Col3al knockout mice were examined. As homozygous deletion of Col3al results in perinatal lethality (Liu et al., Proc Natl Acad Sci USA 94, 1852-1856, 1997), CC and spinal cord were analyzed in embryonic day (E) 18.5 mouse No significant difference in the number of PDGFRα$^+$ cells in the CC or MBP$^+$ cells in the spinal cord was found in the Col3a1$^{+/+}$ and Col3a1$^{-/-}$ embryos (FIGS. 3G-3L). Without being bound by theory, this lack of phenocopy-expected for a receptor-ligand pair-supports the notion that Col III does not function as a GPR56 ligand during OPC development.

Figure 5D:
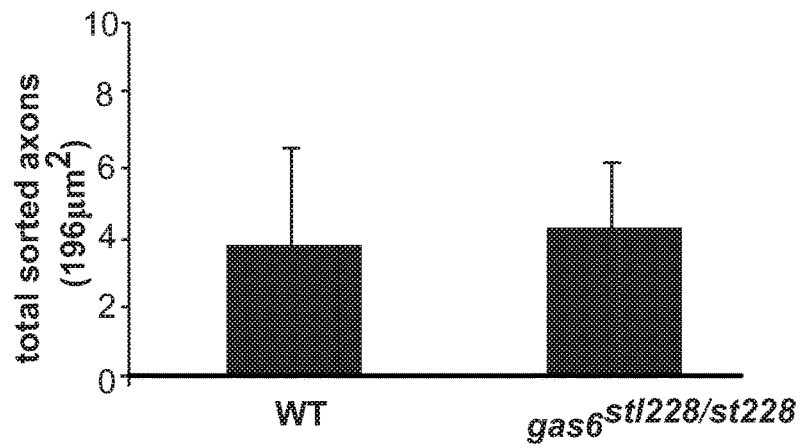
FIG. 5D is a graph showing quantification of total number of axons enwrapped by premyelinating OL within a 196 μm$^2$ region. Quantification of total number of axons enwrapped by premyelinating OL revealed no significant differences between wt and gas6$^{st1228/st1228}$ mutant larvae.
Figure 5E:
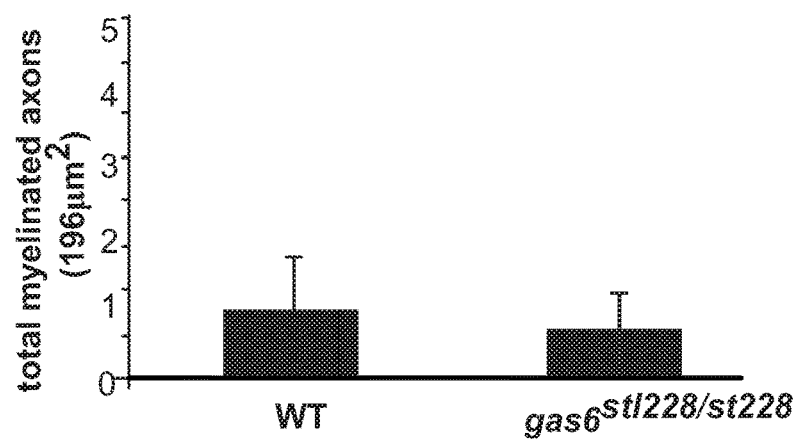
FIG. 5E is a graph showing quantification of total number of myelinated axons within a 196 μm$^2$ region. Quantification of total number of myelinated axons revealed no significant differences between wt and gas6$^{st1228/st1228}$ mutant larvae.
Figure 5F:
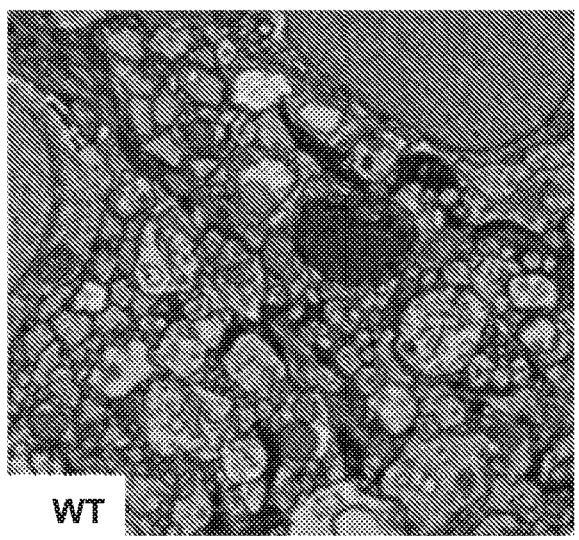
FIG. 5F provides a representative TEM image of ventral spinal cord from mpp6a wt control larva (N=3) at 3 dpf.
Figure 5G:
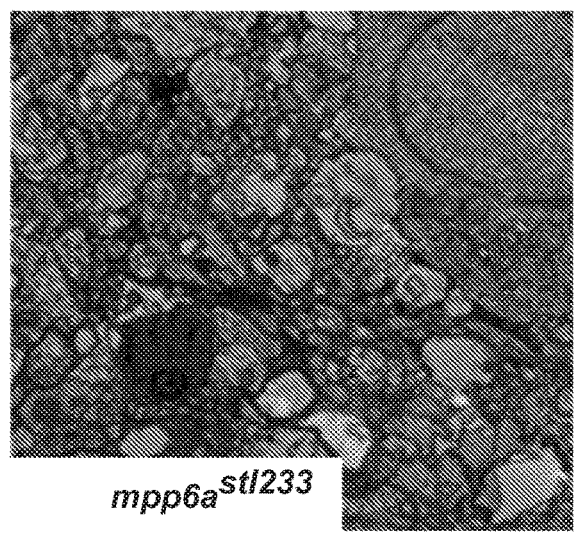
FIG. 5G provides a representative TEM image of ventral spinal cord from mpp6a$^{st1233/st1233}$ mutant larva (N=4) at 3 dpf.
Figure 5H:
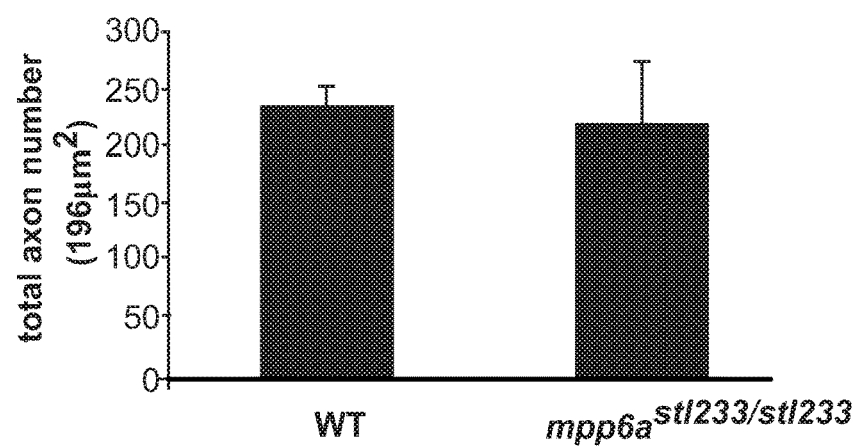
FIG. 5H is a graph showing quantification of total axon number within a 196 μm$^2$ region. Quantification of total axon number revealed no significant differences between wt and mpp6b$^{st1233/st1233}$ mutant larvae.
Figure 5I:
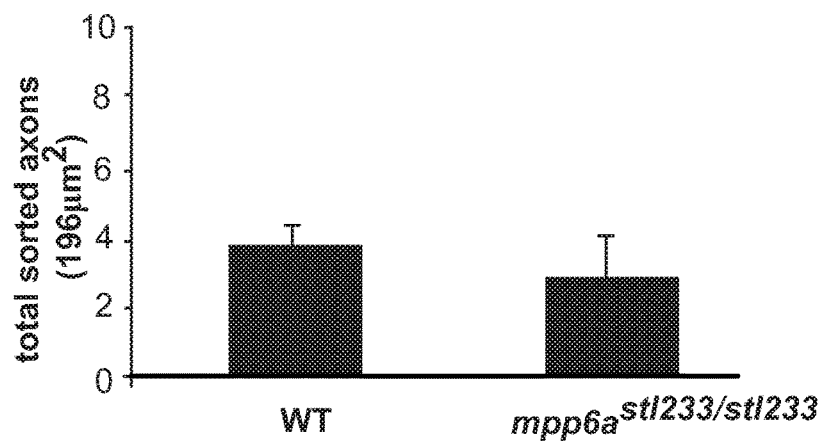
FIG. 5I is a graph showing quantification of total number of sorted axons within a 196 μm$^2$ region. Quantification of total number of sorted axons revealed no significant differences between wt and mpp6a$^{st1233/st1233}$ mutant larvae.
Figure 5J:
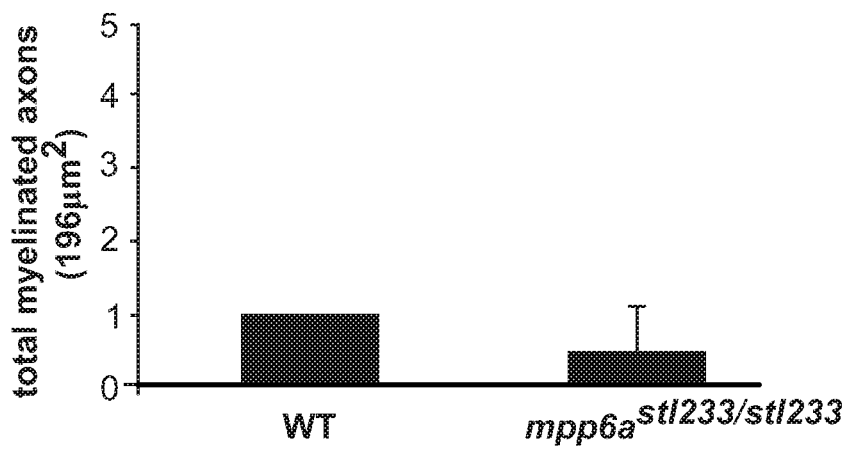
FIG. 5J is a graph showing quantification of total number of myelinated axons within a 196 μm$^2$ region. Quantification of total number of myelinated axons revealed no significant differences between wt and mpp6a$^{st1233/st1233}$ mutant larvae.
Figure 5K:
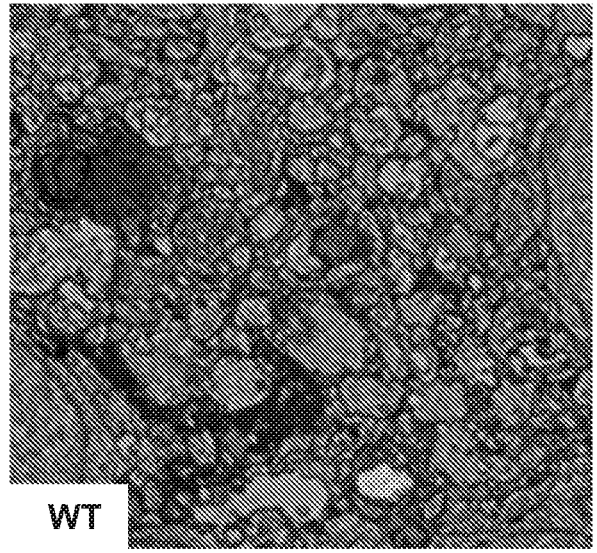
FIG. 5K provides a representative TEM image of ventral spinal cord from mpp6b wt control larva (N=3) at 3 dpf.
Figure 5L:
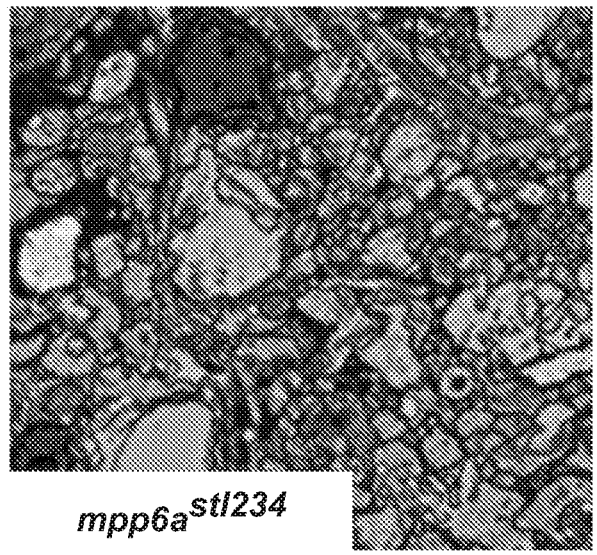
FIG. 5L provides a representative TEM image of ventral spinal cord from mpp6b$^{st1234/st1234}$ mutant larva (N=3) at 3 dpf.
Figure 5M:
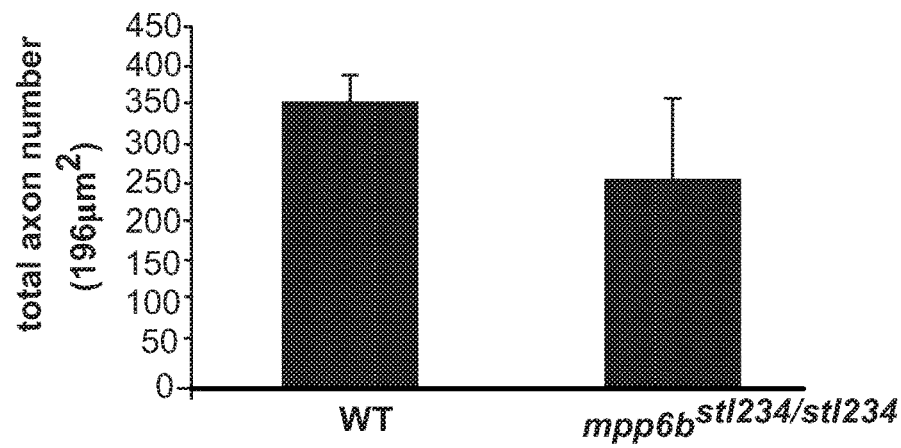
FIG. 5M is a graph showing quantification of total axon number within a 196 μm$^2$ region. Quantification of total axon number revealed no significant differences between wt and mpp6b$^{st1234/st1234}$ mutant larvae.
Figure 5N:
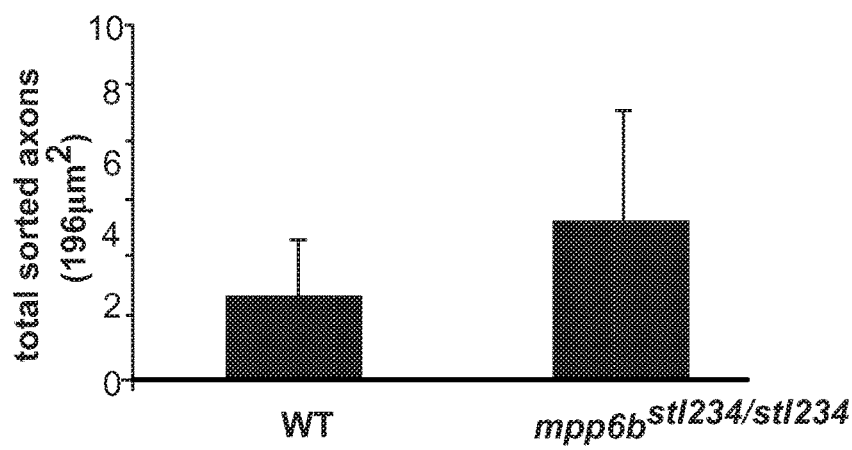
FIG. 5N is a graph showing quantification of total number of sorted axons within a 196 μm² region. Quantification of total number of sorted axons revealed no significant differences between wt and mpp6b$^{st1234/st1234}$ mutant larvae.
Figure 5O:
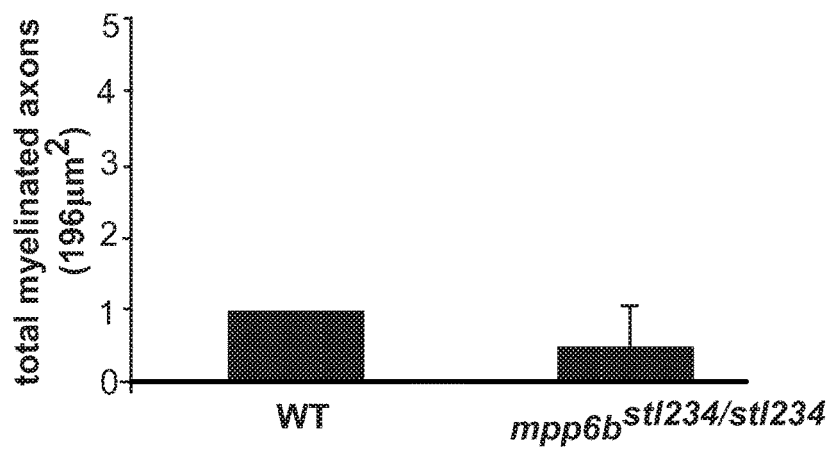
FIG. 5O is a graph showing quantification of total number of myelinated axons within a 196 μm² region. Quantification of total number of myelinated axons revealed no significant differences between wt and mpp6b$^{st1234/st1234}$ mutant larvae.
Figure 5P:
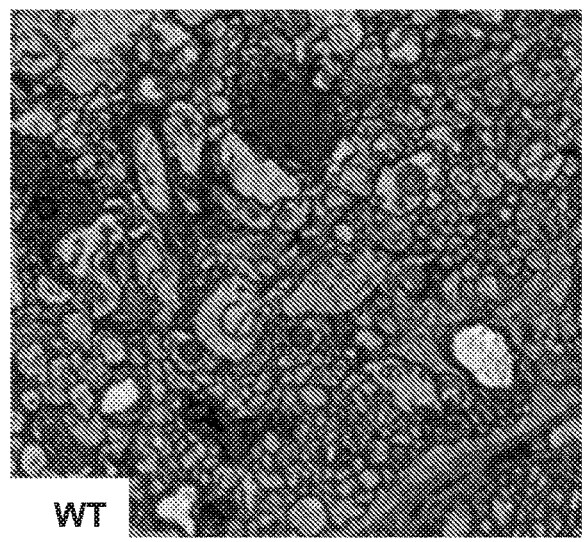
FIG. 5P provides a representative TEM image of ventral spinal cord from pleca wt control larva (N=3) at 3 dpf.
Figure 5Q:
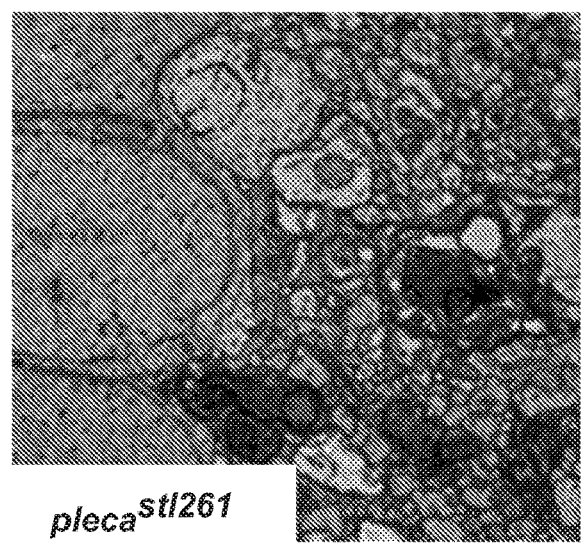
FIG. 5Q provides a representative TEM image of ventral spinal cord from pleca$^{st1261/st1261}$ mutant larva (N=3) at 3 dpf.
Figure 5R:
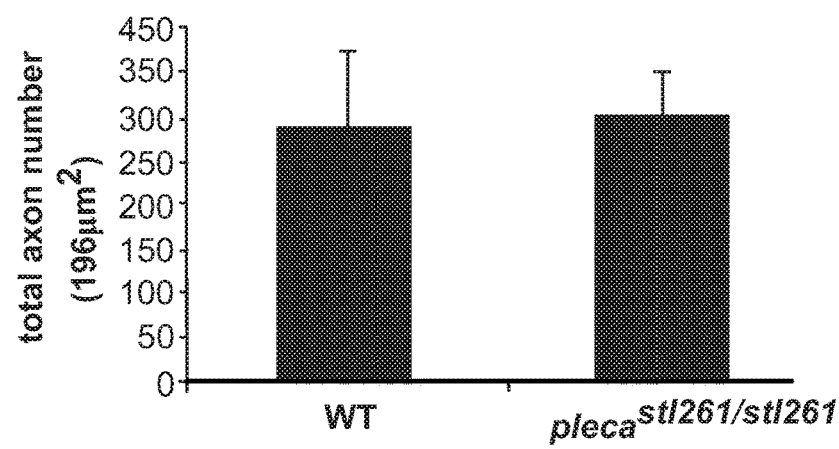
FIG. 5R is a graph showing quantification of total axon number within a 196 μm² region. Quantification of total axon number revealed no significant differences between wt and pleca$^{st1261/st1261}$ mutant larvae.
Figure 5S:
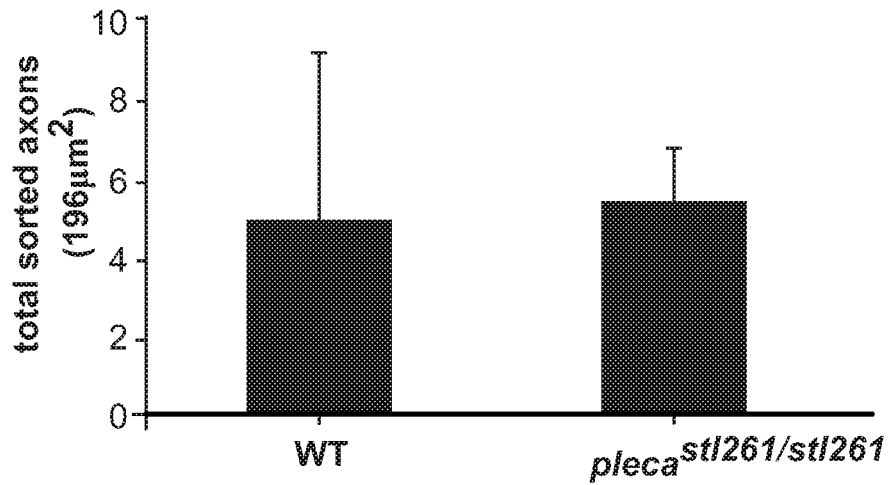
FIG. 5S is a graph showing quantification of total number of sorted axons within a 196 μm² region. Quantification of total number of sorted axons revealed no significant differences between wt and pleca$^{st1261/st1261}$ mutant larvae.
Figure 5T:
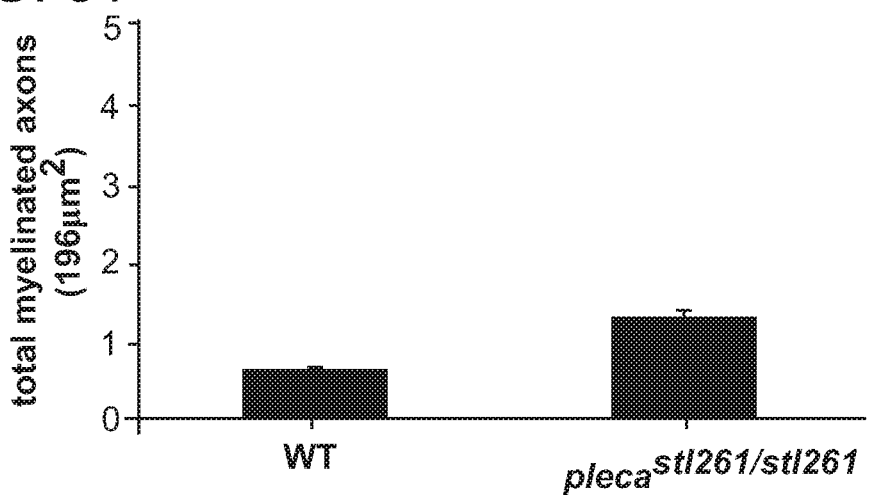
FIG. 5T is a graph showing quantification of total number of myelinated axons within a 196 μm² region. Quantification of total number of myelinated axons revealed no significant differences between wt and pleca$^{st1261/st1261}$ mutant larvae.
Figure 5U:
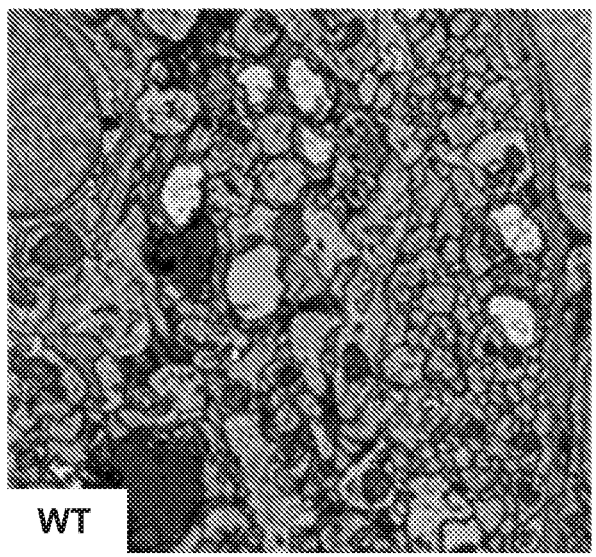
FIG. 5U provides a representative TEM image of ventral spinal cord from plecb wt control larva (N=5) at 3 dpf.
Figure 5V:
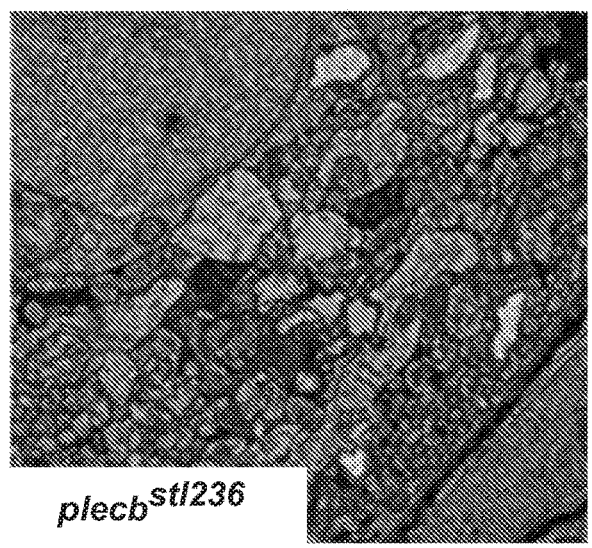
FIG. 5V provides a representative TEM image of ventral spinal cord from plecb$^{st1236/st1236}$ mutant larva (N=4) at 3 dpf.
Figure 5W:
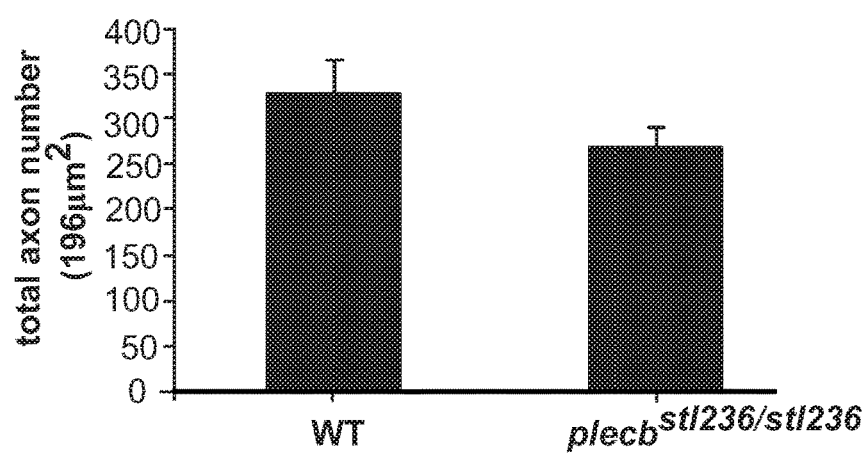
FIG. 5W is a graph showing quantification of total axon number of myelinated axons within a 196 μm² region. Quantification of total axon number revealed no significant differences between wt and plecb$^{st1236/st1236}$ mutant larvae.
Figure 5X:
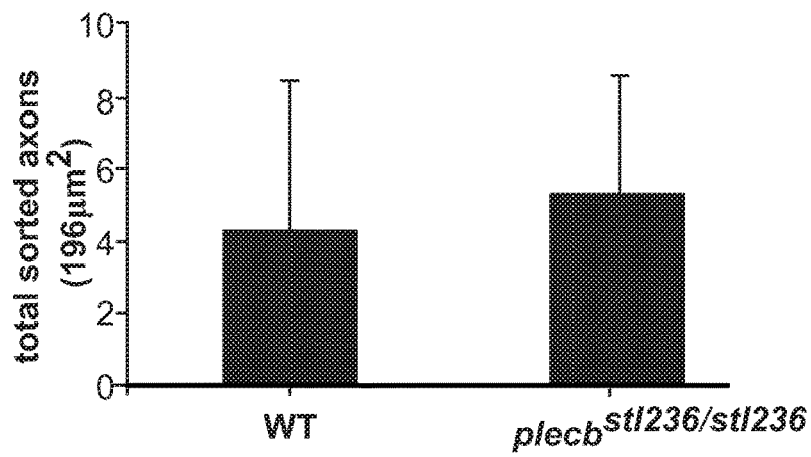
FIG. 5X is a graph showing quantification of total number of sorted axons within a 196 μm² region. Quantification of total number of sorted axons revealed no significant differences between wt and plecb$^{st1236/st1236}$ mutant larvae.
Figure 5Y:
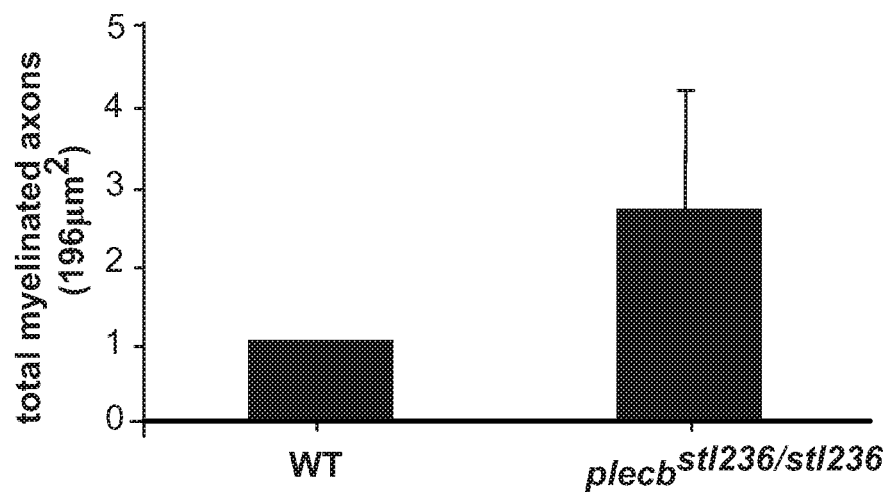

Next, the candidate binding partners of GPR56 listed at Table 1 were prioritized. Given that GPR56, like many aGPCRs, mediates cell-cell and cell-ECM interactions (Hamann et al., Pharmacol Rev 67, 338-367, 2015; Langenhan et al., Sci Signal 6, re3, 2013), plasma membrane-associated and ECM proteins were examined, and Atp1a1, Dars, and Macf1 were eliminated as candidates. Zebrafish, in which Gpr56 function in OL development is conserved (Ackerman et al., Nat Commun 6, 6122, 2015), were used to screen the remaining candidates. New mutant alleles of genes encoding the zebrafish orthologs of Gas6 (gas6), Mpp6 (mpp6a, mpp6b), and Plectin (pleca, plecb) were generated using CRISPR/Cas9 genome editing (FIGS. 4A-4E). Whole mount in situ hybridization (ISH) for myelin basic protein (mbp) at 5 days post-fertilization did not reveal CNS myelination phenotypes in any of the putative-ligand zebrafish mutants at this stage (FIG. 4F-4O), a time point at which gpr56 zebrafish mutants exhibit reduced mbp expression (Ackerman et al., Nat Commun 6, 6122, 2015). Transmission electron microscopy (TEM) was used to characterize myelin-axon relationships in the ventral spinal cords of these zebrafish mutants, and showed no defects in total axon number, total numbers of sorted axons (enwrapped by premyelinating OL), nor of total myelinated axon number (FIGS. 5A-5Y). This lack of phenocopy of gpr56 zebrafish mutants suggests that Gas6, Mpp6, and Plectin do not function as ligands for Gpr56 during OPC development.

Example 2. Tgm2 Knockout Mice Displayed Reduced Myelination

Figure 6C:
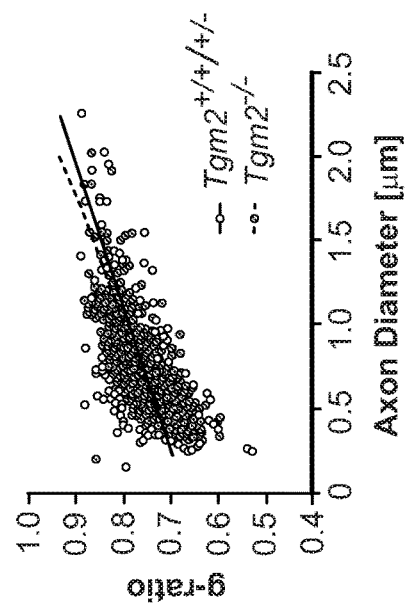
Figure 6D:
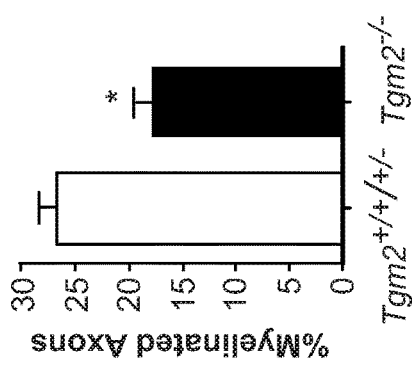
Figure 6E:
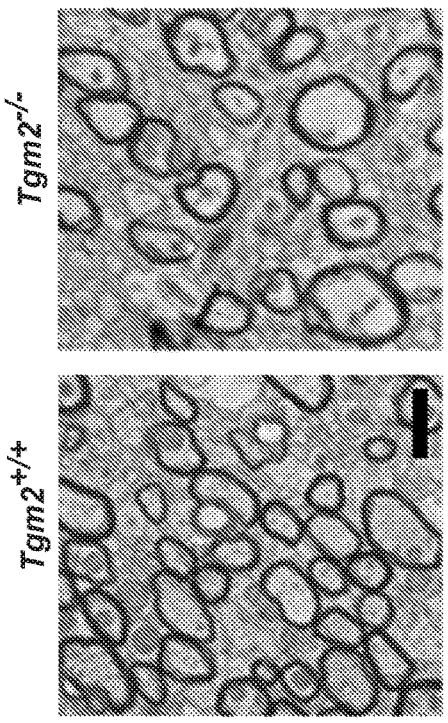
Figure 6F:
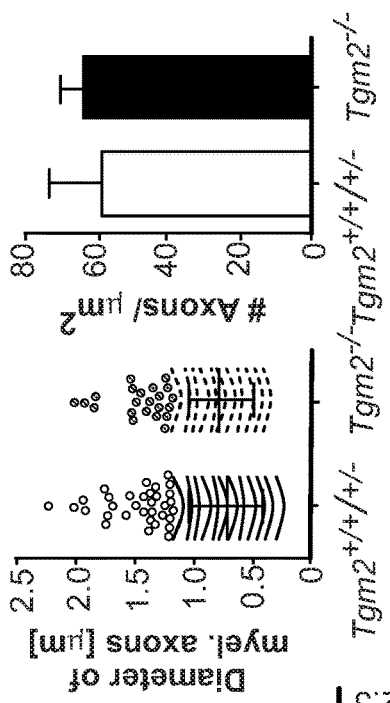
Figure 6G:
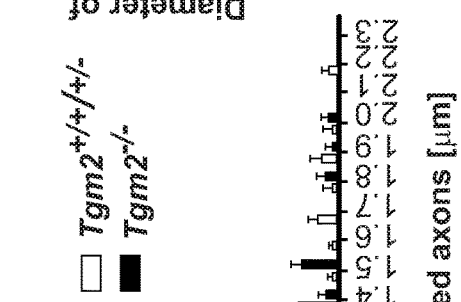
Figure 6H:
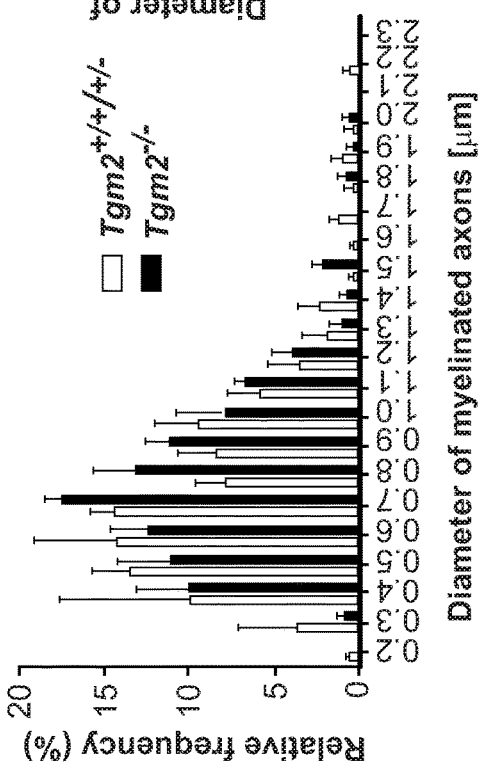
Figure 6I:
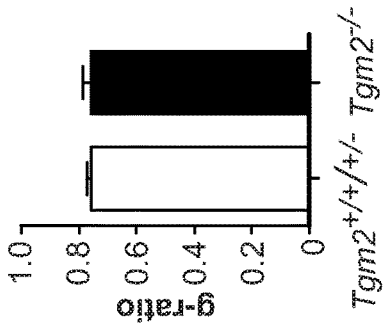
Figure 7:
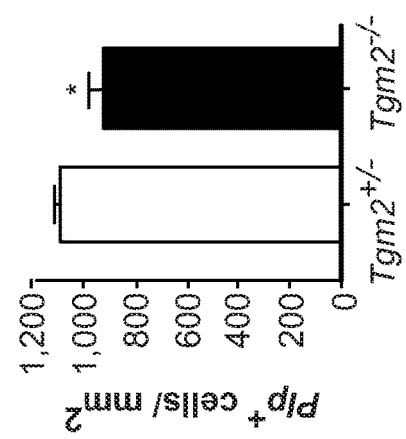
FIGS. 7A-7H show a comparable degree of reduction in the number of mature OLs between Tgm2 and Gpr56 knockout mice as well as OPC-specific Gpr56 knockout mice.
Figure 7B:
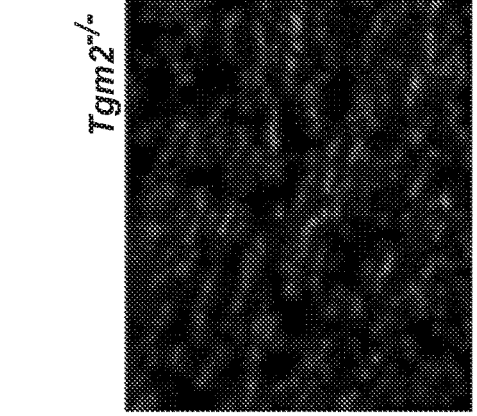
Figure 7A:
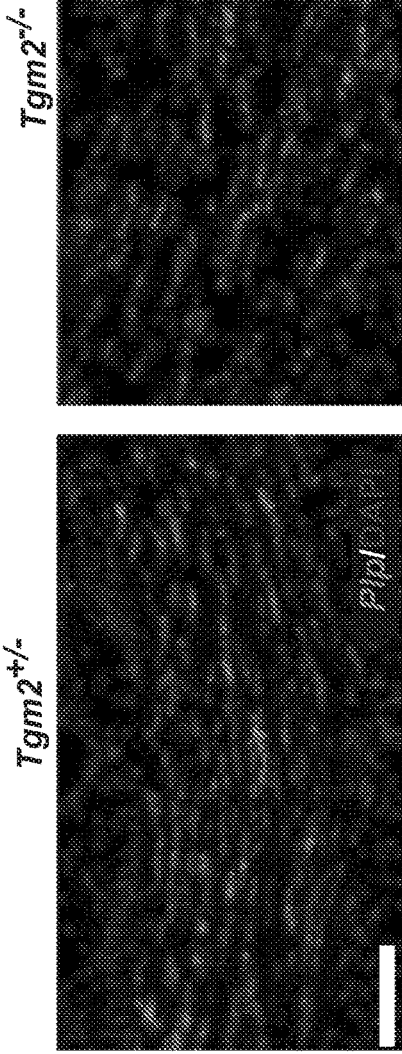

TG2, a known GPR56 binding partner in melanoma cells (Xu et al., Proc Natl Acad Sci USA 103, 9023-9028, 2006), was examined. To evaluate the candidacy of TG2 as the ligand of OPC-GPR56, it was investigated whether deleting Tgm2 phenocopies the myelination phenotype observed in Gpr56 knockout mice. Indeed, significantly reduced numbers of Plp$^+$ mature OLs were observed in the corpus callosum (CC) of Tgm2 knockouts at both P14 and P28 compared to littermate controls (FIGS. 6A and 6B). TEM analysis of sagittal sections from P28 control and Tgm2$^{-/-}$ CC showed significantly fewer myelinated axons in Tgm2$^{-/-}$ mice compared to littermate controls (FIGS. 6C and 6D), whereas myelin thickness corrected for axon caliber (g-ratio), total axon numbers and axon diameters were comparable between the two groups of animals (FIGS. 6E-6I). Importantly, the level of reduction in OL numbers was comparable between in Tgm2$^{-/-}$ and Gpr56$^{-/-}$ mutant mice (FIGS. 7A-7D). Taken together, these data support the notion that TG2 is the ligand of OPC-GPR56.

Figure 8B:
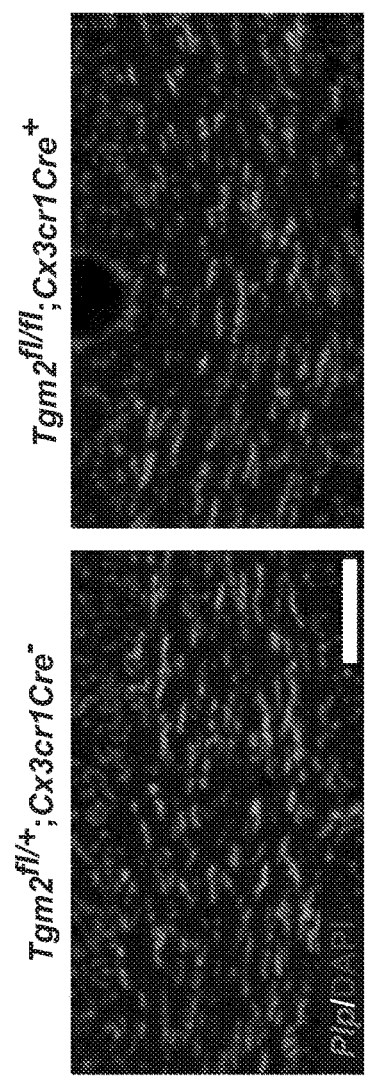
FIGS. 8A-8C show that microglial TG2 is required for normal OL development.
Figure 8C:
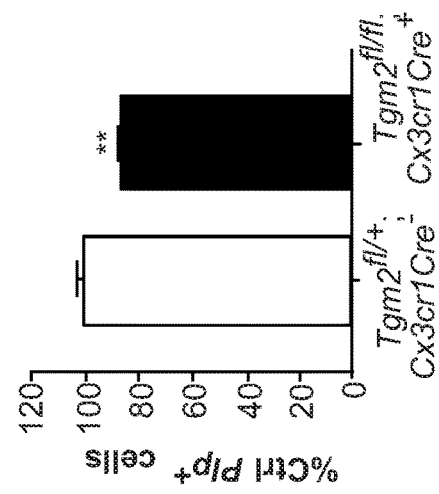
Figure 8A:
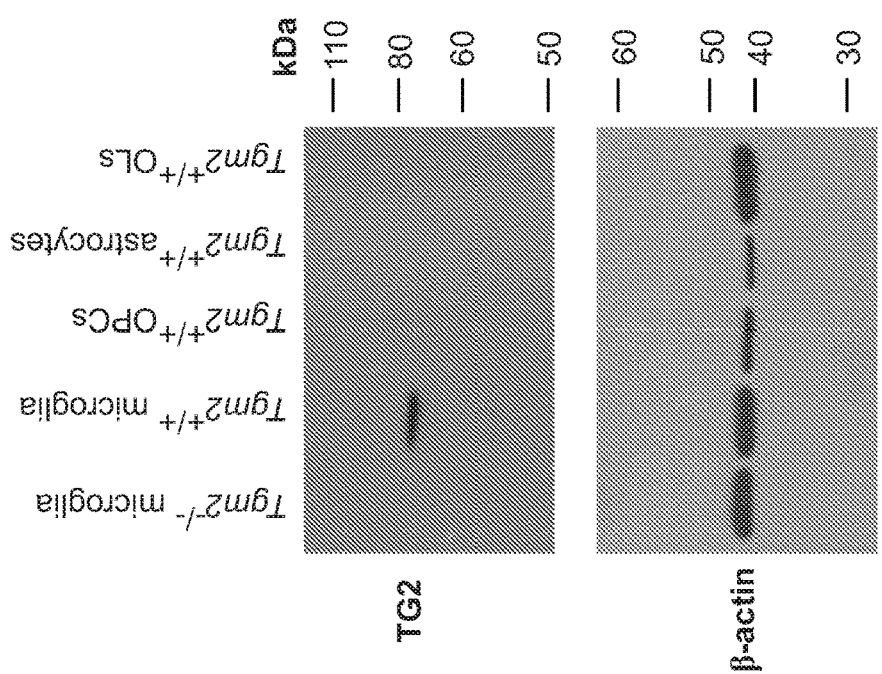

Example 3. Both Germline and Microglia-Specific Conditional Tgm2 Deletion LED to a Similar Reduction in OL Numbers Recent transcriptomic studies of various glial cells revealed that Tgm2 is mainly expressed by microglia in postnatal brains (Zhang et al., J Neurosci 34, 11929-11947, 2014). Consistent with this report, Western blot analysis from highly purified, immunopanned murine glial cells demonstrated selective TG2 enrichment in microglia (FIG. 8A). To further establish that microglial TG2 regulates OL development, the effect of conditionally deleting microglial Tgm2 on the production of mature OLs was studied. Tgm2 floxed mice (Nanda et al., J Biol Chem 276, 20673-20678, 2001) were crossed with Cx3cr1-Cre mice (Yona et al., Immunity 38, 79-91, 2013) where Cre recombinase expression is restricted to microglia. The numbers of Plp$^+$ mature OLs in the corpus callosum (CC) of microglia-specific Tgm2 knockout mice (Tgm2$^{fl/fl}$; Cx3cr1Cre$^+$) were significantly reduced, compared to the littermate Tgm2$^{fl/+}$; Cx3cr1Cre$^-$ controls (FIGS. 8B and 8C). Importantly, the reduction was comparable to what was observed in the constitutive Tgm2 knockout on P28 (FIGS. 6A and 6B). Without being bound by theory, this supports the hypothesis that microglia are the relevant source of TG2 during OL development.

It is worth noting that the level of reduction in OL numbers was comparable between constitutive Gpr56 knockout and OPC-specific Gpr56 conditional knockout mice (FIGS. 7E-7H) (Giera et al., Nat Commun 6, 6121, 2015). Moreover, haploinsufficiency for either Gpr56 (Giera et al., Nat Commun 6, 6121, 2015) or Tgm2 had no effect on OL development (FIGS. 9A-9D). Therefore, constitutive Gpr56 knockout mice were used for mechanistic studies, and Gpr56 and Tgm2 wild type (wt) and heterozygous mice for controls to conserve the number of animals.

Figures 10, 10A, 10B, 10C:
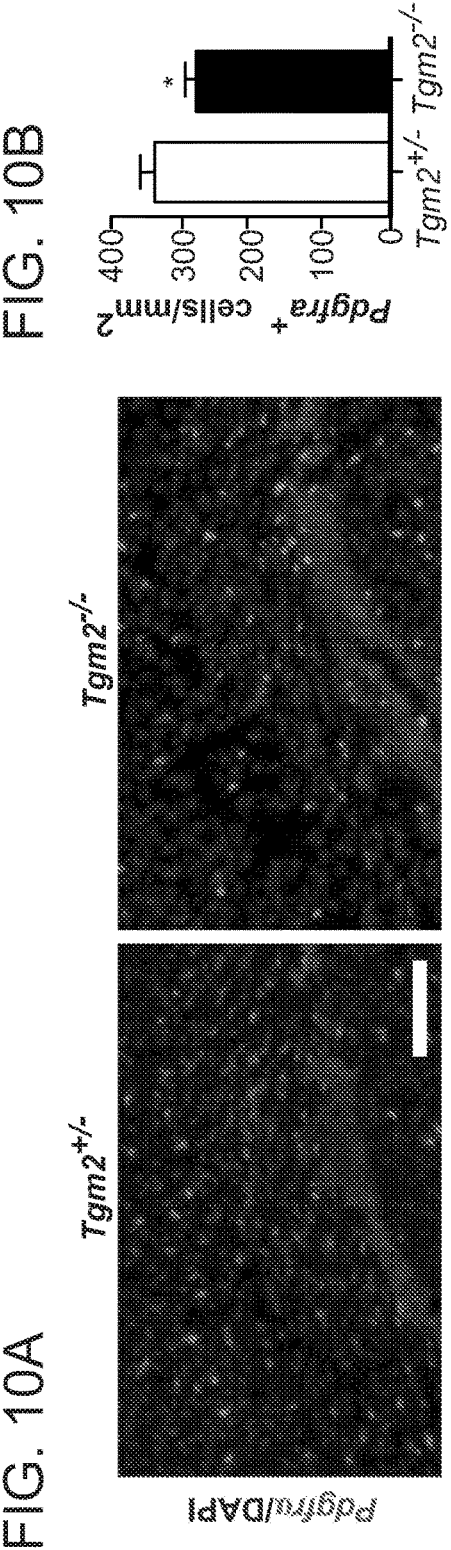
Figure 10J:
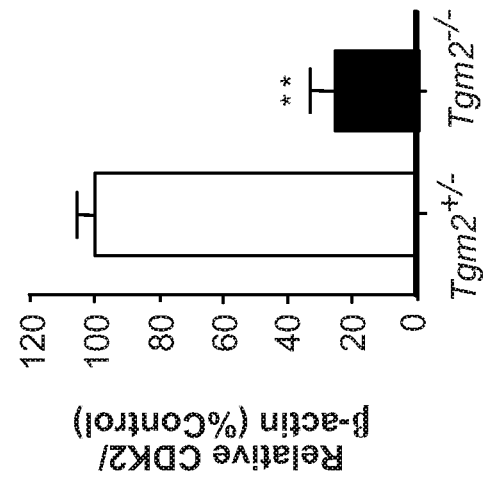
Figure 10I:
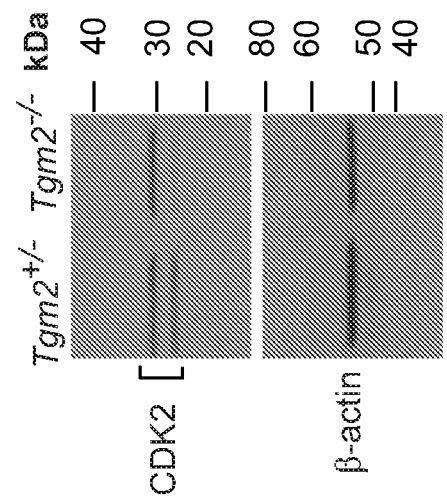

Example 4. Transglutaminase 2 (TG2) Regulates Oligodendrocyte Precursor (OPC) Proliferation Whether Transglutaminase 2 (TG2) regulates oligodendrocyte precursor (OPC) proliferation in the developing white matter was investigated, as was previously documented function for GPR56. Indeed, Pdgfrα$^+$ OPCs in the corpus callosum (CC) of Tgm2$^{-/-}$ mice were significantly reduced compared to controls at P14 (FIGS. 10A and 10B). The reduction in OPC numbers in the CC of Tgm2 knockout mice on P14 is similar as previously observed in Gpr56 knockout mice (FIGS. 11A-11D). Previous studies showed that loss of Gpr56 in the OL lineage causes premature cell cycle exit (Giera et al., Nat Commun 6, 6121, 2015), accounting for diminished size of OPC pool and fewer mature OLs. To further determine if TG2 is the ligand of OPC GPR56, cell cycle exit assays were performed (FIG. 10C). Significantly fewer BrdU$^+$/Ki67$^+$ double positive cells were found in the CC of Tgm2 knockouts compared to the controls (FIGS. 10D and 10E). Consistent with decreased OPC proliferation, fewer BrdU$^+$ cells (FIG. 10F) and fewer PDGFRα$^+$/BrdU$^+$ cells were observed in Tgm2 knockout mice compared to littermate controls (FIGS. 10G and 10H). Cyclin-dependent kinase 2 (CDK2) regulates OPC cell cycle progression (Belachew et al., J Neurosci 22, 8553-8562, 2002; Jablonska et al., The Journal of cell biology 179, 1231-1245, 2007). Western blot analysis of CDK2 in acutely isolated oligodendrocyte precursors (OPCs) from P6 Tgm2$^{-/-}$ and littermate controls showed significantly decreased levels of CDK2 protein in OPCs isolated from Tgm2$^{-/-}$ mice (FIGS. 10I and 10J). Taken together, it was concluded that OPCs prematurely exit the cell cycle in the absence of TG2, as was previously reported in Gpr56 knockout mice (Giera et al., Nat Commun 6, 6121, 2015).

Example 5. GPR56 was Required for Efficient Remyelination after Cuprizone-Induced Demyelination Frequently, tissue repair recapitulates development. It was found that microglial TG2 interaction with OPC-derived GPR56 sustained OPC proliferation during developmental myelination. A previous report showed that Tgm2 deficient mice exhibited impaired remyelination following cuprizone feeding (Van Strien et al., Glia 59, 1622-1634, 2011). Without being bound by theory, the relevant OPC receptor might be GPR56. To study whether deleting OPC Gpr56 might impair remyelination, cuprizone was fed to OPC-specific Gpr56 knockout mice and littermate controls for 6 weeks and assessed remyelination status by staining myelin with Black-Gold solution after 0, 3, 7 and 10 days recovery (DR). Quantitative morphometry revealed a significant decrease in remyelination at 7 and 10 DR (FIGS. 12A and 12B).

To further evaluate whether TG2 promotes remyelination dependent on GPR56, studies were conducted using an in vitro model of demyelination/remyelination in lysophosphatidylcholine (LPC; lysolecithin)-treated cerebellar slices (Birgbauer et al., Journal of neuroscience research 78, 157-166, 2004), a model with different mechanisms of demyelination and repair to that induced by cuprizone feeding. After 24 hr of LPC-mediated demyelination, 4 days of remyelination (4DR) resulted in vigorous remyelination in wt cerebellar slices, whereas significantly impaired remyelination was observed in cerebellar slices derived from OPC-specific Gpr56 knockouts pups (FIGS. 12C-12E). Recombinant TG2 rescued remyelination in Tgm2$^{-/-}$ cerebellar slices but not Tgm2/Gpr56 double knockout slices (FIGS. 12F-12H), demonstrating that the ligation of GPR56 by TG2 is required for efficient remyelination after LPC-mediated injury.

Figure 13:
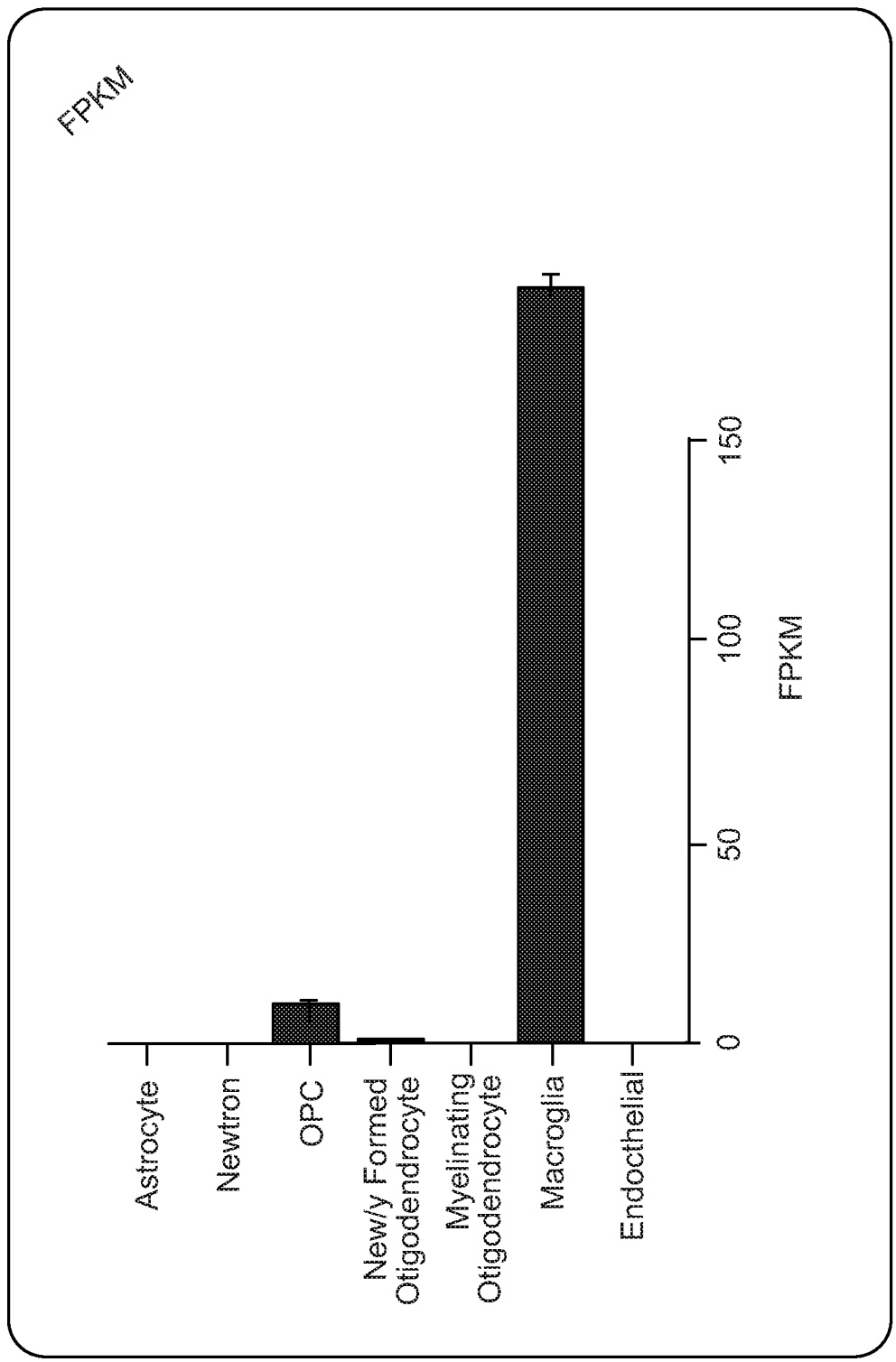
FIG. 13 is a graph displaying the level of Tgm2 transcripts in various CNS cell types. FPKM; normalized expression value of total reads and gene coding length. (Stanford University; web.stanford.edu/group/barres_lab/brain_rnase-q.html).
Figure 14:
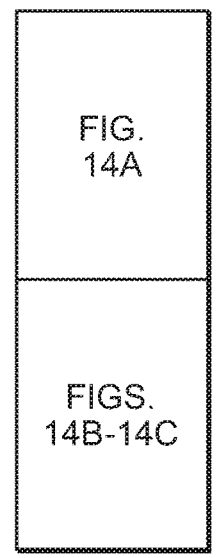
FIGS. 14A-14C show that microglia express TGM2 and that recombinant TGM2 promoted OPC proliferation through GPR56.
Figure 14A:
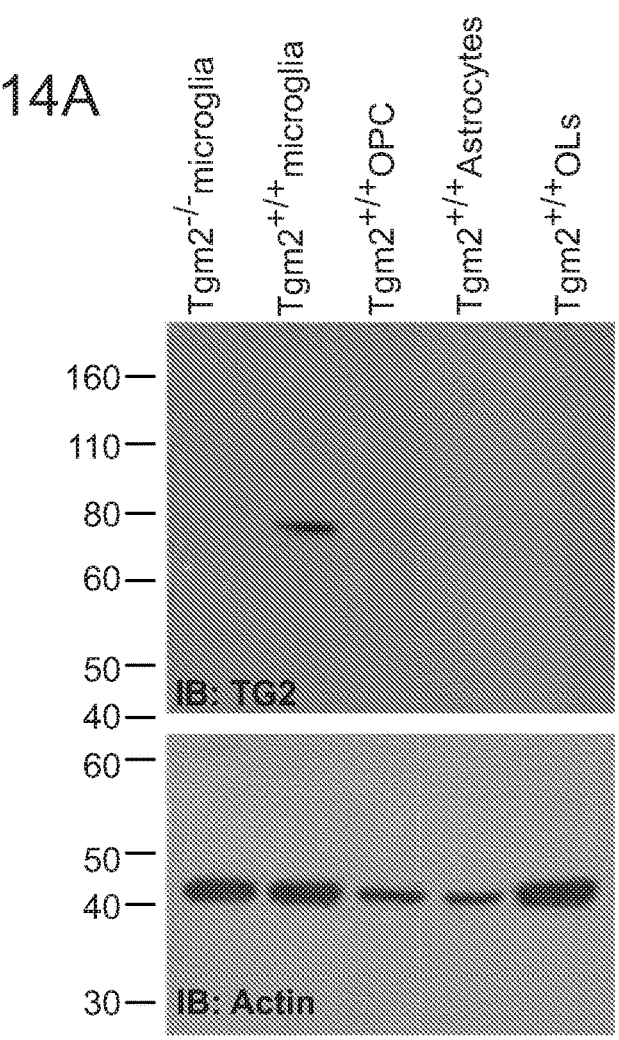
Figure 14B:
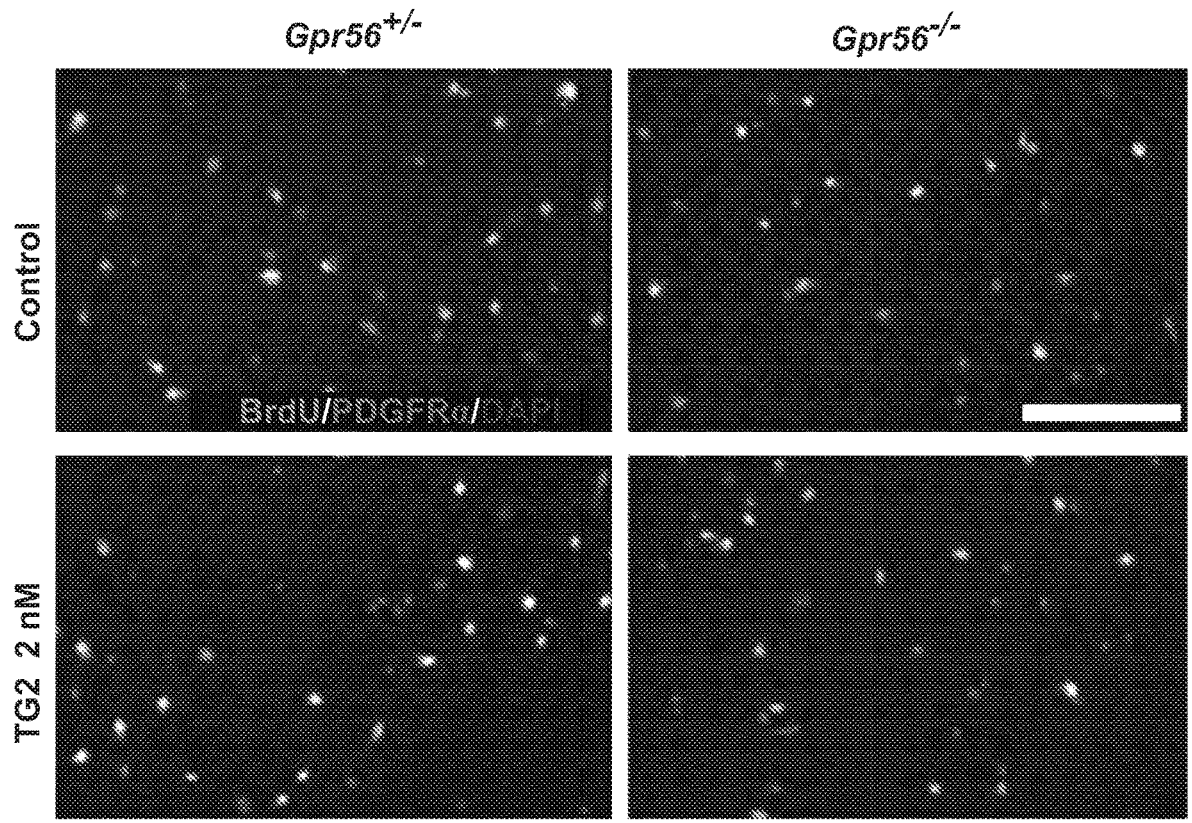
Figure 14C:
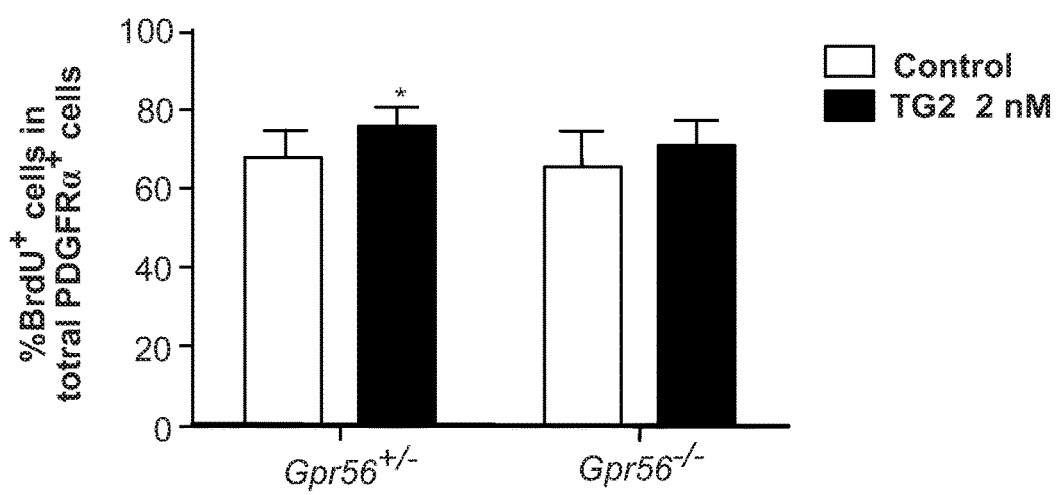

Example 6. Transglutaminase 2 (TG2) Predominantly Expressed in Microglia Promoted Oligodendrocyte Precursor (OPC) Proliferation In Vitro Recent RNA-seq data shows that Tgm2 is mostly expressed in microglia (FIG. 13). Consistent with this observation, western blot analysis from immunopanned various glial cells demonstrated that TGM2 protein was only present in microglia and not in any other cell types including oligodendrocyte precursors (OPCs) (FIG. 14A). To investigate whether TGM2 directly regulates OPC proliferation in a GPR56-dependent manner, OPCs derived from P5 Gpr56$^{+/-}$ or Gpr56$^{-/-}$ pups were cultured in the presence or absence of human recombinant TGM2 (FIGS. 15A and 15B) with the presence of BrdU. The cells were double immunostained for PDGFRα and BrdU (FIG. 14B). Gpr56$^{-/-}$ OPC proliferation was significantly increased in the presence of 2 nM recombinant TGM2, whereas this effect was attenuated in Gpr56$^{-/-}$ OPCs (FIG. 14C). Taken together, these data show that recombinant TGM2 promoted OPC proliferation in a GPR56-dependent fashion.

Example 7. Transglutaminase 2 (TG2) Functions Together with Laminin to Stimulate Oligodendrocyte Precursor (OPC) Proliferation To establish conditions for mechanistic investigation of the function of TG2 on OPC GPR56 during myelination and remyelination, in vitro experiments were performed with wt and Gpr56$^{-/-}$ oligodendrocyte precursors (OPCs) and human recombinant TG2. Surprisingly and unexpectedly, TG2 failed to augment the proliferation of wt OPCs (FIG. 16A). TG2 is an extracellular protein with intrinsic transamidation activity, capable of cross-linking ECM proteins, including laminin-111 (Aeschlimann et al., J Biol Chem 267, 11316-11321, 1992; Belkin, FEBS J 278, 4704-4716, 2011). Interestingly, OPC proliferation was significantly increased in the presence of both recombinant TG2 and laminin-111 whereas fibronectin, a specificity control, was inert in this assay (FIG. 16A). Without being bound by theory, these data indicate that activating OPC GPR56 forms a signaling triad with TG2 and laminin-111 in order to support proliferation. Consistent with this hypothesis, TG2 function towards oligodendrocyte precursors (OPCs) required its enzymatic crosslinking activity, as transamidation-inactive TG2-W241A (Pinkas et al., PLOS biology 5, e327, 2007) mutant protein failed to promote OPC proliferation (FIG. 16B). To confirm that TG2 regulates OPC proliferation in a GPR56-dependent manner, OPCs derived from P5 Gpr56$^{+/+}$ or Gpr56$^{-/-}$ pups were cultured in the presence of laminin-111, with or without recombinant TG2. TG2-associated proliferation was attenuated in Gpr56$^{-/-}$ OPCs (FIG. 16C), further supporting a GPR56-dependent TG2 function on OPC proliferation.

Example 8. Transglutaminase 2 (TG2) and Laminin Activate GPR56-Dependent RhoA Pathway To extend our characterization of TG2 as the ligand for GPR56, its ability to activate GPR56 downstream signaling in oligodendrocyte precursors (OPCs) was investigated. RhoA activation lies downstream of OPC GPR56 (Ackerman et al., Nat Commun 6, 6122, 2015; Giera et al., Nat Commun 6, 6121, 2015). Activated RhoA pull-down assays using P9 corpus callosum (CC) of Tgm2$^{-/-}$ mice and littermate controls showed that active RhoA was significantly reduced in CC of Tgm2$^{-/-}$ mice (FIGS. 16D and 16E). Without being bound by theory, this indicated that GPR56 ligation by TG2 in the intact CC activates RhoA to regulate OPC proliferation.

The signaling mechanism was addressed in vitro. As a member of the aGPCR family, GPR56 undergoes GAIN domain-mediated cleavage to generate NTF and CTF (Arac et al., EMBO J 31, 1364-1378, 2012; Hamann et al., Pharmacol Rev 67, 338-367, 2015; Langenhan et al., Sci Signal 6, re3, 2013; Salzman et al., Neuron 91, 1292-1304, 2016). The NTF and CTF remain non-covalently associated on the plasma membrane (Jin et al., Hum Mol Genet 16, 1972-1985, 2007). Ligand binding to the NTF disrupts its interaction with the CTF and activates the receptor by exposing a tethered agonist on the CTF (Luo et al., PLOS One 9, e100043, 2014; Stoveken et al., Proc Natl Acad Sci USA 112, 6194-6199, 2015). Strikingly, TG2, in the presence of laminin-111, removed the GPR56 NTF, thus activating RhoA downstream signaling through the tethered-agonist mechanism (FIGS. 16F-16H, and 17).

The results described herein were obtained using the following materials and methods.

Mouse Strains

All mice were treated according to the guidelines of the Animal Care and Use Committee at Boston Children's Hospital. The Gpr56 knockout mice were obtained from Genentech/Lexicon Genetics. The mutant mice were originally created in a 129/BL6 background, but were derived into the FvB strain and bred into BALB/c strain resulting in a mixed genetic background of the mutant mice of 129/BL6/FvB/BALB/c (Li et al., J Neurosci 28, 5817-5826, 2008). Genotyping was performed by PCR using the following primers: A (5'-CGAGAAGACTTCCGCTTCTG-3'), B (5'-AAAGTAGCTAAGATGCTCTCC-3'), and Neo (5'-GCAGCGCATCGCCTTCTATC-3'). Tgm2 knockout mice were obtained (De Laurenzi and Melino, Mol Cell Biol 21, 148-155, 2001). For Gpr56/Tgm2 double knockout mice, Gpr56 knockout mice were bred with Tgm2 knockout mice. Gpr56$^{fl/+}$ mice were generated at the Mouse Gene Manipulation Core at Boston Children's Hospital (Giera et al., Nat Commun 6, 6121, 2015). Genotyping was performed by PCR with the following primers: primer 1: 5'-tggtagctaacc-tactccaggagc-3', primer 2: 5'-ggtgactttggtgttctgcacgac-3' and primer 3: 5'-cacgagactagtgagacgtgctac-3'.

Pdgfra-Cre/ERT mice in a C57BL/6 background were purchased from Jackson Laboratories (Cat #018280) (Kang et al., Neuron 68, 668-681, 2010) and were crossed with Gpr56$^{fl/fl}$ mice to generate Gpr56$^{fl/fl}$;Pdgfrα-Cre$^+$ mice and their littermate controls. Tgm2$^{fl/+}$ mice were obtained (Northwestern University, Chicago, IL) (Nanda et al., J Biol Chem 276, 20673-20678, 2001) and crossed with Cx3cr1-Cre mice purchased from Jackson Laboratories (Cat #025524) to generate Tgm2$^{fl/fl}$; Cx3cr1-Cre$^+$ mice and their littermate controls. Col3a1 (C.129S4 (B6)-Col3a1$^{tm1Jae}$/J) mice were obtained from the Jackson Laboratory (Cat #002907) in a BALB/c background (Liu et al., Proc Natl Acad Sci USA 94, 1852-1856, 1997).

Antibodies

For IHC or western blot analyses, the following primary antibodies were used: mouse anti-GPR56 (H11) (1:200) (Luo et al., Proc Natl Acad Sci USA 108, 12925-12930, 2011) and rabbit anti-GPR56 (199) (1:200) (Li et al., J Neurosci 28, 5817-5826, 2008), rabbit anti-MBP (Millipore; Cat #AB980, 1:200), rabbit anti-Iba1 (Wako, Cat #019-19741), rabbit anti-GFAP (Abcam, Cat #ab7260), rabbit anti-NG2 (Millipore; Cat #AB5320, 1:200), rat anti-PDGFRα (BD Bioscience; Cat #558774, 1:500), rabbit anti-PDGFRα (Cell Signaling Technologies; Cat #3164S, 1:500), and rat anti-Ki67 (Affymetrix eBioscience; Cat #14-5698-80, 1:100), rat anti-BrdU (Accurate Chemical and Scientific Corporation; Cat #OBT0030S, 1:100), mouse anti-RhoA (Cytoskeleton, Cat #ARH03-A, 1:500), mouse anti-CDK2 (Santa Cruz; Cat #sc-6248, 1:1000), mouse anti-β-actin (Sigma, Cat #A5044, 1:5000), and mouse anti-Ki67 (BD Bioscience; Cat #550609, 1:100). Secondary antibodies were goat anti-mouse or anti-rat conjugated with either Alexa 488 (Life Technologies, 1:1000) or Alexa 546 (Life Technologies, 1:1000) and goat anti-rabbit conjugated with Alexa 546 or 555 (Life Technologies, 1:1000), goat anti mouse or rabbit IgG-HRP (Sigma, Cat #A4416 or A6154, 1:3000).

Purification of GPR56 Immunocomplexes

GPR56$^N$ and GPR56$^{Ndel}$ fusions proteins with either mFc or hFc tag were generated as previously described (Luo et al. Proc Natl Acad Sci USA 108, 12925-12930, 2011). BirA enzyme was used to in vitro biotinylate GPR56$^N$-mFc-biotag protein as previously described (De Laurenzi and Melino Mol Cell Biol 21, 148-155, 2001). Mixed glial cell lysate was incubated with biotinylated GPR56$^N$ protein in lysis buffer [20 mM Hepes (pH 7.3), 150 mM NaCl, and 5 mM MgCl$_2$] with protein inhibitor mixture (Roche Molecular Biochemicals) and 1% Brij 96 (Fluka). Streptavidin beads (Sigma) were used to affinity purify immunocomplexes. GPR56-associated proteins were eluted in 2×SDS loading buffer, subjected to SDS/PAGE. The whole lane was used for MS at the Taplin Biological Mass Spectrometry at Havard Medical School. MS data were searched against the mouse International Protein Index (IPI mouse 339) database using the protein identification software Mascot (v2.2.04, Matrix Sciences) (Luo et al. Proc Natl Acad Sci USA 108, 12925-12930, 2011).

Oligodendrocyte Precursor Cell (OPC) Cultures

Oligodendrocyte precursor cells (OPCs) were isolated from mixed male and female P5-8 Gpr56$^{+/+}$ or Gpr56$^{-/-}$ mouse forebrains as previously described (Wang et al., Neuron 29, 603-614, 2001; Watkins et al., Neuron 60, 555-569, 2008). Briefly, OPCs were purified by negatively selecting with mouse anti-Thy 1.2 (Serotec, Cat #MCA02R) and mouse anti-GalC (Millipore, Cat #MAB342), followed by mouse anti-O4 (O4 hybridoma supernatant) for positive selection. After releasing OPCs from the O4 plate by trypsinization, cells were resuspended in proliferation media containing PDGF-AA and NT-3 (PreproTech). OPCs were plated on coverslips coated with poly-D-lysine before coating with laminin I (R&D Systems, Cat #3400-010-01) or fibronectin (Millipore, Cat #341668) as previously described (Dugas et al., J Neurosci 26, 10967-10983, 2006). After 24 hr, TG2 (2 nM) was added to the cultures and incubated for an additional 24 hr before fixation with 4% PFA and staining for PDGFRα and Ki67.

Mixed Glia Culture

Mixed glia culture was isolated from P1 male and female wt forebrains, as previously described (Giera et al., Nat Commun 6, 6121, 2015; O'Meara et al., Journal of visualized experiments: JoVE, 2011). Briefly, forebrains were dissociated and resulting cell suspension was cultured for 10 days in DMEM containing 10% FBS, 1% GlutaMax at 37° C. and 8.5% CO2. The culture was shaken for 20 hr at 250 rpm and 37° C. to remove OPCs. Mixed glial cells were cultured for another 5-7 days before being washed twice with PBS and collected.

Microglia Isolation

Microglia were isolated as previously described (Cardona et al., Nat Protoc 1, 1947-1951, 2006). Briefly, male and female P7 pups were perfused with ice-cold HBSS, before isolating and mincing the brains. The tissue was homogenized with a dounce homogenizer containing RPMI media before being mixed with stock isotonic percoll (SIP) creating a 30% SIP solution. This cell/SIP mixture was layered on top of a 70% SIP solution before being centrifuged. The resulting interphase containing the microglia was collected and washed with HBSS and cells were counted before being lysed for western blot analysis.

Cuprizone Treatment

Gpr56$^{fl/fl}$;PdgfrαCreER$^-$ and Gpr56$^{fl/fl}$; PdgfrαCreER$^+$ adult mice (8-10 weeks old) were injected with 100 mg/kg/day tamoxifen for 5 consecutive days. Mice were fed a diet containing 0.2% (w/w) cuprizone (Harlan Teklad) ad libitum for 6 weeks. A second pulse of tamoxifen was given at 4 weeks of cuprizone exposure, for 3 days with 100 mg/kg/day. After 6 weeks, mice were returned to normal feed for 3, 7 or 10 days of recovery (DR). Mice were perfused as described above at 0, 3, 7, 10 DR.

Black-Gold Myelin Staining

Coronal brain sections were stained with Black Gold myelin stain (Millipore; Cat #AG105) according to the manufacturer's protocol. Sections were imaged using Nikon Eclipse 80i microscope (Nikon). Representative photographs were obtained with the same exposure setting for control and mutant. Images of the corpus callosum were analyzed using NIH Image J software. The percentage of remyelinated area of the total corpus callosum was determined using a threshold procedure.

Cerebellum Slice Culture and LPC Treatment

Gpr56$^{fl/fl}$;PdgfrαCreER$^-$ and Gpr56$^{fl/fl}$;PdgfrαCreER$^+$ P7 pups were injected with tamoxifen (50 mg kg$^{-1}$) for 3 days before the cerebellar harvesting. All cerebella were harvested on P10 and placed in ice-cold Hank's buffer (Fisher Scientific) before being cut into 300 µm thick sagittal sections with a vibratome (Leica Biosystems). Three slices were placed onto inserts (Millicell 0.4 µm, Millipore) in media containing 50% MEM, 25% Horse Serum, 25% Hank's Buffer, 1% GlutaMax, 5 mg/ml Glucose. After 48 hr, the slices were incubated with 0.25 mg/ml lysolecithin (LPC, Sigma-Aldrich) for 24 hr after which the slices were washed with media and remyelination was allowed to occur for 4 days, with or without 20 nM TG2 protein as indicated in the figures. Slices were fixed with 4% PFA for 20 min, permeabalized with 10% Triton-X 100 at 20 min and blocked with 10% goat serum, 1% bovine serum albumin (BSA) and 0.1% Triton X-100 in PBS for 1 hr at room temperature before being incubated with the primary antibody for neurofilament (mouse anti-NF200 antibody, Abcam) and myelin (rat anti-MBP, Abcam) overnight at 4° C. Primary antibodies were visualized by incubating the sections with the appropriate fluorophore-conjugated secondary antibody for 1 hr at room temperature followed by staining of the nuclei with Hoechst 33342 (1:2000, Life Technologies). After mounting the slices, images were taken with Zeiss LSM 700 confocal microscope. Quantification of myelinated fibers was performed using Image J by subtracting background and applying threshold for both red and green channel, before measuring both myelinated and unmyelinated axon fibers.

Histology Analyses

Mouse brains were harvested after perfusion, fixed with 4% PFA, cryoprotected with 30% sucrose, and embedded in OCT. IHC was carried out as previous described (Jeong et al., J Comp Neurol 520, 2930-2940, 2012). Briefly, after antigen retrieval in Retrievagen A Solution (BD Pharmingen), brain sections were washed with PBS, blocked with 10% goat serum, 1% bovine serum albumin (BSA) and 0.1% Triton X-100 in PBS for 1 hr at room temperature before being incubated with the primary antibody overnight at 4° C. Primary antibodies were visualized by incubating the sections with the appropriate fluorophore-conjugated secondary antibody for 1 hr at room temperature followed by staining of the nuclei with Hoechst 33342 (1:2000, Life Technologies).

In situ hybridization was performed on 12 µm brain sections as previously described (Bialas and Stevens, Nat Neurosci 16, 1773-1782, 2013; Dugas et al., Neuron 65, 597-611, 2010). Probes targeting Plp (Addgene, Cat #22651) and Pdgfra (gift from Charles Stiles) were generated by digesting plasmids with EcoRI and HindIII, respectively. Sp6 and T7 polymerase were used to generate DIG-labeled RNA probes in vitro transcription (Roche Applied Science; DIG RNA labeling kit) as per manufacturer's instructions. Hybridization occurred at 68° C. and washes at 65° C. To detect the DIG-labeled probes, the TSA-Plus Cyanine 3 labeling system (Perkin Elmer) was used according to the manufacturer's instructions.

Ligand binding in situ was performed on male and female P5 wt brains that were embedded into low-melting agarose and sectioned into 500 µm thick sections using a vibratome. Sections were washed with PBS before blocking for 30 min with 0.5% goat serum and 0.1% BSA, incubating with either GPR56$^N$-hFc or GPR56$^{Ndel}$-hFc for 30 min, followed with the appropriate secondary antibody for 30 min. Sections were fixed with 4% PFA for 30 min before being blocked with 10% goat serum, 1% BSA and 0.1% Triton-X 100 for 1 hr. Tissue was incubated with a marker for co-staining overnight at 4° C. followed with the appropriate secondary antibody for 30 min.

All images were captured using a confocal LSM 510 NLO system or a Nikon Eclipse Ti inverted microscope (Nikon). Representative photographs were obtained with the same exposure setting for control and mutant.

Cell Cycle Exit Assay

Cell cycle exit assays were performed as previously described (Giera et al., Nat Commun 6, 6121, 2015). Briefly, proliferating cells were labeled with BrdU (50 mg kg$^{-1}$) by intraperitoneal injection of male and female P13 Tgm2$^{-/-}$ pups and their littermate controls. 24 hr later, mouse brains were harvested after perfusion, fixed with 4% PFA, cryoprotected with 30% sucrose, and embedded in OCT. Brain sections were processed for IHC with anti-BrdU and anti-Ki67 antibodies.

Ligand Binding In Situ

Male and female P5 wt brains were embedded into low-melting agarose and sectioned into 500 µm thick sections using a vibratome. Sections were washed with PBS before blocking for 30 min with 0.5% goat serum and 0.1% BSA, incubating with either GPR56$^N$-hFc or GPR56$^{Ndel}$-hFc for 30 min, followed with the appropriate secondary antibody for 30 min. Sections were fixed with 4% PFA for 30 min before being blocked with 10% goat serum, 1% BSA and 0.1% Triton-X 100 for 1 hr. Tissue was incubated with a marker for co-staining overnight at 4° C. followed with the appropriate secondary antibody for 30 min.

Transglutaminase 2 (TG2) Activation Assay

HEK 293T cells were transiently transfected with mouse Gpr56 cDNA. Twenty-four hours after transfection, the cells were subject to serum starvation for 36 hr followed by the addition of recombinant TG2 250 nM with/without recombinant laminin-111 12.5 nM, or acetic acid as control for 10 min. The conditioned media were harvested, filtered, and concentrated as previously described. Equal volumes of the concentrated media were used for Western blot (Luo et al., PLOS One 9, e100043, 2014), while the cell pellets were used for GTP-Rho pull-down assay.

Western Blot and GTP-Rho Pull-Down Assay

The corpus callosums (CCs) were dissected under a Leica stereo microscope (MZ 6; Leica™ Pte Ltd.), followed by washes in PBS and lysis in ice-cold RIPA buffer (1% Nonidet P-40, 50 mM Tris pH 7.6, 120 mM NaCl, 1 mM EDTA) containing protease inhibitor cocktail set 1 (Calbiochem). The lysates were cleared of insoluble materials by centrifugation at 16,000×g for 10 min at 4° C. Protein concentration was determined by a Bio-Rad protein assay method (Bio-Rad) according to the manufacturer's protocol, and equal amounts of protein were used for SDS-PAGE and western blot analysis. The GTP-Rho pull-down assay was performed as previously described (Luo et al., Proc Natl Acad Sci USA 108, 12925-12930, 2011). In short, tissues were pulverized on liquid nitrogen, lysed in 300 μl of ice-cold RIPA buffer containing protease inhibitors with a cell disruptor for 10 minutes and homogenized with a 26 G syringe needle. Equal amounts of total protein were incubated with 60 μg GST-RBD beads (Cytoskeleton) at 4° C. for 90 min. The beads were washed twice with lysis buffer and once with TBS buffer. Bound Rho proteins were eluted by Laemmli sample buffer and detected by western blot using mouse monoclonal anti-RhoA antibody (Cytoskeleton).

Purification of GPR56 Immunocomplexes

GPR56$^N$ and GPR56$^{Ndel}$ fusions proteins with either mFc or hFc tag were generated as previously described (Luo et al., Proc Natl Acad Sci USA 108, 12925-12930, 2011). BirA enzyme was used to in vitro biotinylate GPR56$^N$-mFc-biotag protein as previously described (Stacey et al., J Biol Chem 277, 29283-29293, 2002). Mixed glial cell lysate was incubated with biotinylated GPR56$^N$ protein in lysis buffer (20 mM Hepes [pH 7.3], 150 mM NaCl, and 5 mM MgCl$_2$) with protein inhibitor mixture (Roche Molecular Biochemicals) and 1% Brij 96 (Fluka). Streptavidin beads (Sigma) were used to affinity purify immunocomplexes. GPR56-associated proteins were eluted in 2×SDS loading buffer, subjected to SDS/PAGE. The whole lane was used for MS at the Taplin Biological Mass Spectrometry at Havard Medical School. MS data were searched against the mouse International Protein Index (IPI mouse 339) database using the protein identification software Mascot (v2.2.04, Matrix Sciences) (Luo et al., Proc Natl Acad Sci USA 108, 12925-12930, 2011).

Zebrafish Stocks and Rearing Conditions

Zebrafish (Danio rerio) were maintained in the Washington University Zebrafish Consortium facility (zebrafish.wustl.edu/). All experiments were performed in compliance with Washington University's institutional animal protocols. Embryos were collected from pair-wise or harem matings and reared at 28.5° C. in egg water (5 mM NaCl, 0.17 mM KCl, 0.33 mM CaCl$_2$), 0.33 mM MgSO$_4$). All zebrafish lines used in these studies were generated in the wt (AB) background, including: gas6$^{st1228}$, mpp6a$^{st1233}$, mpp6b$^{st1234}$, pleca$^{st1261}$, and plecb$^{st1236}$.

Zebrafish Mutant Generation

Zebrafish guide RNAs (gRNAs) were designed and generated and cas9 RNA was synthesized at the Genome Engineering and iPSC center at Washington University School of Medicine (St. Louis, MO). gRNA sequences were as follows:

gas6:
(SEQ ID NO: 27)
5'-CAGAACCCGCAGAGCCAACCAGG-3' mpp6a:
(SEQ ID NO: 28)
5'-GGCGGTTCAAAGTAATAACGTGG-3' mpp6b:
(SEQ ID NO: 29)
5'-GCAGCAGGTGTTGGATAACC-3' pleca:
(SEQ ID NO: 30)
5'-AAAACTAGGGAATAAGACTG-3' plecb:
(SEQ ID NO: 31)
5'-TCCCTCCTGGAGGTCCTCTC 3'

Synthetic CRISPR guide mRNA was combined with cas9 synthetic mRNA and injected into 1-cell stage wt embryos (AB) at 100 pg quantities. To recover germ-line transmitted mutations, injected founders (FOs) were grown to adulthood, outcrossed to wt AB partners, and genomic DNA was extracted from individual F1 embryos for PCR amplification and restriction digest analysis of the targeted region. Genomic DNA from F1 embryos that showed disruption of the target site was then cloned using the TOPO® TA Cloning® kit (Invitrogen) and Sanger sequenced.

Zebrafish Genotyping

To genotype individual larvae for phenotypic analyses, the following primers were used to amplify a 505 bp fragment of gas6 from genomic DNA: 5'-CAGAAGAGCGAAAGTTTGAC-3' (SEQ ID NO: 32) and 5'-CACAGTGAACATCATCGAGT-3' (SEQ ID NO: 33). For gas6$^{st1228/st1228}$, digest analysis was performed restriction using SexAI, which cleaves wt into a 219 bp and a 286 bp fragment, but is unable to cut mutant (501 bp). To amplify mpp6a, the following primers were used to amplify a 317 bp fragment from genomic DNA: 5'-ACCCAGAGGCACTTGATTA-3' (SEQ ID NO: 34) and 5'-GGTTCCTTCAGGATGTTAGA-3' (SEQ ID NO: 35). For mpp6a$^{st1233/st1233}$, restriction digest analysis was performed using HpyCH4IV, which cleaves wt into a 93 bp and a 224 bp fragment, but is unable to cut mutant (316 bp). To amplify mpp6b, the following primers were used to amplify a 400 bp fragment from genomic DNA: 5'-GGAAATGACCTCAGCAGAT-3' (SEQ ID NO: 36) and 5'-CATGCGTTTACCTCATTAGC-3' (SEQ ID NO: 37). For mpp6b$^{st1234/st1234}$, restriction digest analysis was performed using BstNI, which cleaves wt into a 153 bp and a 247 bp fragment, but is unable to cut mutant (394 bp). To amplify pleca, the following primers were used to amplify a 660 bp fragment from genomic DNA: 5'-GTGGCCTTACATGA-CATCTT-3' (SEQ ID NO: 38) and 5'-CTGAATGCT-CACACAATCAC-3' (SEQ ID NO: 39). For pleca$^{st1261/st1261}$, restriction digest analysis was performed using DdeI, which cleaves wt into a 248 bp and a 412 bp fragment, but is unable to cut mutant (640 bp). To amplify plecb, the following primers were used to amplify a 420 bp fragment from genomic DNA: 5'-GCAAGTCAATGGTTACTGGT-3' (SEQ ID NO: 40) and 5'-GTTTTGACGTGGGATTAGAG-3' (SEQ ID NO: 41). For plecb$^{st1236/st1236}$, restriction digest was performed analysis using Hpy188III, which cleaves wt into a 66 bp and a 354 bp fragment, but is unable to cut mutant (407 bp).

Whole Mount In Situ Hybridization

Whole-mount in situ hybridization (ISH) was performed using standard protocols (Thisse and Thisse, 2008). In brief, embryos were fixed at 5 dpf in 4% paraformaldehyde at 4° C. overnight, and then washed into 100% methanol for dehydration. Following dehydration, embryos were washed in 0.2% PBS-Tween (PBSTw), permeabilized in proteinase K (20 mg/µl diluted 1:1000 in 0.2% PBSTw), and incubated with a Digoxygenin-labeled riboprobe again mbp (Lyons et al., Curr Biol 15, 513-524, 2005) overnight at 65° C. in hybridization buffer (50% formamide). Following probe treatment, embryos were washed to remove formamide, blocked in 2% blocking medium supplemented with 10% normal sheep serum and 0.2% Triton, and incubated in primary antibody (anti-DIG, Fab fragments (1:2000), Product #11214667001, Roche) overnight in block. Following primary antibody treatment, embryos were washed in maleic acid buffer with 0.2% triton, and developed by alkaline phosphatase treatment. After complete, embryos were post-fixed in 4% paraformaldehyde and stored long-term in 70% glycerol. Embryos were mounted on slides and imaged at 10× with an AxioCam MRm on a light microscope (Zeiss AxioImager M2). Genotypes were obtained subsequent to larval analyses.

Transmission Electron Microscopy

For mice, postnatal male brains were fixed by perfusion followed by immersion in a mixture of 2% glutaraldehyde and 4% paraformaldehyde in 0.1M sodium cacodylate buffer, pH 7.4. After overnight fixation, brains were postfixed with 1% osmium tetroxide/1.5% potassium ferrocyanide for 1 hr, and after washing samples were incubated in 1% aqueous uranyl acetate for 1 hr followed by subsequent dehydration in alcohol. The samples were incubated in propylene oxide for 1 hr and infiltrated overnight in a 1:1 mixture of propylene oxide and TAAB Epon (Marivac Canada Inc. St. Laurent, Canada). The next day, samples were embedded in TAAB Epon and polymerized at 60° C. for 48 hr. Ultrathin sections (~60 nm) were cut on a Reichert Ultracut-S microtome, mounted on copper grids, stained with lead citrate, and examined with a JEOL 1200EX transmission electron microscope. Images were recorded with an AMT 2k CCD camera. The photographs were analyzed using Image J Software (rsb.info.nih.gov/ij/) to calculate g-ratio and axon diameter. G-ratio was calculated as previously described (Roy et al., Proc Natl Acad Sci USA 104, 8131-8136, 2007).

For zebrafish larvae, transmission electron microscopy (TEM) was performed with microwave-assisted fixation using a PELCO BioWave® Pro with Steady Temp™ Digital Plus water-recirculating system and processed as previously described (Czopka and Lyons, 2011). In brief, embryos were fixed in modified Karnovsky's fix (4% paraformaldehyde, 2% glutaraldehyde, 0.1M sodium cacodylate). After primary fixation, embryos were genotyped and pooled followed by secondary fixation in 2% osmium tetroxide in 0.1M sodium cacodylate and 0.1M imidazole, pH 7.4. Embryos were then washed and treated with saturated uranyl acetate before dehydration using increasing concentrations of ethanol followed by 100% acetone. Embryos were then transferred into a 1:1 mixture of acetone-EPON and infiltrated overnight. Finally, the 1:1 acetone-EPON mixture was replaced with 100% EPON, and samples were embedded in molds for baking overnight at 65° C. Zebrafish larvae were always examined at approximately the same body segment level to control for variability along the anterior/posterior axis. Thin sections (70 nm) were mounted on copper mesh grids and stained with 8% uranyl acetate followed by Sato's lead stain. Sections were viewed and imaged on a JEOL (JEM-1400) electron microscope using an AMT V601 digital camera. All images were processed and analyzed using Image J software. Quantifications were performed blinded to genotype on a stereotyped, 14 µm² region of the ventral spinal cord containing approximately 300 axons from N=4 gas6 wt controls, N=4 gas6$^{st1228/st1228}$ mutants, N=3 mpp6a wt controls, N=4 mpp6a$^{st1233/st1233}$ mutants, N=3 mpp6b wt controls, N=3 mpp6b$^{st1234/st1234}$ mutants, N=3 pleca wt controls, N=3 pleca$^{st1261/st1261}$ mutants, N=5 plecb wt controls, and N=4 plecb$^{st1236/st1236}$ mutants.

Statistical Analysis

For all studies, images were scored blinded to genotype and treatments prior to quantifications. For mouse studies, data is represented as mean±s.e.m and asterisks indicate significance: *P≤0.001; P≤0.01; *P≤0.05. GRAPH-PAD Prism Software (GraphPad Software, Inc.) was used to determine statistical significance between genotypes and treatments using unpaired or paired Student's t-tests, two-tailed and unequal variance depending on animals either being paired prior to data collection or not. For in vitro culture, animals were paired prior to isolation of OPCs. One-way ANOVA followed by Tukey post-hoc was used to analyze multiple treatment condition experiments. For zebrafish studies, data is represented as mean±s.d. and statistical significance was determined using unpaired Student's t-tests, two-tailed with unequal variance. Sample size was not pre-determined by statistical methods, but was based on similar studies in the field.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents, publications, and accession numbers mentioned in this specification are herein incorporated by reference to the same extent as if each independent patent, publication, and accession number was specifically and individually indicated to be incorporated by reference.

What is claimed is:

1. A method of increasing myelination of a neuron and/or increasing oligodendrocyte or precursor thereof proliferation in a subject, the method comprising:
   injecting an effective amount of a vector into the subject thereby contacting an oligodendrocyte or precursor thereof comprising GPR56 in the subject with the vector comprising a nucleotide sequence encoding:
   an amino acid sequence TYFAVLMVS (SEQ ID NO: 1),
   wherein the SEQ ID NO:1 binds GPR56.

2. The method of claim 1, wherein the subject has bilateral frontoparietal polymicrogyria (BFPP).

3. The method of claim 2, wherein the subject has a GPR56 allele comprising a loss-of-function mutation.

4. A method of increasing myelination and/or oligodendrocyte or precursor thereof proliferation in a subject, the method comprising:
   injecting an effective amount of a vector into the subject thereby contacting an oligodendrocyte or precursor thereof comprising GPR56 in the subject with the vector comprising a nucleotide sequence encoding:
   an amino acid sequence TYFAVLMVSSVEVDAVHKHYLS (SEQ ID NO: 2),
   wherein SEQ ID NO:2 binds GPR56.

5. The method of claim 4, wherein the subject suffers from a demyelinating disease, said demyelinating disease is selected from the group consisting of: multiple sclerosis, periventricular leukodystrophy, periventricular leukomalacia, optic neuritis, neuromyelitis optica, acute disseminated encephalomyelitis, idiopathic inflammatory demyelinating disease, central pontine myelolysis, and progressive multifocal leukoencephalopathy.

6. The method of claim 1, wherein the amino acid sequence TYFAVLMVS (SEQ ID NO: 1) is a tethered ligand.

7. The method of claim 1, wherein the amino acid sequence TYFAVLMVS (SEQ ID NO: 1) is covalently linked to a lipid or transmembrane domain.

8. The method of claim 1, wherein the N-terminus or C-terminus of the amino acid sequence TYFAVLMVS (SEQ ID NO: 1) is covalently linked to a lipid or transmembrane domain.

9. The method of claim 4, wherein the amino acid sequence TYFAVLMVSSVEVDAVHKHYLS (SEQ ID NO: 2) is a tethered ligand.

10. The method of claim 1, wherein the subject suffers from a demyelinating disease, said demyelinating disease is selected from the group consisting of: multiple sclerosis, periventricular leukodystrophy, periventricular leukomalacia, optic neuritis, neuromyelitis optica, acute disseminated encephalomyelitis, idiopathic inflammatory demyelinating disease, central pontine myelolysis, and progressive multifocal leukoencephalopathy.

11. The method of claim 4, wherein the subject has bilateral frontoparietal polymicrogyria (BFPP).

12. The method of claim 11, wherein the subject has a GPR56 allele comprising a loss-of-function mutation.

13. The method of claim 4, wherein the amino acid sequence TYFAVLMVSSVEVDAVHKHYLS (SEQ ID NO: 2) is covalently linked to a lipid or transmembrane domain.

14. The method of claim 4, wherein the N-terminus or C-terminus of the amino acid sequence TYFAVLMVSSVEVDAVHKHYLS (SEQ ID NO: 2) is covalently linked to a lipid or transmembrane domain.

* * * * *